United States Patent
Becse et al.

(10) Patent No.: US 11,197,797 B2
(45) Date of Patent: *Dec. 14, 2021

(54) SYSTEM AND METHOD FOR TREATING SOFT TISSUE WITH FORCE IMPULSE AND ELECTRICAL STIMULATION

(71) Applicant: Sigma Instruments Holdings, LLC, Cranberry Township, PA (US)

(72) Inventors: Tamas Becse, Wexford, PA (US); John Crunick, Cranberry Township, PA (US); Louis L. Laskey, Jr., Prospect, PA (US)

(73) Assignee: Sigma Instruments Holdings, LLC, Cranberry Township, PA (US)

( * ) Notice: Subject to any disclaimer, the term of this patent is extended or adjusted under 35 U.S.C. 154(b) by 326 days.

This patent is subject to a terminal disclaimer.

(21) Appl. No.: 16/250,449

(22) Filed: Jan. 17, 2019

(65) Prior Publication Data

US 2019/0142692 A1    May 16, 2019

Related U.S. Application Data

(63) Continuation of application No. 15/373,637, filed on Dec. 9, 2016, now Pat. No. 10,226,397, which is a
(Continued)

(51) Int. Cl.
*A61B 5/05*    (2021.01)
*A61H 23/02*    (2006.01)
(Continued)

(52) U.S. Cl.
CPC ....... *A61H 23/0245* (2013.01); *A61B 5/0533* (2013.01); *A61B 9/00* (2013.01);
(Continued)

(58) Field of Classification Search
None
See application file for complete search history.

(56) References Cited

U.S. PATENT DOCUMENTS 5,366,483 A * 11/1994 Sadkhin ................... A61N 1/00
128/907
9,517,349 B2 * 12/2016 Becse .................. A61N 1/0476
(Continued)

*Primary Examiner* — Ankit D Tejani
(74) *Attorney, Agent, or Firm* — Polsinelli PC

(57) ABSTRACT

A system for treating soft tissue of a patient. The system includes a treatment head and a computer portion. The treatment head includes a probe and an electrode operably coupled to the probe. The probe and electrode are configured to respectively deliver a mechanical force impulse and an electrical stimulation to the soft tissue when placed in operable contact with the soft tissue. The computer portion includes a CPU and is configured to coordinate the delivery of the mechanical force impulse and electrical stimulation relative to each other. The system is configured to sense a shockwave in the soft tissue of the patient, the shockwave resulting from the mechanical force impulse delivered to the soft tissue via the probe. The system is also configured to analyze a characteristic of the sensed shockwave and configure the electrical stimulation to be delivered to the soft tissue via the electrode based on the characteristic analysis of the sensed shockwave. The characteristic may be at least one of frequency of the sensed shockwave, amplitude of the sensed shockwave, and/or wave shape (form) of the sensed shockwave.

19 Claims, 46 Drawing Sheets

Related U.S. Application Data continuation of application No. 14/372,989, filed as application No. PCT/US2013/021973 on Jan. 17, 2013, now Pat. No. 9,517,349, said application No. 15/373,637 is a continuation-in-part of application No. 14/895,843, filed on Dec. 3, 2015, now abandoned, said application No. 15/373,637 is a continuation-in-part of application No. 14/991,732, filed on Jan. 8, 2016, now abandoned, which is a continuation-in-part of application No. 14/205,105, filed on Mar. 11, 2014, now Pat. No. 9,782,324, and a continuation-in-part of application No. PCT/US2012/055551, filed on Sep. 14, 2012, said application No. 15/373,637 is a continuation-in-part of application No. 14/344,313, filed on Sep. 24, 2014, now Pat. No. 10,342,649, said application No. 15/373,637 is a continuation-in-part of application No. 14/344,311, filed on Nov. 20, 2014, now Pat. No. 9,861,547.

(60) Provisional application No. 61/587,484, filed on Jan. 17, 2012, provisional application No. 61/831,054, filed on Jun. 4, 2013, provisional application No. 61/791,203, filed on Mar. 15, 2013, provisional application No. 61/616,967, filed on Mar. 28, 2012, provisional application No. 61/535,225, filed on Sep. 15, 2011, provisional application No. 61/616,989, filed on Mar. 28, 2012, provisional application No. 61/616,974, filed on Mar. 28, 2012.

(51) Int. Cl.

| | | |
|---|---|---|
| *A61B 5/0533* | (2021.01) | |
| *A61H 23/00* | (2006.01) | |
| *A61N 1/04* | (2006.01) | |
| *A61N 1/36* | (2006.01) | |
| *A61B 9/00* | (2006.01) | |
| *A61B 17/22* | (2006.01) | |
| *A61N 1/00* | (2006.01) | |
| *A61N 1/32* | (2006.01) | |
| *A61N 1/372* | (2006.01) | |
| *A61B 90/00* | (2016.01) | |

(52) U.S. Cl.
CPC ..... *A61B 17/22004* (2013.01); *A61H 23/008* (2013.01); *A61N 1/00* (2013.01); *A61N 1/0452* (2013.01); *A61N 1/0476* (2013.01); *A61N 1/326* (2013.01); *A61N 1/36003* (2013.01); *A61N 1/36031* (2017.08); *A61N 1/36034* (2017.08); *A61N 1/37247* (2013.01); *A61B 2090/064* (2016.02); *A61H 2201/0157* (2013.01); *A61H 2201/10* (2013.01); *A61H 2201/123* (2013.01); *A61H 2201/1664* (2013.01); *A61H 2201/1685* (2013.01); *A61H 2201/5005* (2013.01); *A61H 2201/5038* (2013.01); *A61H 2201/5046* (2013.01); *A61H 2201/5058* (2013.01); *A61H 2201/5064* (2013.01)

(56) References Cited

U.S. PATENT DOCUMENTS

| | | | | |
|---|---|---|---|---|
| 10,226,397 | B2* | 3/2019 | Becse | A61H 23/0245 |
| 2006/0122579 | A1* | 6/2006 | Pisciottano | A61H 39/02 |
| | | | | 606/1 |
| 2007/0244488 | A1* | 10/2007 | Metzger | A61B 90/36 |
| | | | | 606/90 |
| 2009/0054908 | A1* | 2/2009 | Zand | A61B 34/30 |
| | | | | 606/130 |

\* cited by examiner

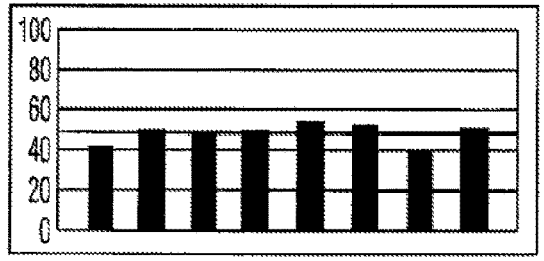
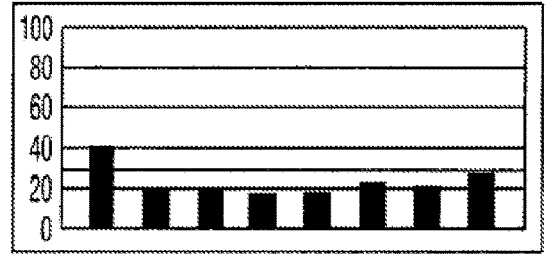
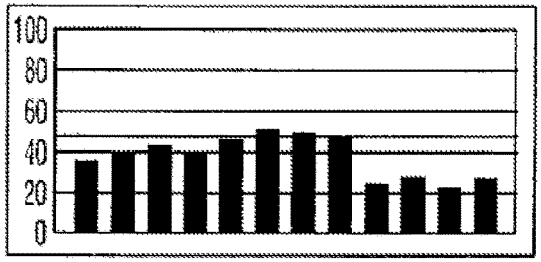
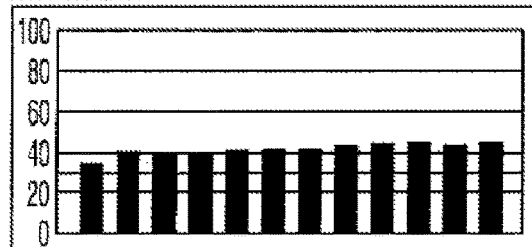
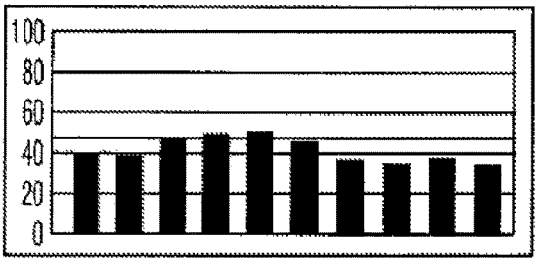
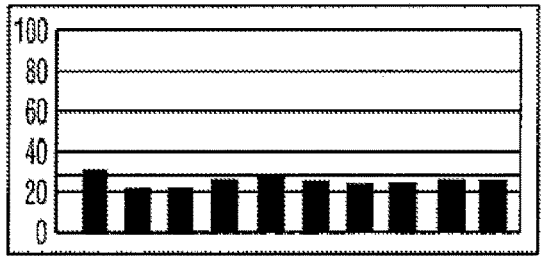
FIG. 5

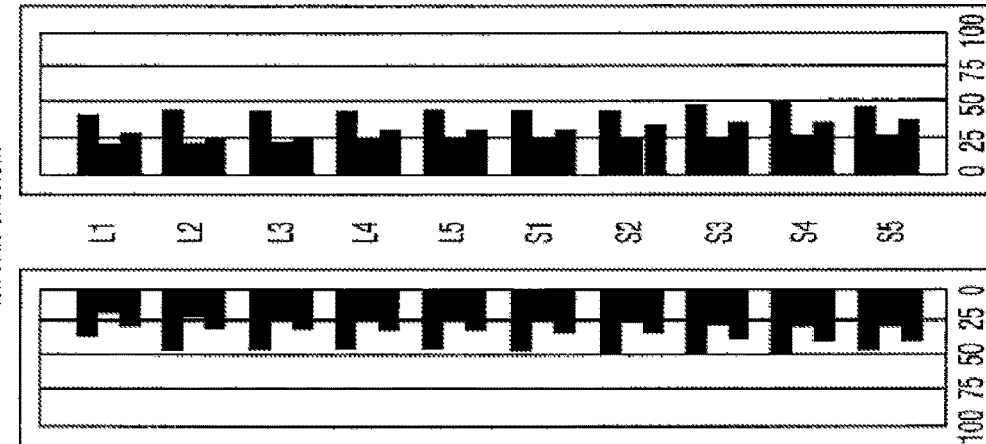
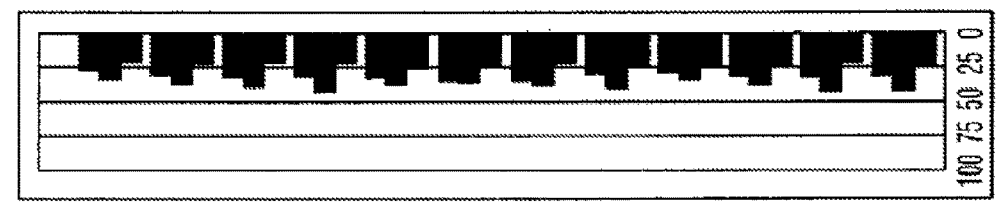
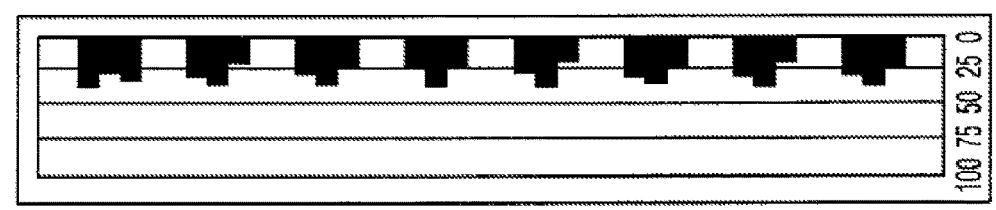
FIG. 6

| | PEAK 1 | PEAK 2 | PT1 | PT2 | RT1 | RT2 | FT1 | FT2 | FREQ 1 | FREQ 2 | PA%1 | PA%2 |
|---|---|---|---|---|---|---|---|---|---|---|---|---|
| C1A | 30.1 | 39.9 | 3.68 | 3.92 | 1.92 | 2.57 | 3.41 | 2.79 | 49.6 | 47.4 | 37.57 | 49.12 |
| C1B | 24.8 | 39.9 | 4.33 | 4.29 | 2.35 | 2.27 | 3.12 | 3.20 | 51.0 | 56.3 | 48.22 | 49.26 |
| C2 | 36.9 | 30.0 | 4.08 | 4.90 | 1.98 | 3.07 | 2.76 | 3.09 | 48.4 | 50.2 | 40.05 | 49.33 |
| C3 | 36.0 | 20.0 | 3.84 | 4.67 | 1.83 | 2.99 | 2.09 | 3.37 | 63.7 | 51.42 | 49.92 | 46.75 |
| C4 | 20.9 | 20.0 | 4.55 | 4.57 | 2.17 | 2.10 | 3.16 | 3.15 | 51.8 | 51.3 | 47.13 | 47.22 |
| C5 | 35.7 | 20.1 | 3.86 | 4.11 | 1.85 | 2.16 | 2.37 | 2.99 | 55.8 | 57.9 | 44.75 | 44.99 |
| C6 | 37.5 | 21.7 | 3.79 | 4.45 | 2.01 | 3.00 | 3.36 | 3.01 | 53.9 | 55.07 | 41.03 | 49.14 |
| C7 | 40.0 | 39.1 | 3.55 | 4.16 | 1.97 | 2.91 | 2.19 | 3.10 | 58.0 | 57.3 | 42.23 | 48.01 |
| T1 | 38.0 | 38.0 | 4.02 | 3.99 | 3.05 | 3.04 | 3.85 | 3.80 | 55.40 | 57.24 | 45.00 | 45.99 |
| T2 | 20.8 | 37.1 | 3.71 | 3.60 | 2.10 | 2.91 | 3.88 | 3.80 | 58.01 | 58.21 | 43.66 | 43.70 |
| T3 | 40.0 | 37.7 | 2.95 | 3.24 | 2.11 | 2.40 | 3.45 | 3.20 | 67.73 | 64.00 | 40.11 | 41.70 |
| T4 | 40.0 | 37.6 | 2.73 | 3.15 | 2.30 | 2.74 | 3.04 | 3.08 | 82.30 | 74.46 | 45.10 | 47.12 |
| T5 | 39.8 | 38.1 | 3.00 | 3.07 | 2.04 | 2.10 | 3.09 | 3.20 | 71.85 | 71.66 | 44.55 | 44.19 |
| T6 | 40.0 | 36.3 | 3.03 | 3.10 | 2.05 | 2.01 | 3.03 | 3.00 | 66.91 | 69.98 | 40.60 | 43.25 |
| T7 | 40.0 | 36.9 | 3.12 | 3.19 | 2.34 | 2.45 | 3.08 | 3.05 | 69.57 | 69.15 | 45.25 | 47.10 |
| T8 | 39.9 | 39.7 | 3.19 | 3.23 | 2.06 | 2.67 | 3.05 | 3.01 | 72.41 | 72.45 | 46.80 | 47.00 |
| T9 | 39.9 | 38.1 | 2.67 | 2.99 | 2.00 | 2.35 | 3.42 | 3.61 | 83.06 | 75.28 | 45.05 | 45.82 |
| T10 | 40.0 | 37.1 | 3.11 | 3.23 | 2.15 | 2.17 | 3.73 | 3.53 | 69.32 | 68.96 | 43.90 | 45.07 |
| T11 | 40.0 | 36.5 | 3.12 | 3.22 | 2.21 | 2.19 | 3.26 | 3.41 | 72.29 | 75.83 | 45.95 | 46.15 |
| T12 | 36.5 | 35.6 | 3.04 | 3.09 | 2.33 | 2.45 | 3.55 | 3.59 | 75.83 | 74.60 | 46.75 | 47.22 |
| L1 | 40.0 | 38.4 | 2.62 | 3.40 | 1.95 | 2.66 | 3.95 | 3.90 | 75.86 | 59.56 | 40.20 | 48.70 |
| L2 | 39.6 | 39.1 | 3.09 | 3.16 | 2.10 | 3.21 | 4.05 | 3.67 | 51.98 | 57.29 | 32.25 | 37.10 |
| L3 | 38.0 | 37.0 | 3.10 | 3.40 | 2.31 | 2.55 | 4.00 | 4.10 | 53.79 | 50.29 | 33.95 | 34.55 |
| L4 | 44.5 | 23.7 | 3.20 | 3.90 | 3.75 | 3.95 | 4.13 | 4.20 | 67.03 | 57.18 | 40.30 | 45.53 |
| L5 | 30.2 | 37.8 | 3.60 | 3.75 | 2.85 | 2.67 | 3.66 | 3.60 | 62.78 | 60.33 | 45.80 | 46.00 |
| S1 | 70.5 | 40.0 | 3.44 | 3.45 | 3.80 | 3.40 | 4.53 | 4.20 | 64.59 | 65.13 | 44.49 | 45.06 |
| S2 | 40.0 | 39.5 | 3.41 | 3.42 | 2.97 | 3.05 | 3.76 | 3.74 | 67.43 | 67.54 | 46.28 | 46.38 |
| S3 | 30.1 | 30.0 | 3.55 | 3.56 | 3.05 | 3.21 | 3.95 | 3.87 | 65.78 | 66.01 | 46.95 | 47.22 |
| S4 | 32.0 | 28.9 | 3.40 | 3.49 | 3.20 | 3.27 | 3.85 | 3.95 | 68.02 | 67.91 | 46.99 | 47.60 |
| S5 | 22.2 | 27.8 | 3.33 | 3.39 | 3.34 | 3.76 | 3.99 | 4.10 | 70.87 | 69.92 | 47.90 | 48.05 |

FIG. 8

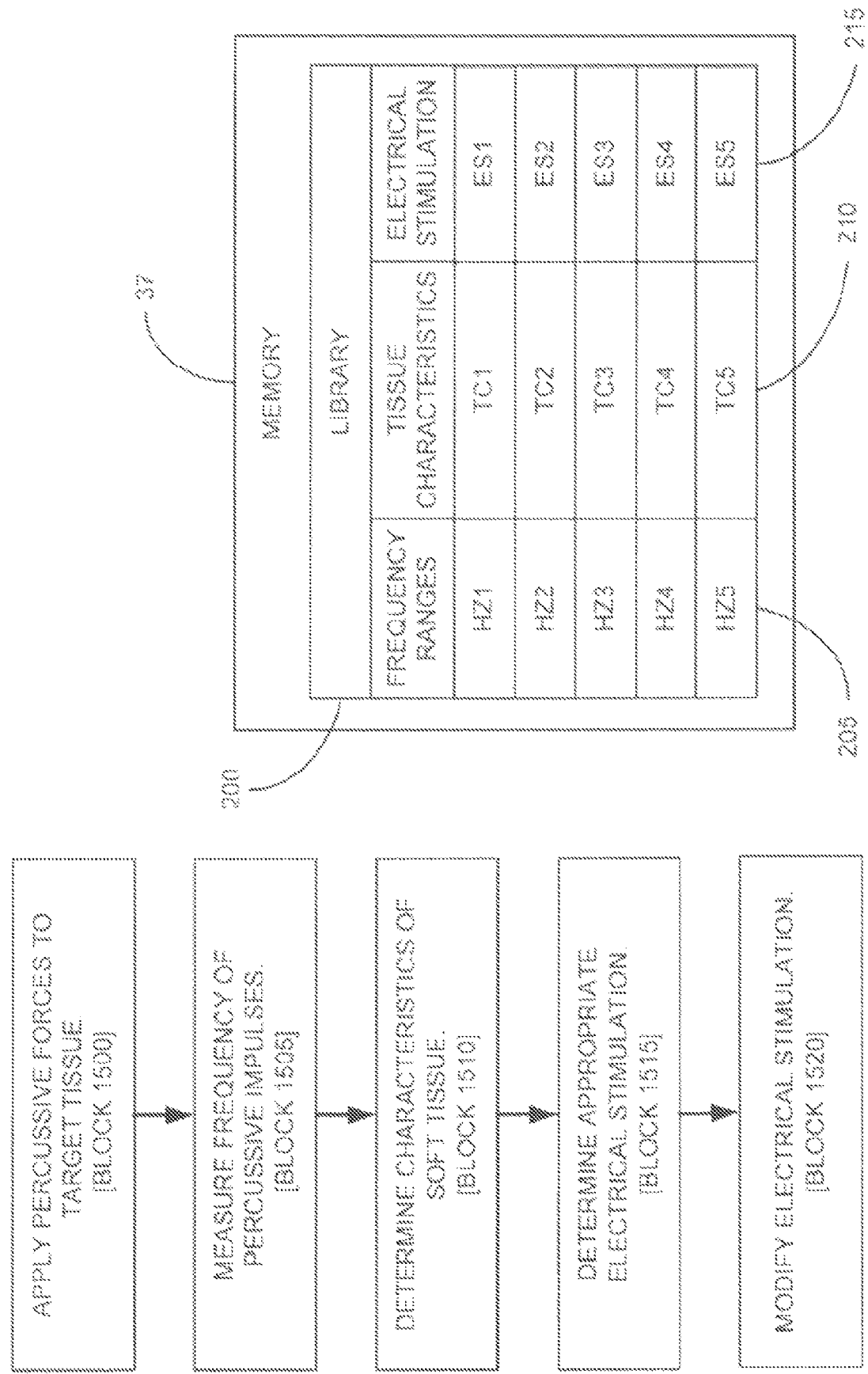

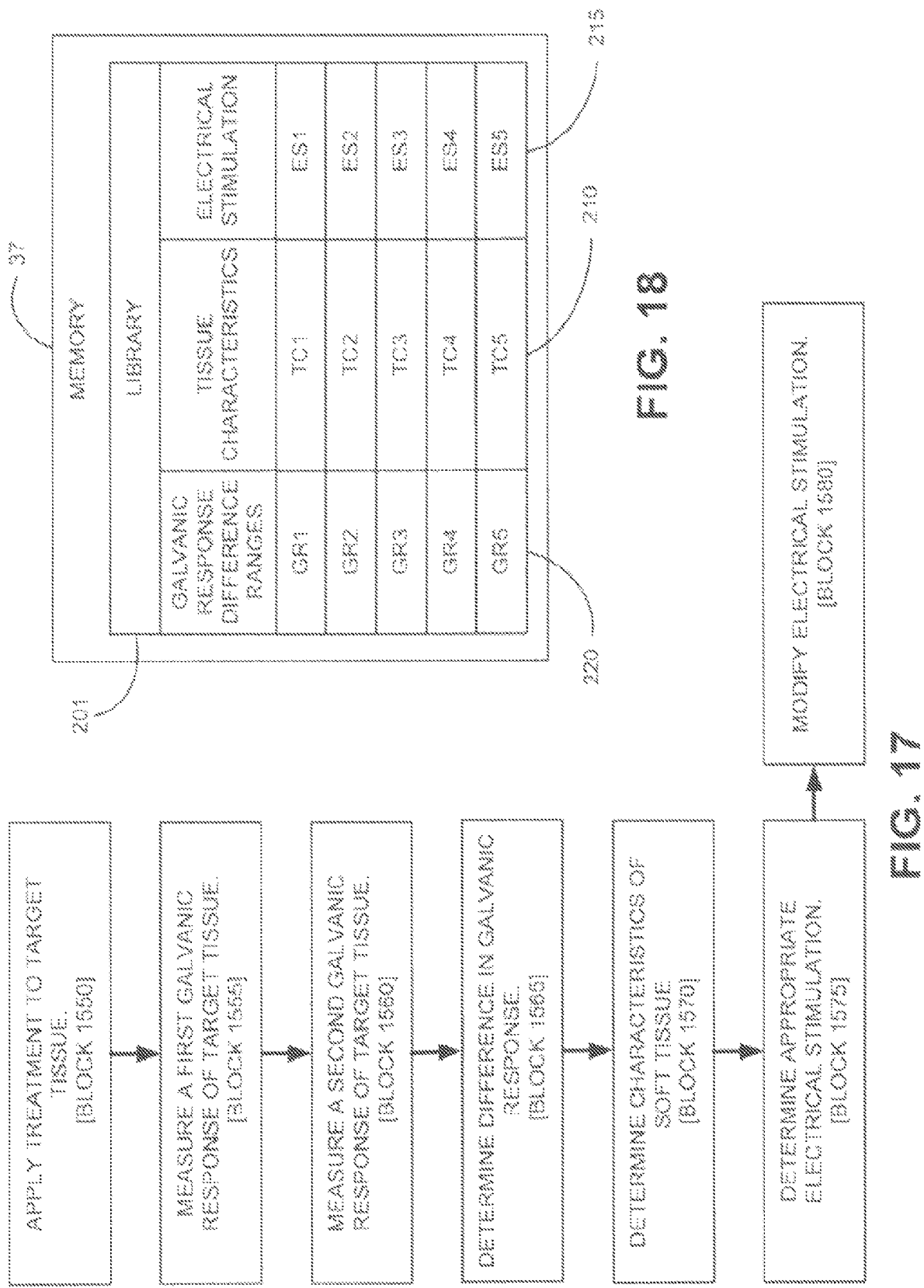

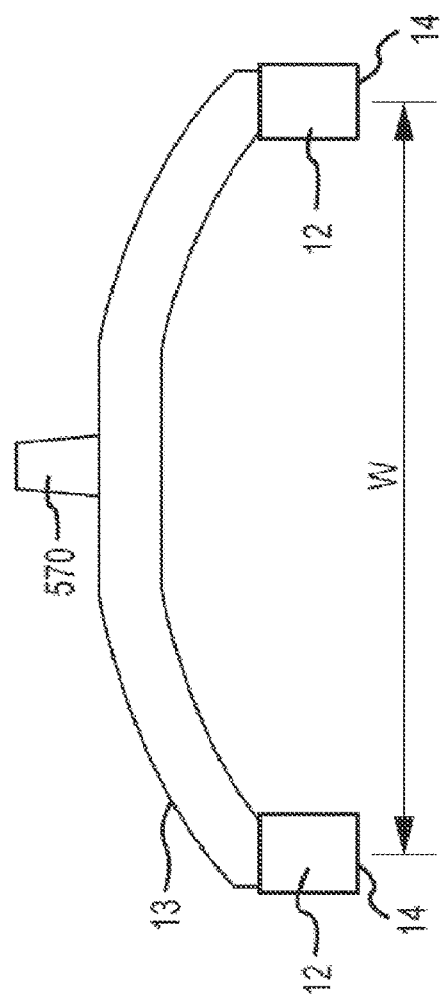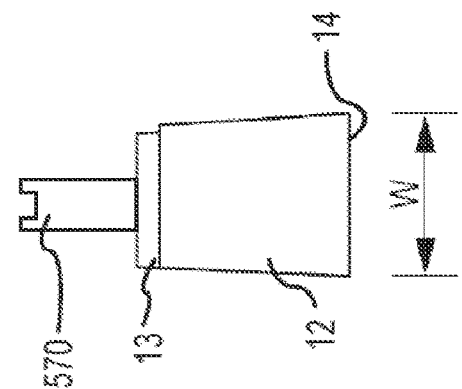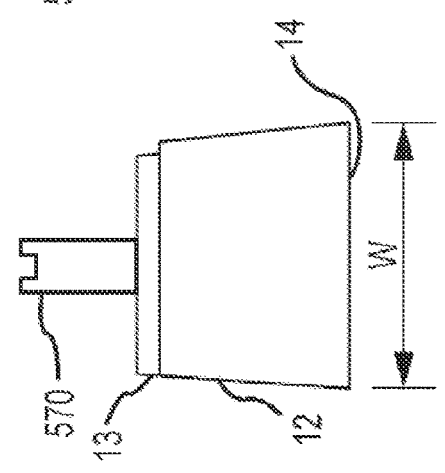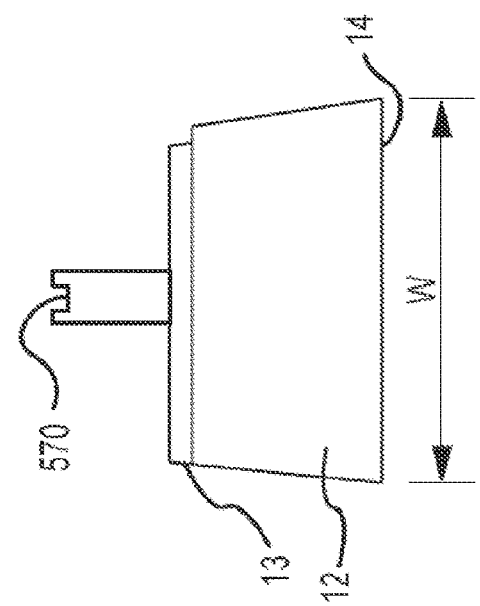

SYSTEM AND METHOD FOR TREATING SOFT TISSUE WITH FORCE IMPULSE AND ELECTRICAL STIMULATION

CROSS REFERENCE TO RELATED APPLICATIONS

The present application is a continuation application of U.S. application Ser. No. 15/373,637 (the '637 application), filed Dec. 9, 2016, which application is a continuation application of U.S. application Ser. No. 14/372,989, filed Jul. 17, 2014, now U.S. Pat. No. 9,517,349, which application is a national stage entry of Patent Cooperation Treaty patent application No. PCT/US2013/021973, filed Jan. 17, 2013, which claims priority to: U.S. Provisional Patent Application No. 61/587,484, filed Jan. 17, 2012.

The '637 application is also a continuation-in-part application of U.S. application Ser. No. 14/895,843 filed Dec. 3, 2015, abandoned, which claims priority under 35 U.S.C. § 119 to U.S. Provisional Patent Application No. 61/831,054, filed Jun. 4, 2013.

The '637 application is also a continuation-in-part application of U.S. patent application Ser. No. 14/991,732, filed Jan. 8, 2016, which is a continuation-in-part application of U.S. patent application Ser. No. 14/205,105 ("the '105 application"), filed on Mar. 11, 2014, now U.S. Pat. No. 9,782,324. The '105 application claims the benefit of U.S. Provisional Application No. 61/791,203 filed Mar. 15, 2013. The '105 application is also a continuation-in-part application of International Application No. PCT/US2012/055551 ("the '551 PCT application") with an international filing date of Sep. 14, 2012. The '551 PCT application claims priority to: U.S. Provisional Patent Application No. 61/616,967, filed Mar. 28, 2012; and U.S. Provisional Patent Application No. 61/535,225, filed Sep. 15, 2011.

The '637 application is also a continuation-in-part of U.S. application Ser. No. 14/344,313, filed Sep. 24, 2014, which claims priority under 35 U.S.C. § 119 to U.S. Provisional Patent Application Nos. 61/535,225, filed Sep. 15, 2011; and 61/616,989, filed Mar. 28, 2012.

The '637 application is also a continuation-in-part of U.S. application Ser. No. 14/344,311, filed Nov. 20, 2014, now U.S. Pat. No. 9,861,547, which claims priority under 35 U.S.C. § 119 to U.S. Provisional Patent Application Nos. 61/616,974, filed Mar. 28, 2012; and 61/535,225, filed Sep. 15, 2011. The contents of each of the above-mentioned patent applications are hereby incorporated by reference in their entireties.

FIELD OF THE INVENTION

Aspects of the present invention relate to medical systems and methods. More specifically, the present invention relates to medical systems for, and methods of, treating soft tissue of a patient in a medical environment such as, for example, physical therapy.

BACKGROUND OF THE INVENTION

Measurement and treatment of soft tissue has been an issue in manual medicine since its inception. Doctors and therapist have always relied on their skills to be able to assess and treat soft tissue problems. The problem is that that there is no way to accurately deliver or record these forces and scientifically measure the results via a dynamic response either before, during or after treatment.

There is a need in the art for a system for, and method of, measuring and treating soft tissue.

BRIEF SUMMARY OF THE INVENTION

Disclosed herein is a system for treating soft tissue. In one embodiment, the system includes a piezoelectric sensor and an electrode. The piezoelectric sensor is positioned between a probe and an anvil driven by an armature driven by a coil of a solenoid. Displacement of the anvil causes displacement of the probe, and the piezoelectric sensor generates a waveform from a force impulse traveling through the probe on account of the probe being displaced against the soft tissue. The electrode is supported on the probe and configured to both administer electrical stimulation to the soft tissue and sense a galvanic response of the soft tissue.

Also disclosed herein is a method for treating soft tissue. In one embodiment, the method includes: select a region of soft tissue for treatment; select a preload tissue compression force and apply the preload tissue compression force to the region, reading and analyzing a tissue signal resulting from the applied preload tissue compression force; read a pretreatment galvanic response of the region; select a type of electrical stimulation with respect to power and type of waveform; select a mode of application of electrical stimulation with respect to continuous current or pulsed current; select a mode of application of percussive impact treatment; apply simultaneously selected percussive impact treatment and selected electrical stimulation treatment type and mode to region via probe and electrodes, respectively; measure soft tissue characteristics of region via piezoelectric sensors; use electrodes to monitor application of, and response to, electrical stimulation during treatment; read galvanic response of region post treatment, store and compare to pretreatment galvanic response; display stored galvanic responses and a difference between the two; and determine change in soft tissue characteristics from change in galvanic response and/or difference in soft tissue characteristic determined via piezoelectric sensor.

Also disclosed herein is a system and process for the application of low level electrical stimulation to soft tissue, dermatomes, nerves and muscles. In one embodiment, the system includes an impulse and sensing head capable of determining the elasticity of soft tissue by applying a force impulse to soft tissue including ligaments, fascia and muscle while at the same time imparting an electrical impulse to stimulate muscles and nerves. The application of the system can be either determined by the therapist or guided by protocols associated with typical manual protocols used in physical medicine specific to but not limited to physical therapy protocols for the purpose of post-operative, rehabilitative and pain abatement outcomes.

Also disclosed herein is a system for the therapeutic treatment of musculoskeletal disorders. The system is configured to simultaneously apply to living tissue electrical stimulation and percussive force. The system includes hardware and software that allows a medical treatment provider to set and control the treatment via a software interface, the software being configured to control a preload force (e.g., tissue compression), the application of a percussive force, and electrical stimulation. The software may allow the medical treatment provider to select: the percussive force settings; the type of electrical stimulation based on power and waveform type; and the mode of application of the electrical stimulation, such as, for example, continuous or pulsed. Further, the software may allow a medical treatment provider to select a treatment area on anatomical drawings displayed on a computer display, the selection being recorded for use in the treatment of the soft tissue via a percussive impact and electrical stimulation under pressure. Also, the computer display may display anatomical views of the human body such that tissues and/or bone are exposed to aid the medical treatment provider in the application of percussive force and electrical stimulation under pressure at appropriate points of treatment. Still further, the software may be configured to allow the selection of a predefined treatment protocol for use in the treatment of soft tissue via a percussive impact and electrical stimulation under pressure.

Also disclosed herein is a system for treating soft tissue of a patient. In one embodiment, the system includes a treatment head and a computer portion. The treatment head includes a probe and an electrode operably coupled to the probe. The probe and electrode are configured to respectively deliver a mechanical force impulse and an electrical stimulation to the soft tissue when placed in operable contact with the soft tissue. The computer portion includes a CPU and is configured to coordinate the delivery of the mechanical force impulse and electrical stimulation relative to each other.

The computer portion may further include a memory, wherein the computer portion causes the electrical stimulation to be delivered relative to the mechanical force impulse according to a treatment protocol stored in the memory. For example, the treatment protocol may cause the electrical stimulation to be delivered generally simultaneously with the delivery of the mechanical force impulse. Alternatively, the treatment protocol may cause the electrical stimulation to be delivered subsequent to the delivery of the mechanical force impulse.

The electrode may be further configured to sense a galvanic response associated with the soft tissue. Accordingly, the computer portion may determine a difference in galvanic response associated with the soft tissue and use the difference in galvanic response to determine a characteristic associated with the soft tissue. The computer portion can then use the characteristic to determine an appropriate electrical stimulation to be delivered to the soft tissue via the electrode. For example, the appropriate electrical stimulation may include at least one of hi voltage mono-phasic, hi voltage bi-phasic, Russian symmetrical bi-phasic, square wave mono-phasic, or square wave bi-phasic.

The treatment head further may further include a force impulse wave sensor configured to sense a frequency of the mechanical force impulse associated with the soft tissue. Accordingly, the computer portion may use the sensed frequency of the mechanical force impulse associated with the soft tissue response to determine a characteristic associated with the soft tissue. The computer portion may then use the characteristic to determine an appropriate electrical stimulation to be delivered to the soft tissue via the electrode. For example, the appropriate electrical stimulation may include at least one of hi voltage mono-phasic, hi voltage bi-phasic, Russian symmetrical bi-phasic, square wave mono-phasic, or square wave bi-phasic.

The computer portion may further include a computer display that displays a representative patient image. Selection of a specific region of the representative patient image may cause the computer portion to determine an appropriate electrical stimulation to be delivered to the soft tissue via the electrode. For example, the appropriate electrical stimulation may include at least one of hi voltage mono-phasic, hi voltage bi-phasic, Russian symmetrical bi-phasic, square wave mono-phasic, or square wave bi-phasic.

The probe may include two tips and the electrode may include an electrode on each tip. Alternatively, the probe may include a single tip and the electrode may include an electrode on the tip and an electrode equipped patch separate from the tip.

Also disclosed herein is a method of treating soft tissue of a patient. In one embodiment, the method includes: a) cause a probe of a treatment head to contact the patient at a target treatment location; b) use the probe to apply a preload tissue compression force to the target treatment location; c) analyze a tissue signal resulting from the application of b); d) select an electrical stimulation to be delivered to the target treatment location, the selection being based off of the analysis of c); e) use the probe to deliver percussive impacts to the target treatment location; and f) use an electrode to deliver the electrical stimulation selected in d) to the target treatment location. The electrode may be supported on the probe. The percussive impacts and electrical stimulation delivered to the target treatment location may be delivered generally simultaneously. The tissue signal of the analysis of c) may include a galvanic response. Additionally or alternatively, the tissue signal of the analysis of c) may include a frequency associated with the target treatment location and resulting from the preload tissue compression force. Also disclosed herein is a system for treating soft tissue of a patient. In one embodiment, the system includes a treatment head and a computer portion. The treatment head includes a probe and an electrode operably coupled to the probe. The probe and electrode are configured to respectively deliver a mechanical force impulse and an electrical stimulation to the soft tissue when placed in operable contact with the soft tissue. The computer portion includes a CPU and is configured to coordinate the delivery of the mechanical force impulse and electrical stimulation relative to each other. The system is configured to sense a shockwave in the soft tissue of the patient, the shockwave resulting from the mechanical force impulse delivered to the soft tissue via the probe. The system is also configured to analyze a characteristic of the sensed shockwave and configure the electrical stimulation to be delivered to the soft tissue via the electrode based on the characteristic analysis of the sensed shockwave. The characteristic may be at least one of frequency of the sensed shockwave, amplitude of the sensed shockwave, and/or wave shape (form) of the sensed shockwave.

The computer portion may further include a memory, wherein the computer portion causes the electrical stimulation to be delivered relative to a treatment mechanical force impulse according to a treatment protocol stored in the memory. For example, the treatment protocol may cause the electrical stimulation to be delivered generally simultaneously with the delivery of the treatment mechanical force impulse. Alternatively, the treatment protocol may cause the electrical stimulation to be delivered subsequent to the delivery of the treatment mechanical force impulse.

The computer portion may include a memory, wherein the computer portion causes the electrical stimulation to be delivered relative to a treatment mechanical force impulse according to a treatment protocol stored in the memory. The treatment protocol may be used to justify continuing to maintain an electrical stimulation treatment already being administered along with a percussive treatment. The treatment protocol may also be used to justify changing the electrical stimulation protocol already being administered along with a percussive treatment to another electrical stimulation protocol.

Also disclosed herein is a system for treating soft tissue of a patient. In one embodiment, the system includes a treatment head and a computer portion. The treatment head includes a probe and an electrode operably coupled to the probe. The probe and electrode are configured to respectively deliver a mechanical force impulse and an electrical stimulation to the soft tissue when placed in operable contact with the soft tissue. The computer portion includes a CPU and is configured to coordinate the delivery of the mechanical force impulse and electrical stimulation relative to each other. The CPU includes a memory including an electrical stimulation protocol database containing multiple treatment protocols referenced to respective multiple affliction diagnoses. The multiple affliction diagnoses may include at least one of muscular dystrophy, multiple sclerosis, muscle atrophy due to stroke or paralysis, pre-operative surgical preparation, post-operative surgical recovery or physical therapy, or discopathy.

A first treatment protocol of the multiple treatment protocols referenced to a first affliction diagnosis of the multiple affliction diagnoses may have unique electrical characteristics as compared to a second treatment protocol of the multiple treatment protocols referenced to a second affliction diagnosis of the multiple affliction diagnoses. The unique electrical characteristics may include at least one of waveform type, output voltage, output current, output frequency, output time, or number of pulses.

The first treatment protocol of the multiple treatment protocols referenced to a first affliction diagnosis of the multiple affliction diagnoses may have unique operator instructions as compared to a second treatment protocol of the multiple treatment protocols referenced to a second affliction diagnosis of the multiple affliction diagnoses. The unique operator instructions may include at least one of electrode number, electrode placement location on the patient body, or probe placement location on the patient body.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

BRIEF DESCRIPTION OF THE DRAWINGS

FIG. 5 shows a computer screen displaying a summary of the peak amplitudes taken from the wave forms on FIG. 3.

FIG. 6 shows a computer screen displaying a summary of the peak amplitudes taken from the wave forms in FIG. 4.

FIG. 8 shows a computer screen displaying a treatment screen.

FIG. 15 is a flow chart illustrating a methodology for selecting an electrical stimulation protocol based off of a measured tissue frequency of percussive impulses.

FIG. 16 is a diagrammatic depiction of a database or library that exists in the memory for use with the methodology discussed with respect to FIG. 15.

FIG. 17 is a flow chart illustrating a methodology of for selecting an electrical stimulation protocol based off of a measured galvanic response.

FIG. 18 is a diagrammatic depiction of another database or library that exists in the memory for use with the methodology discussed above with respect to FIG. 17.

FIGS. 25A-25J shown side elevation views of various probe embodiments.

DETAILED DESCRIPTION

Figure 1:
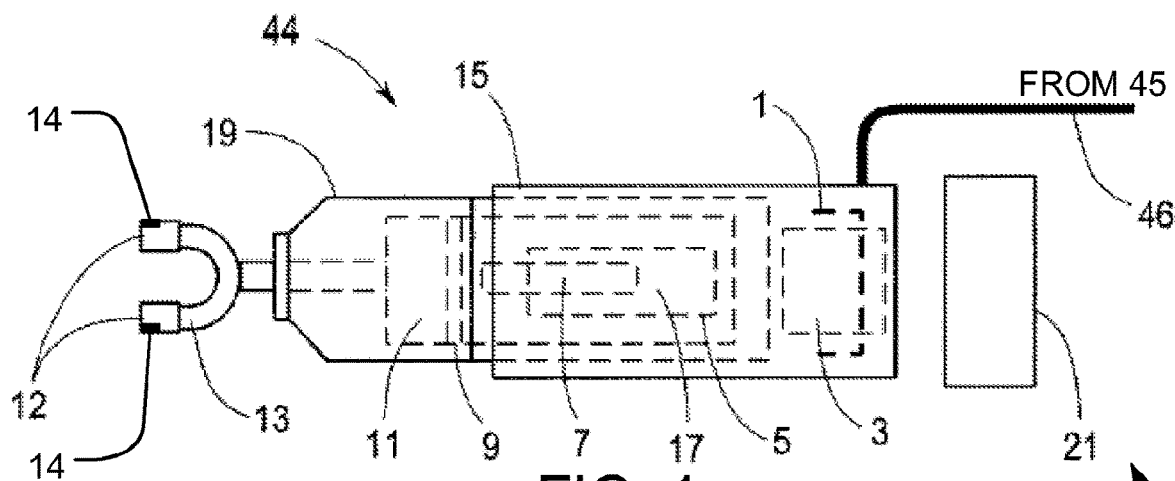
FIG. 1 is a cross-sectional side view of an impulse and sensing head of the system.

Disclosed herein is a system 1111 for, and method of, measuring and treating soft tissue of a patient. The system 1111 is configured for both (1) electrical stimulation of human or animal soft tissue via electrodes 14, and (2) imparting force via a percussive shockwave into human or animal soft tissue including, for example, ligaments, fascia, and muscle. The system 1111 is also configured to record via a computer program 38 the results of the imparted force and/or the electrical stimulation.

In one embodiment, the system 1111 is configured for the measurement of soft tissue response arising from the application of a force impulse and/or electrical stimulus to the soft tissue. In one embodiment, the system includes an impulse and sensing head 44 capable of determining tissue response. The impulse and sensing head 44 is configured to apply a percussive force impulse to soft tissue including, for example, ligaments, fascia or muscle or a combination thereof, and generating a wave form characteristic of the energy absorption profile. Additionally, the system 1111 also includes conductive probes 13 for the purpose of providing electrical stimulation, which is computer controlled, to the skin and dermatomes.

The system 1111, for example, at its impulse and sensing head 44, includes signal generating components attached to the data acquisition circuitry 45 of the head 44 so a signal will be captured by the data acquisition circuitry of the computer portion 45 of the system 1111. Data acquisition circuitry of the computer portion 45 also captures the wave form and a signal characteristic of the resultant force impulse that is indicative of the energy absorption of said tissue.

In one embodiment, the impulse and sensing head 44 includes a probe 13, a piezoelectric sensor 11 firmly attached to the probe 13, an anvil 9 firmly attached to the sensor 11, an electromagnetic coil 5 and an armature 7. The armature 7 is inserted without attachment into the electromagnetic coil 5 and configured so that when the coil 5 is energized, the armature 7 is accelerated to impact the anvil 9 and thereby produce the force impulse, which travels through the piezoelectric sensor 11 and causes the piezoelectric sensor 11 to generate the wave form. A pressure sensor 3 is attached to the head 44 and configured so that when the probe 13 is pressed against the tissue and reaches a predetermined pressure, the pressure sensor 3 causes a release of a burst of current that energizes the electromagnetic coil 5. The pressure sensor 3 is also attached to the signal generating components, which output data, characteristic of the pressure of the probe 13 in contact with the tissue, to the computer 45.

In one embodiment, the tip of the system is constructed with electrodes 14 that are designed to make contact with the skin. At the same instant the force impulse is delivered via the armature 7 being accelerated to impact the anvil 9, an electric pulse is generated and delivered via electrodes 14 to the patient in either a continuous current or as a pulse as selected within the software 38.

In one embodiment, the data acquisition circuitry 45 includes a computer 34, which has a screen 36. An illustration of the soft tissue is displayed on the screen 36. Information indicating the force impulse, the pressure of the probe 13 and the wave form are stored in the computer 34. This information can be merged together, sorted, and logged for each patient. The computer 34 can recall and print this information. The software 38 also allows for various configurations of the electrical stimulation impulse that allows for various types of waveforms and frequencies and power settings.

The graphic display on the computer screen 36 is configured to show parts of the body and allows the doctor or therapist to choose the area of the measurement by using a touch screen 500 to identify and log the area of measurement. Additionally there are pre-programmed protocols that can be used to guide the doctor in the application of the system 1111 for specific conditions.

The system 1111 uses a computer algorithm that may use baseline muscle tension data and/or baseline ligament tension data to give the doctor or therapist information regarding the characteristics of the soft tissue.

The system 1111 can also be used to treat patients. The probe 13 of the invention may oscillate by repetitively accelerating the armature 7 to impact the anvil 9 at a controlled frequency and a predetermined time period. Also, electrodes 14 on the tips 12 of the probes 13 can be used to administer electrical stimulation at the tips 12 of the probes 13. Accordingly, the system 1111 can be applied to the soft tissue to reset the firing patterns of muscle spindle fibers via force impulses while at the same time exciting muscle spindle fibers and dermatomes with electrical stimulation. Preferably, the frequency may be varied between approximately 0.1 Hertz and approximately 12 Hertz in increments of approximately 0.1 Hertz. The electrical stimulation falls within the range used for this common therapy. For example, the electrical stimulation may be varied between approximately 0.1 and approximately 150 Hz.

With respect to soft tissue treatment measurement via piezoelectric sensing devices 11 and the logging of the amplitude of the wave form output from such piezoelectric sensing devices 11, there is complexity in the differing shapes of the wave forms elicited during the mobility testing of soft tissue. Initial experiments and demonstrations have shown that there is useful information trapped in each wave form output of a piezoelectric sensor 11 interposed in a percussion system for testing soft tissue response. The system 1111 employs a method of capturing the mathematic representations of the wave form output from the percussive testing of soft tissue and then manipulating and interpreting such mathematic representations so as to define the amount of soft tissue resistance or mobility and the condition and characteristics of such tissue resistance or mobility.

The system 1111 is configured to analyze the relationship of all of the response factors associated with soft tissue treatment and measurement, namely the analysis of the waveforms as they relate to soft tissue in general. The relation to the stiffness characteristic (waveform peak), the hysteresis function (wave shape), and the frequency response provide valuable information regarding the state of the measured tissue.

In one embodiment, the electrical stimulation unit 100 of the system 1111 employs a high frequency oscillator 105 and a power amplifier 110 to generate a high frequency electrical signal that is then delivered to a transducer, such as an electrode 14. The electrical energy is then transmitted to the patient by applying a probe contact supported electrode against the patient's skin. The amplitude of the electrical signal plays a role in the electrical stimulation of the system 1111 because the lower the amplitude of the electrical signal, the more tolerant the patient is to the stimulation transmitted by the electrode 14.

All tissues in the human body, including skin, have the ability to conduct electricity. Indeed, this is how nerves function to relay information from one part of the body to another. The skin also has electrical activity, which is in constant, slight variation, and can be measured and charted. The skin's electrical conductivity fluctuates based on certain bodily conditions, and this fluctuation is called the galvanic skin response.

Sudden changes in emotion, such as fright, can trigger the galvanic skin response, as can other types of changes, such as the hot flashes that are characteristic of menopause. The galvanic skin response can be graphed on a chart for observation, in the same way that heart or brain activity is recorded.

In one embodiment of the system 1111, the galvanic response of the soft tissue being treated is measured via a conductive sensor 14 to calculate a change in the galvanic response being brought about by the treatment. This change in galvanic response of the soft tissue being treated is used to determine if, and how, the electrical stimulation of the treatment should be changed.

In one embodiment of the system 111, the system 111 includes electrical control circuitry 300 that includes a high frequency oscillator and a power amplifier to generate a high frequency electrical signal that is then delivered to a transducer, such as an electrode 14. The electrical energy is then transmitted to the patient by applying a probe 13 containing the electrode 14 against the patient's skin. The amplitude of the electrical signal is of interest in these electrical stimulation systems because the lower the amplitude of the electrical signal, the more tolerant the patient is to the stimulation transmitted by the electrode 14.

In one embodiment, the electrical stimulation involves placing the electrode 14 on the skin and using various waveforms to stimulate a tissue response, such as, for example, a muscle response in a passive manner.

In one embodiment, the system 1111 will apply a pre load response to compress the tissues during treatment. Pacinian corpuscles are pressure receptors located in the skin and also in various internal organs. Each pacinian corpuscle is connected to a sensory neuron. When pressure is applied via the system probe 13, the pressure receptors elicit a response. However, the pressure receptors adapt very quickly and therefore stop firing. With the system 1111, the pressure that is applied via the probe 13 is augmented by the electrical stimulation provided via the electrodes 14 so as to deter the adaptation and increase the firing rate of the neural channel in addition to the electrical stimulation.

In one embodiment, the system 1111 will also produce during treatment a pressure wave that will stimulate motor neurons (e.g., type I-A) to activate a stretch reflex response. Other areas of the nervous system, such as, for example, nerve roots and ganglia, are also considered targets for this therapy capable of being delivered via the system 1111.

To begin a more detailed discussion of the features, components and operation of the system 1111, reference is made to FIG. 1, which is a cross-sectional side view of an impulse and sensing head 44. As shown in FIG. 1, the system 1111 for measurement of soft tissue mobility may be portable and hand-held and includes a delivery head 44 with an elongated generally cylindrical housing 15 which has an insert 19 that tapers to form a generally conical configuration at the forward end 20. The other end of the housing 15 is provided with a cylindrical closed end 21. The housing 15 and the closed end 21 may be separately connected by a screw threaded connection to provide access into the interior of the housing 15 and to separate the components of the invention for repair, replacement and the like. After housing 15 is unscrewed from closed end 21, it can slide back and insert 19 can also be unscrewed from the housing 15.

A probe 13 is located at the forward end 20 of the housing 15 and includes cushioned tips 12 for contacting the soft tissue to be measured. The probe 13 may be constructed of a rigid material such as metal, plastic, or the like. The probe 13 screws into or frictionally inserts into the piezoelectric sensor 11. Different shaped probes 13 may be used depending on if the apparatus is being used to measure soft tissue or is being used for therapeutic purposes to improve soft tissue. Electrodes 14 may be supported on the probe 13, for example, at the cushioned tips 12, such that the electrodes 14 make good electrical contact with the soft tissue when the probe is applied to the patient.

Within the housing 15 is a solenoid assembly 17. The assembly 17 includes an electromagnetic coil 5 and an armature 7 longitudinally reciprocally mounted without attachment within the coil 5. The armature 7 is configured so that the end of the armature 7 will impact against the anvil 9 when the electromagnetic coil 5 is energized. The anvil 9 is affixed to one side of a piezoelectric sensor 11. The impact produces a force impulse which travels through the piezoelectric sensor 11 and causes the piezoelectric sensor 11 to generate a wave form. When any one of the various probes is placed against the soft tissue of a patient, the other end of the probe 13 resides firmly against the piezoelectric sensor 11 which in turn resides firmly against the anvil 9. A pressure sensor 3 that resides within the housing 15 is interposed between the closed end 21 of the housing 15 and the solenoid 17. The pressure sensor 3, works in concert with each of the other components so that upon reaching a point that corresponds to a predetermined pressure against the soft tissue of a human subject, the pressure sensor 3 causes the release of a burst of current that energizes the electromagnetic coil 5 such that the armature 7 is accelerated to impact with the anvil 9. The pressure sensor may be comprised of a load cell. The impact of said armature 7 against the anvil 9 produces a force impulse which travels directionally, in a continuum with the direction of the armature 7 at impact, through the piezoelectric sensor 11 while at the same time being influenced by the resistance placed upon the piezoelectric sensor 11 by the probe 13 which is contact with the patient. The kinetic energy at the point of impact causes the piezoelectric sensor 11 to emit an electronic wave form which is characteristic of all of the elements of the electromechanical system on one side of the sensor opposed by all of the human elements on the other side of the sensor. The wave form is captured by data acquisition circuitry within a computer portion 45 of the system 1111 and retained therein for wave form analysis by the application of certain algorithms. Preferably, the power supply 41 is in the computer portion 45 of the system 1111 or even in the CPU 34. An insulated cable 46 connects the delivery head 44 to computer portion 45 of the system 1111 and the power supply 41. Alternatively, the current may be supplied through an electrical cord that may be plugged into a suitable electrical outlet or the like which extends into the housing 15.

The mass of the armature 7 is substantially equal to the mass of the anvil 9 so that when the armature 7 strikes the anvil 9 it transfers the energy of the armature 7 to the patient through the cushioned probe 13. The initial positions of the coil and the probe 13 are fixed so that the energy of the system can only be varied by varying velocity of the armature 7 at the point of impact with the anvil 9. The velocity of the armature 7 can be varied by varying the force with which it is accelerated into the electromagnetic coil 5 which is proportional to the current flowing into the coils of the solenoid 17 which in turn is proportional to the voltage. The triggering point at which the solenoid 17 is actuated can be varied by the relative movement pressure of the housing 15 inwardly in relation to the solenoid 17 and the probe 13 so that when the preset pressure has been matched, an electrical circuit is completed to the electromagnetic coil 5.

A single, or preferably, multi-axis inclinometer, disposed within the head 44, will sense the angle of incidence of the probe 13 in contact with the soft tissue being tested simultaneously with the formation of the wave form. The inclinometer 1 is connected by hard-wiring or telemetry to the data acquisition circuitry of the computer portion 45 of the system 1111. A signal corresponding to the angle of incidence will be captured by the data acquisition circuitry of the computer portion 45 and retained for display on the computer screen 36.

As indicated in FIG. 1, the system includes an electrical stimulation unit 100, which employs a high frequency oscillator 105 and a power amplifier 110 to generate a high frequency electrical signal that is then delivered to a transducer, such as an electrode 14 electrically coupled to the electrical stimulation unit 100. The electrical energy is then transmitted to the patient by applying a probe contact supported electrode 14 against the patient's skin. In one embodiment, the electrical stimulation unit 100 is subject to a control sequence or software that causes the delivery of a continuous current or pulse current via the electrodes 14 to the soft tissue at generally the same instant the force impulse is delivered to the soft tissue via the probe 13.

In the one embodiment, the system 1111 herein described may be used for therapeutic as well as analytical applications. For example, after an analysis is completed, a health care practitioner may use oscillating percussion for treatment of soft tissue. This may be accomplished by repetitively accelerating the said armature 7 to impact the anvil 9 thereby causing the probe 13 to oscillate. The percussive force of the probe 13 should be applied to a soft tissue for the purpose of improving/reducing muscle spasm and/or resetting the firing pattern of the muscle spindle fiber as well as exciting neural pathways. This may be done at a controlled impulse frequency of repetitive force impulses at a predetermined time period or a time period selected by the computer as a result of software algorithms. In the preferred embodiment, the frequency of percussion is varied between 4 and 12 Hertz in increments of 0.1 Hertz. Because there is an inclinometer 1 within the therapy delivery head 44, precise angles of therapy may be applied to the patient and documented for future reference. X-ray imaging or other medical imaging may also be used in conjunction with the system 1111 herein described for accurate estimation of the angle of incidence for therapeutic purposes.

The treatment of the soft tissue provided by the oscillating percussion treatment may be enhanced by the simultaneous delivery of electricity to the soft tissue. For example, the electricity may be caused to be administered continuously to the soft tissue over the course of the oscillating percussion treatment. Alternatively, the electricity may be caused to be administered to the soft tissue intermittently in such a manner that the electricity delivery is pulsed to coincide with each pulse of the oscillating percussion treatment. Alternatively, the electricity may be caused to be administered to the soft tissue intermittently in such a manner that the electricity delivery is pulsed to generally occur between the pulses of the oscillating percussion treatment. Also, the electricity may be administered before or after the percussive treatment.

Data characteristic of the angle of incidence, pressure of the probe 13 on the patient, the force impulse via the probe 13, and the electrical impulses delivered to the soft tissue via the electrodes 14 are permanently stored in computer memory 37 for each area of soft tissue tested, inclusive of all of the tests performed on a given patient during a given session so that such information may be combined with the test interpretation as derived from the analysis of the elicited wave form for each soft tissue region tested. A basis or "base line" is provided for comparison to the test angle of incidence so that those test angles can be matched during the performance of additional testing. The stored angle of incidence information along with the test data analysis for each patient session can be recalled and printed. Any part or, if practical, all of the test history of any patient can be combined for inclusion on one or more computer media so as to enable transfer of the records to any other practitioner so equipped to use the information in the furtherance of the care of the patient. Because the test angle is recorded and permanently stored, another doctor giving a second opinion can use the same angle for testing. Therefore, the results of tests performed by different doctors will be more uniform.

Figure 2:
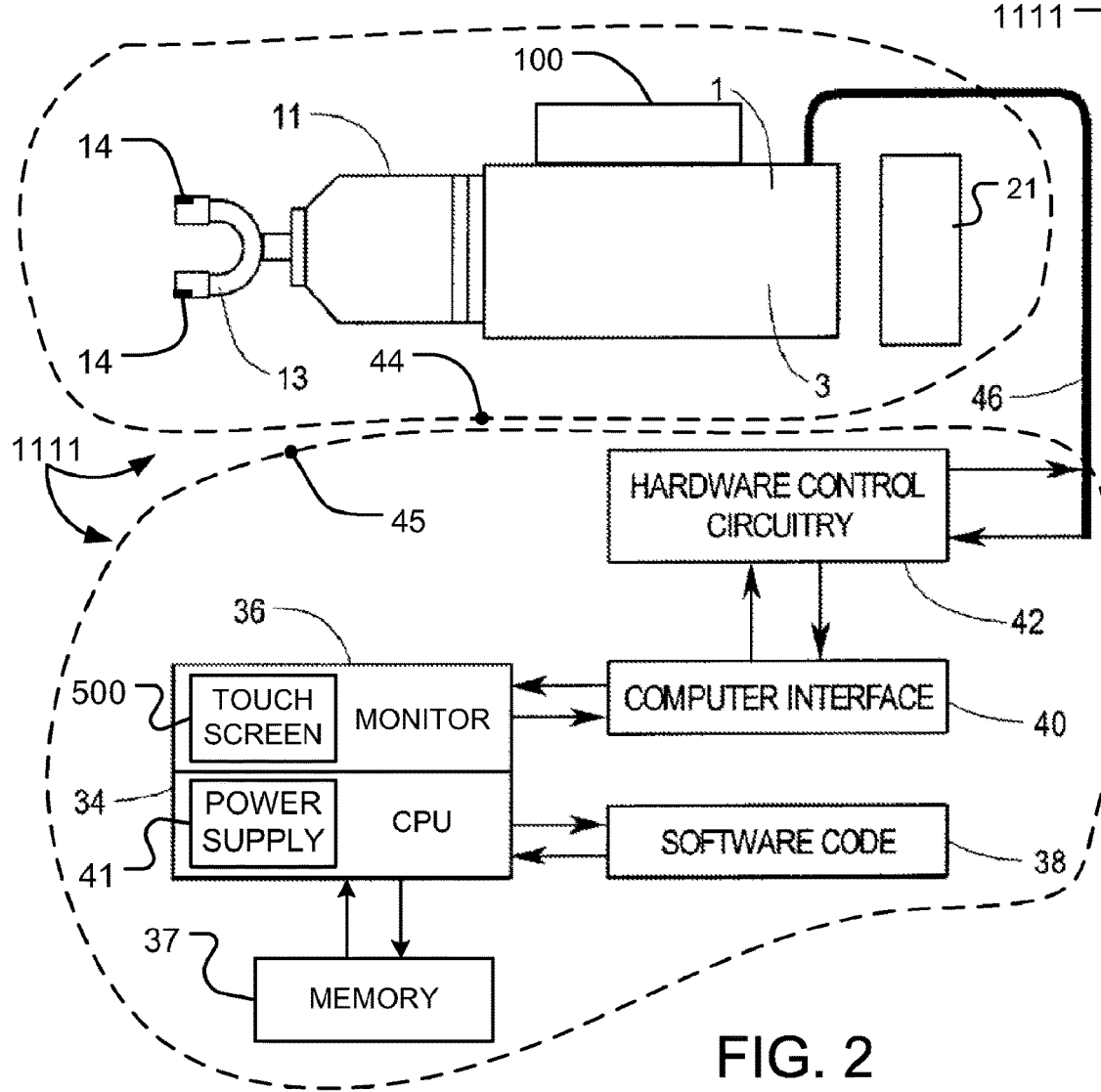
FIG. 2 is a schematic diagram showing the hardware components of the system used to create and capture the wave form.

FIG. 2 is a block diagram of the architecture of the computer portion 45 and piezoelectric impulse and sensing head 44 that form the system 1111. In one embodiment, the computer portion 45 of the system includes a CPU 34, a monitor 36, memory 37, software code 38, a computer interface 40 and hardware control circuitry 42. The electromechanical impulse and sensing head 44 is activated and controlled with the computer software code 38 written onto the CPU 34 that communicates through the interface 40 to hardware control circuitry 42 and to the impulse and sensing head 44. Signals from the sensors 11 within the impulse and sensing head 44 travel to the hardware control circuitry 42 for conditioning and transmittal through the computer interface 40 circuitry to the CPU 34. Software code 38 is used to control and direct all signals between the electromechanical component 44 and the computer portion 45. All relevant information generated by the processes of the system 1111 and used for the processes of the system 1111 are stored in a memory 37 in communication with the CPU 34. The relevant information may be recalled onto the monitor 36 or printed as required.

Similar to the electromechanical impulse and sensing head 44, the electrodes 14 are energized and controlled with computer software code 38 written onto the CPU 34 that communicates through the interface 40 to hardware control circuitry 42 and to the electrodes 14 and the electrical stimulation unit 100. Signals from the sensors 11 within the impulse and sensing head 44, from the electrodes 14 and/or from the components of the electrical stimulation unit 100 travel to the hardware control circuitry 42 for conditioning and transmittal through the computer interface 40 circuitry to the CPU 34. Software code 38 is used to control and direct all such signals between the aforementioned components of the delivery head 44 and the computer portion 45 of the system 1111. All relevant information generated by the process is stored and may be recalled onto the monitor 36 or printed as required.

The resulting wave form is sinusoidal and will be influenced by such things as tissue mobility or resistance to mobility, fascia tension, muscle tonicity, connective tissue resiliency or inertia, local edema, and etc. Each such wave form may be characterized mathematically by logging the peak amplitude, peak time, rise time, fall time, and slew rate. The mathematic values of the data logged will facilitate the calculation of frequency response and certain ratios that will mathematically define the wave form characteristics. By analyzing the mathematics of the wave form characteristics, certain assumptions can be made as to the functional characteristics of the tissue condition.

As the data are collected and logged and after all of the pertinent mathematic calculations are made, a graphic display of the wave form may be presented on a display device, such as, e.g., a computer monitor 36. In addition to the graphic display, the pertinent data and derived ratios may be displayed for assessment by the user of the equipment. The user will be one trained in the interpretation of the wave form shape and interpretation of the logged and derived mathematic information. The graphic displays plus all of the mathematic information as a result of soft tissue percussion testing and/or electrical stimulation may be stored and recalled whenever deemed necessary. As the data base grows and expands, clinical assumptions will yield to statistically valid probabilities and predictive diagnoses. A permanent record of each test of each patient may be stored and recalled as necessary. It may also be copied to electronic storage media, such as, for example, a computer thumb drive, so that it can be transferred to another computer.

As each wave form is recovered from the piezoelectric sensor 11, several things become apparent. The amplitude of the wave form is of interest because as soft tissue resistance increases, the test wave form amplitude increases. Therefore, in FIG. 3 a simple bar chart 67 is used for the expression of wave form peak amplitude. A statistical analysis (mean and standard deviation) of the amplitudes is included. Standard deviation may be set at one, two or three sigma and is expressed by a horizontal line on bar chart 69. The shape of the wave is an interesting piece of information. The expression of a ½ wave form 71 in a graphic display of the wave form shape for all soft tissue regions. A composite of all 7 Cervical, 12 Thoracic, or 10 Lumbosacral wave forms 73 is expressed before treatment and after treatment.

Figure 3:
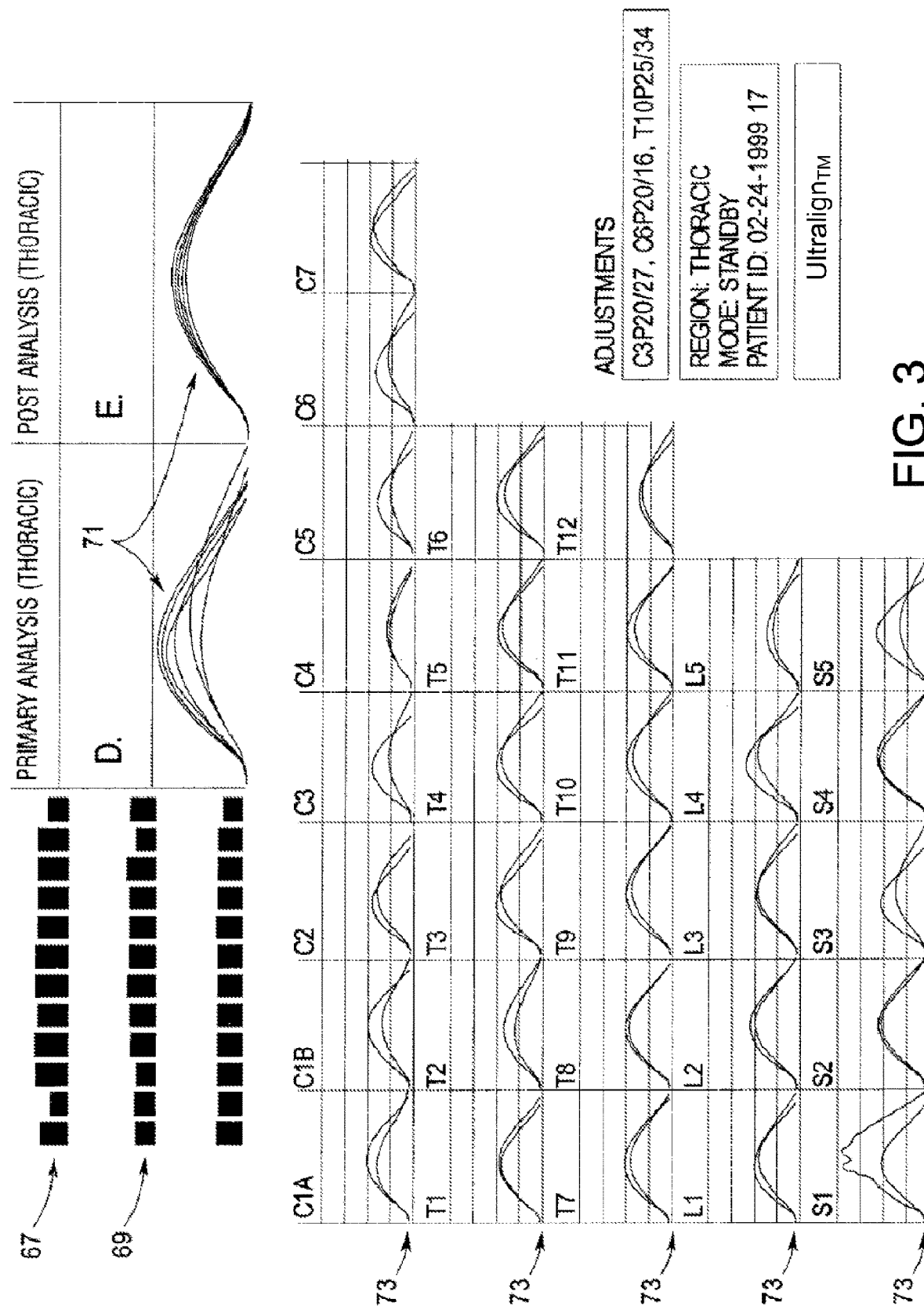
FIG. 3 depicts the thoracic analysis computer screen in the preferred embodiment.
Figure 4:
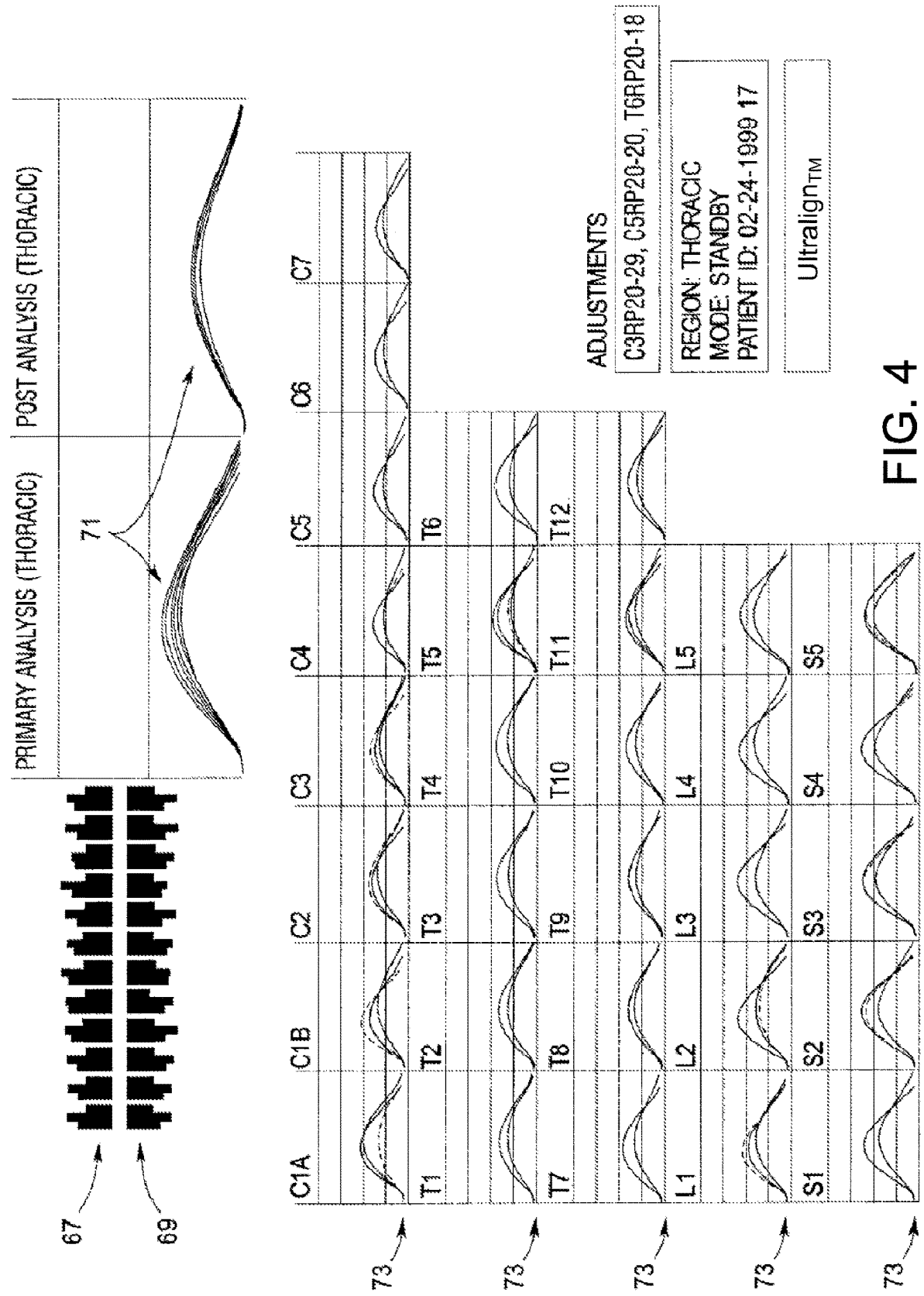
FIG. 4 depicts the lateral cervical analysis computer screen in the preferred embodiment.

Each of the wave forms represented on FIG. 3 and FIG. 4 are analyzed for Peak Amplitude, Peak Time, Rise Time, Fall Time, Frequency (Hertz), Time (%) to Peak and Area (%) to Peak. The derived information is displayed as shown on FIG. 7 along with some calculated factors that are also shown. From the information derived and calculated, a summary table, in FIG. 8, showing all of the derived values may be produced. From the data on FIG. 8, charts may be produced so that the data may be presented in an informational format for comparisons. A sample of these charts is shown as FIGS. 9 through 12. Normal values can be compiled and charted and used to determine normal versus aberrant soft tissue and for comparison to the pre-treatment and post-treatment charts.

Using the information presented as herein described, a practitioner may determine treatment protocol and track progress with objectivity. The practitioner may calculate the resonant frequency of the soft tissue region as a result of the wave form duration in milliseconds and use an algorithm to calculate a harmonic frequency that would be used during patient therapy to control the oscillating percussion used for soft tissue treatment. A history of patient analysis and treatment may be compiled and used for discussion of patient's condition and progress as well as justification for continuing treatment and rehabilitation. Results of rehabilitation may also be used for demonstration of patient cooperation and compliance to a prescribed exercise and rehabilitation program.

As can be understood from the preceding discussion, the system is configured to treat soft tissue via electrical stimulation in conjunction with the application of a simultaneous percussive force. The system includes hardware and software used to deliver, control, and monitor percussive force treatment and electrical stimulation treatment to soft tissue. The controlling and monitoring of the percussive force and electrical stimulation treatment is accomplished via software 38 interfaced with a user via a computer interface 40.

Figure 13:
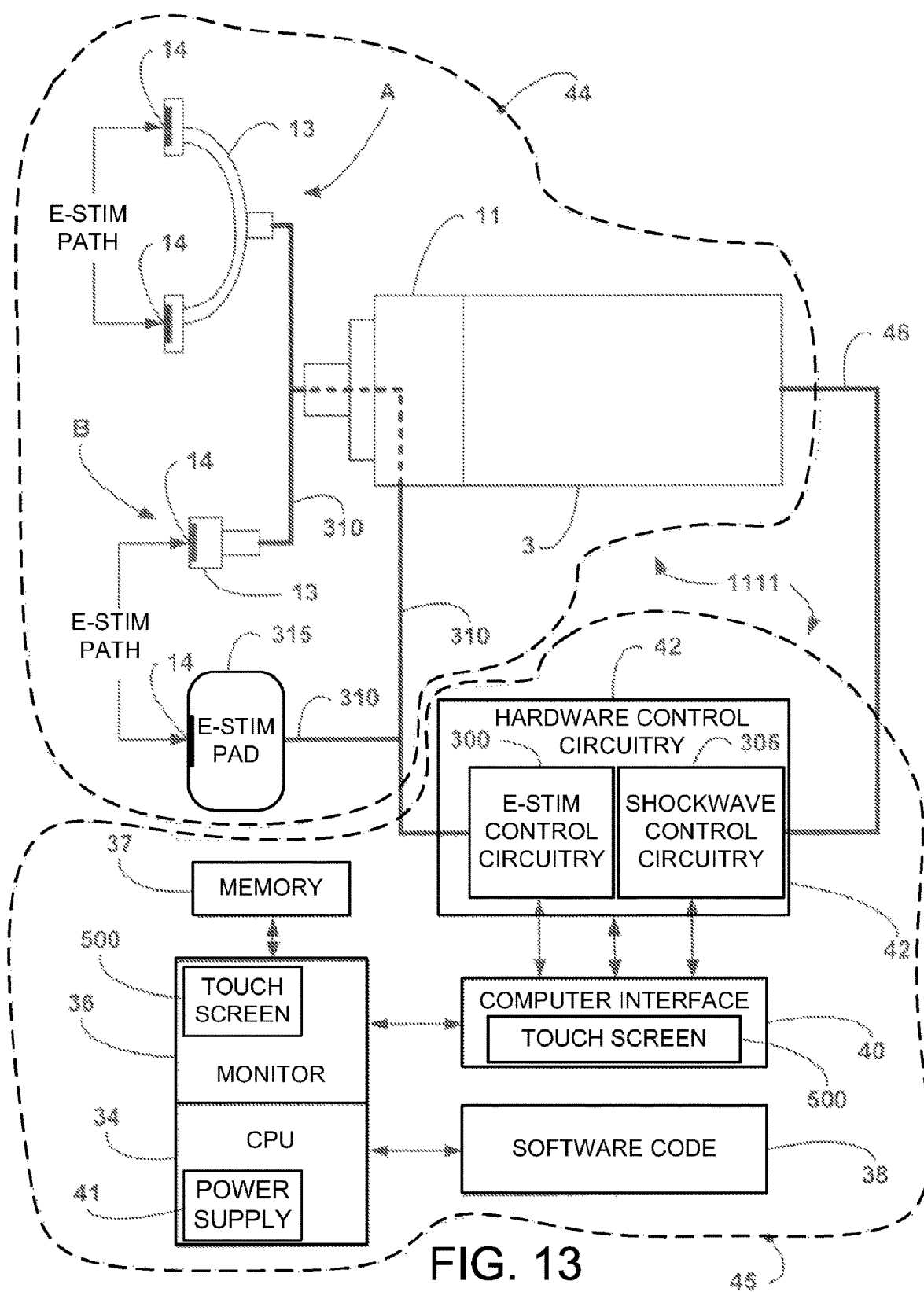
FIG. 13 is a diagrammatic depiction of an embodiment of the system.
Figure 14:
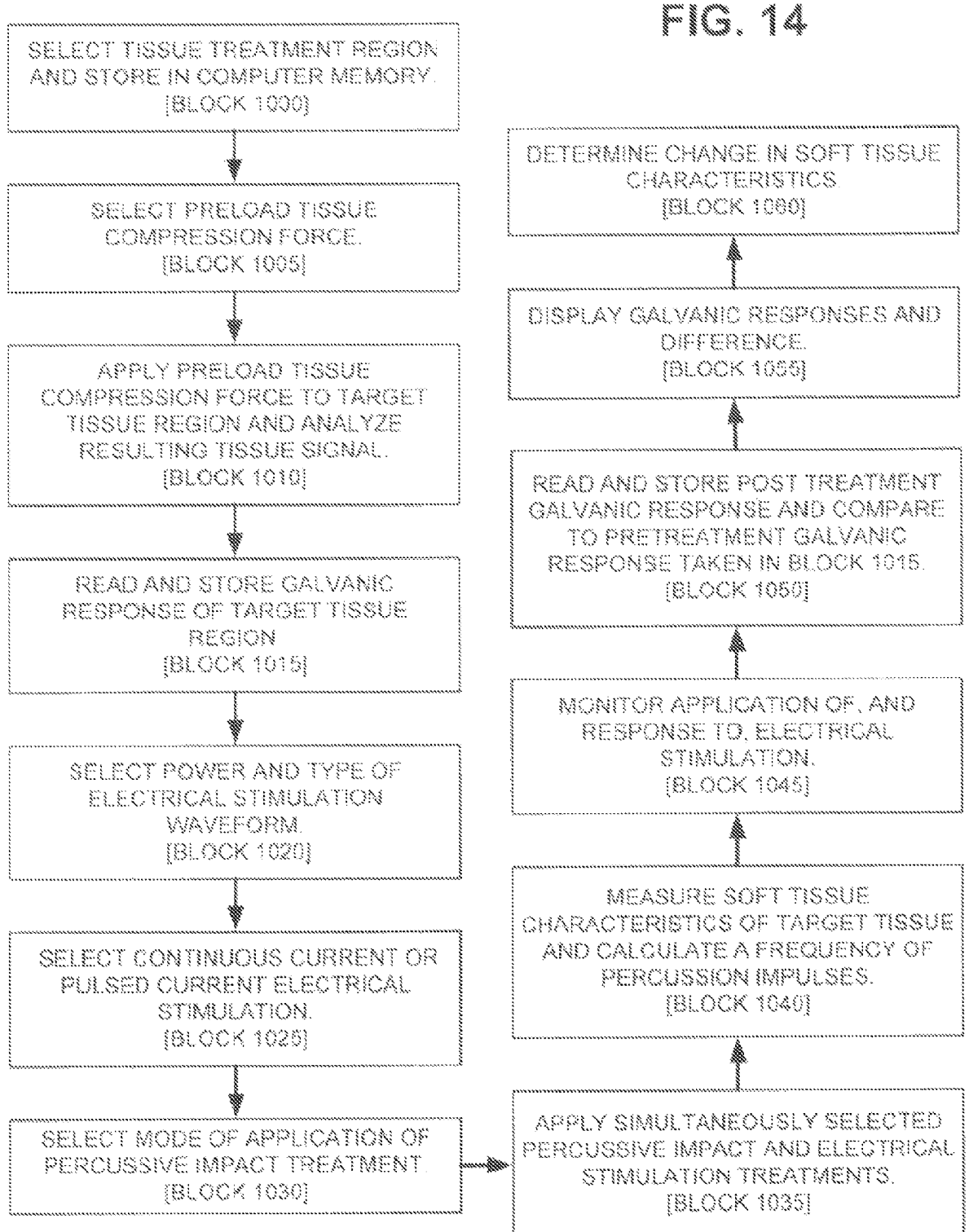
FIG. 14 is a flow chart illustrative of the operation of an embodiment of the system.

As shown in FIG. 13, which is a diagrammatic depiction of an embodiment of the system 1111, the system 1111 includes the components described above with respect to FIGS. 1 and 2, except the hardware control circuitry 42 also includes an EStim control circuitry module 300 and a shockwave control module 305. The EStim control circuitry module 300 is hardwired to the EStim electrodes 14 via cable 310. The electrodes 14 may be on the tips 12 of a dual tip probe 13, as shown at arrow A in FIG. 13. Alternatively, the electrodes 14 may be located on an EStim pad 315 that can be adhered to patient skin and a single tip probe 13, as indicated at arrow B in FIG. 13.

The cable 46 depicted in FIG. 13 electrically couples the shockwave control circuitry module 305 to the components of the delivery head 44 as described above with respect to FIGS. 1 and 2.

In one embodiment, as can be understood from FIGS. 1, 2, 13 and 14, which is a flow chart illustrative of the operation of the system 1111, an anatomical representation of a patient is displayed on the touch screen 500 of the monitor 36, and the operator selects a tissue treatment region on the anatomical representation by touching the screen 500, the selected tissue treatment region being stored in computer memory 37 [block 1000]. A preload tissue compression force may be selected [block 1005]. The tips 12 of the probe 13 are brought into pressed contact with the target tissue region and the preload tissue compression force is applied to the target tissue region by causing the armature 7 to impact the anvil 9, thereby accelerating the probe 13 into the target tissue [block 1010]. The tissue signal resulting from the applied preload tissue compression force is read via the piezoelectric sensor 11 in the sensing head 44 and analyzed and stored [block 1010]. With the probe tips 12 contacting the target tissue region in a manner that places the electrodes 14 in electrical contact with the target tissue region, the galvanic response of the target tissue region is read via the electrodes 14 and associated hardware and software and stored [block 1015]. A type of electrical stimulation is selected with respect to power and type of waveform [block 1020]. A mode of application of the electrical stimulation with respect to continuous current or pulsed current is selected [block 1025]. A mode of application of the percussive impact treatment is selected [block 1030]. The percussive impact treatment and electrical stimulation treatment may be selected from a plurality of predefined treatment protocols.

In one embodiment, the selected percussive impact treatment and selected electrical stimulation treatment are applied simultaneously to the target tissue region via the probe 13 and electrodes 14, respectively [block 1035]. Alternatively, in other embodiments, while the electrical stimulation treatment and percussive impact treatment may be applied over the same treatment period, the delivery of the electrical stimulation and percussive impacts may be alternated back and forth such that the two types of treatment do not occur simultaneously.

The percussive delivery head 44 is used to measure the soft tissue characteristics of the target tissue region by use of piezoelectric sensors 11 to calculate a frequency of percussion impulses based on the soft tissue response [block 1040]. The electrodes 14 are used to monitor the application of, and the response to, the electrical stimulation during treatment [block 1045]. The application of the electrical stimulation can be modified based on data obtained from operations of block 1045. In one embodiment, the operation of the system 1111 may further continue wherein the galvanic response of the target tissue region is read post treatment via the electrodes 14 and associated hardware and software and stored and compared to the pretreatment galvanic response taken in block 1015 [block 1050]. The two stored galvanic responses and the difference between the two are displayed via the user interface [block 1055]. A change in soft tissue characteristics can be determined from the change in galvanic response and/or the difference in soft tissue characteristics determined via the piezoelectric sensors 11 [block 1060].

FIG. 15 is a flow chart illustrating a methodology for selecting an electrical stimulation protocol based off of a measured tissue characteristic (e.g., frequency) of percussive impulses. The selection of the electrical stimulation protocol can occur during the course of the target tissue receiving treatment in the form of percussive impulse, the electrical stimulation protocol selection methodology being used to: 1) justify continuing to maintain the electrical stimulation protocol already being administered along with treatment; or 2) change the electrical stimulation protocol already being administered along with the treatment to another electrical stimulation protocol.

As can be understood from FIG. 15, in one embodiment, percussive forces are applied to the target tissue via the probe 13 [block 1500]. The piezoelectric sensor 11 is used to measure a frequency of the percussive impulses based on the soft tissue response [block 1505]. Characteristics of the soft tissue are determined from the measured frequency [block 1510]. The determined characteristics are used to determine an appropriate electrical stimulation [block 1515]. While the treatment pressure is applied via the probe 13, the electrical stimulation delivered via the electrodes 14 is modified according to the determined appropriate electrical stimulation [block 1520].

FIG. 16 is a diagrammatic depiction of a database or library 200 that exists in the memory 37 for use with the methodology discussed above with respect to FIG. 15. As shown in FIG. 16, the library 200 includes specific frequencies or frequency ranges 205 (e.g., HZ1-HZ5) stored in a correlated manner with respective specific corresponding tissue characteristics 210 (e.g., TC1-TC5). The specific tissue characteristics 210 (e.g., TC1-TC5) are also stored in the library 200 in a correlated manner with respective specific electrical stimulation treatment protocols 215 (ES1-ES5).

As can be understood from FIGS. 15 and 16, percussive forces are applied to the target tissue via the probe 13 per block 1500 and a resulting tissue frequency is measured per block 1505. Per block 1510, the measured tissue frequency is compared to the frequency ranges 205 in the library 200 and, for the sake of this example, the measured tissue frequency falls within frequency range HZ3, which correlates with tissue characteristic TC3. Per block 1515, the determined tissue characteristic TC3 allows a corresponding electrical stimulation protocol 215 to be determined, which in this example, will be electrical stimulation ES3. Per block 1520, the ES3 electrical stimulation protocol is applied to the tissue, which may: 1) simply result in the ES3 electrical stimulation protocol being applied with the percussive impulses being, or yet to be, applied; or 2) cause the electrical stimulation currently being applied with the currently being applied percussive impulses to change to the new ES3 electrical stimulation protocol determined in block 1515.

While the embodiment discussed with respect to FIGS. 15 and 16 is given in the context of the analyzed characteristic of the waveform being the frequency of the waveform, in other cases the analyzed characteristic of the shockwave waveform may be its amplitude, wave shape, or anyone or more of its frequency, amplitude or wave shape.

FIG. 17 is a flow chart illustrating a methodology of selecting an electrical stimulation protocol based off of a measured galvanic response. The selection of the electrical stimulation protocol can occur during the course of the target tissue receiving treatment in the form of electrical stimulation and/or percussive impulse, the electrical stimulation protocol selection methodology being used to: 1) justify continuing to maintain the electrical stimulation protocol already being administered along with the treatment; or 2) change the electrical stimulation protocol already being administered along with the treatment to another electrical stimulation protocol.

As can be understood from FIG. 17, in one embodiment, treatment in the form of electrical stimulation and/or percussive impulses is applied to the target tissue via electrodes 14 and/or the probe 13, respectively [block 1550]. Acting as a conductive sensor, the electrodes 14 are used to measure a first galvanic response of the target tissue at an initial point in time in the treatment, the first galvanic response being in response to the treatment of block 1550 [block 1555]. Again acting as a conductive sensor, the electrodes 14 are used to measure a second galvanic response of the target tissue at a subsequent point in time in the treatment, the second galvanic response being in response to the treatment of block 1550 [block 1560].

The first and second galvanic responses are compared to determine a difference in galvanic response [block 1565]. Characteristics of the soft tissue are determined from the determined difference in galvanic response [block 1570]. The determined characteristics are used to determine an appropriate electrical stimulation [block 1575]. While the treatment being is applied via the electrodes 14 and/or probe 13, the electrical stimulation delivered via the electrodes 14 is modified according to the determined appropriate electrical stimulation [block 1580].

FIG. 18 is a diagrammatic depiction of another database or library 201 that exists in the memory 37 for use with the methodology discussed above with respect to FIG. 17. As shown in FIG. 18, the library 201 includes specific galvanic response differences or galvanic response difference ranges 220 (e.g., GR1-GR5) stored in a correlated manner with respective specific corresponding tissue characteristics 210 (e.g., TC1-TC5). The specific tissue characteristics 210 (e.g., TC1-TC5) are also stored in the library 201 in a correlated manner with respective specific electrical stimulation treatment protocols 215 (ES1-ES5).

As can be understood from FIGS. 17 and 18, treatment in the form of electrical stimulation and/or percussive impulses is applied to the target tissue via the electrodes 14 and/or probe 13 per block 1550, and a first galvanic response is measured per block 1555. The treatment continues, and a second galvanic response is measured per block 1560. Per block 1565, the first and second galvanic responses are compared to determine a galvanic response difference, Per block 1570, the determined galvanic response difference is compared to the galvanic response difference ranges 220 in the library 201 and for the sake of this example, the determined galvanic response difference falls within galvanic response difference ranges GR4, which correlates with tissue characteristic TC4. Per block 1575, the determined tissue characteristic TC4 allows a corresponding electrical stimulation protocol 215 to be determined, which in this example, will be electrical stimulation ES4. Per block 1580, the ES4 electrical stimulation protocol is applied to the tissue, which may: 1) simply result in the ES4 electrical stimulation protocol being applied with the treatment being, or yet to be, applied; or 2) cause the electrical stimulation currently being applied with the currently being applied treatment to change to the new ES4 electrical stimulation protocol determined in block 1575.

In some embodiments, the methodology discussed above with respect to FIGS. 17 and 18 is implemented via a system 1111 as shown in FIGS. 2 and 13, wherein the system 1111 includes software 38 and hardware (e.g., electrodes 14, CPU 34, memory 37, computer interface 40, hardware control circuitry 42, conductive cables 46, 215, etc.) that allows for the measurement of a galvanic response of target tissue before, during and/or after a treatment (e.g., electrical stimulation and/or percussive impulse) is applied to the target tissue. Also, the system 1111 as shown in FIGS. 2 and 13 includes software 38 and hardware (e.g., monitor 36, etc.) that allows the pre and post galvanic response to be displayed both before and after treatment.

As can be understood from FIGS. 2 and 13, the system 1111 includes a monitor 36 with a touch screen interface 500 that allows an operator to select treatment protocols and set treatment parameters. The touch screen 500 displays different screen display arrangements. For example, a treatment display screen, which functions according to the method flow chart depicted in FIG. 19, may be displayed on the touch screen 500.

Figure 19:
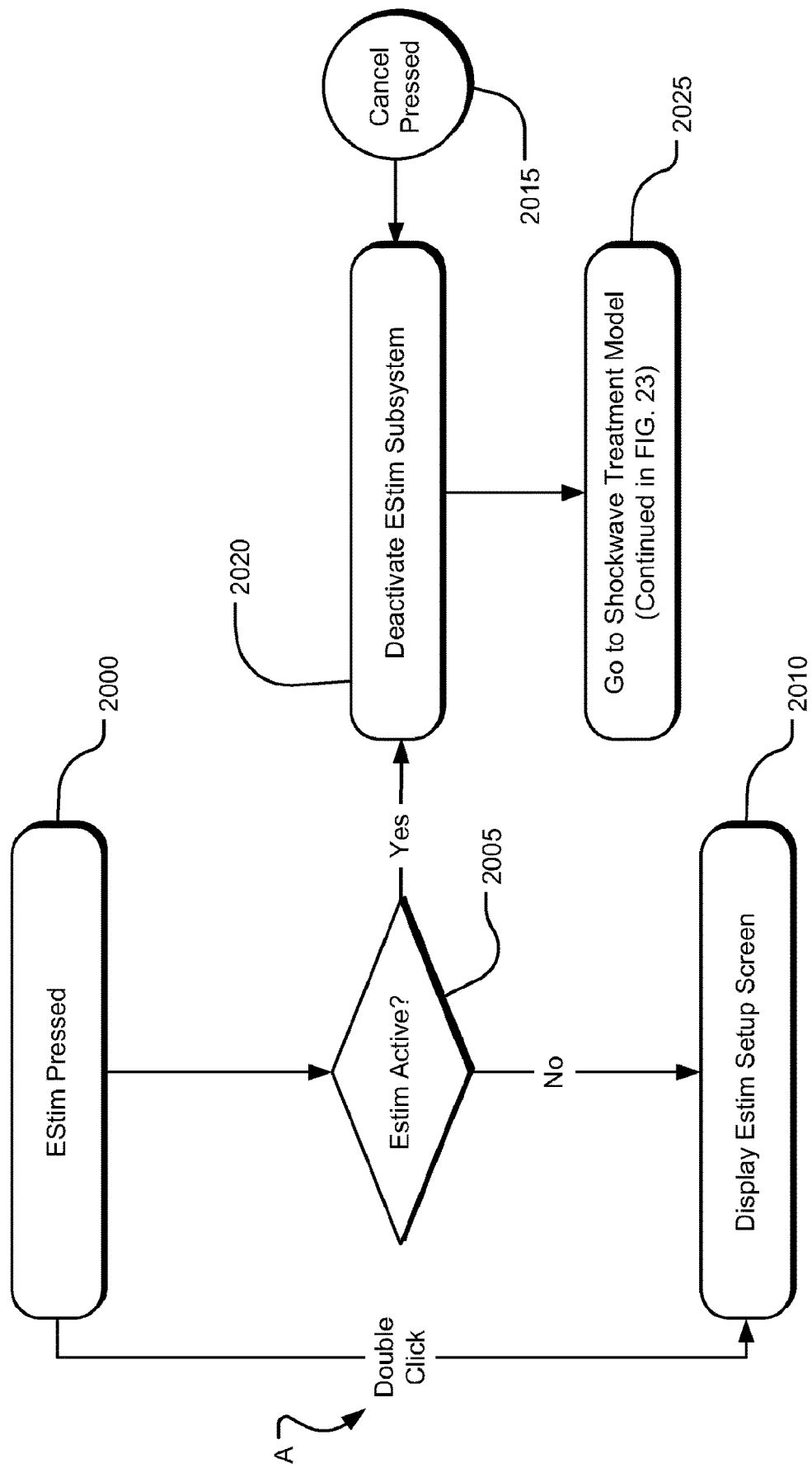
FIG. 19 is a method flow chart for a treatment display screen that may be displayed on the touch screen of the computer interface.

As can be understood from FIG. 19, the operator elects to utilize electrical stimulation as part of the treatment of the patient with the system 1111. The operator presses an EStim initialization button on the touch screen 500 [block 2000] and the system 1111 determines if the EStim capability is active or not [block 2005]. If the EStim capability is not active, the system 1111 displays an EStim setup display arrangement on the touch screen 500 of the monitor 36 [block 2010]. Alternatively, as indicated at arrow A in FIG. 19, the operator can simply "double click" the EStim initialization button to cause the display of the EStim setup screen.

Figure 20:
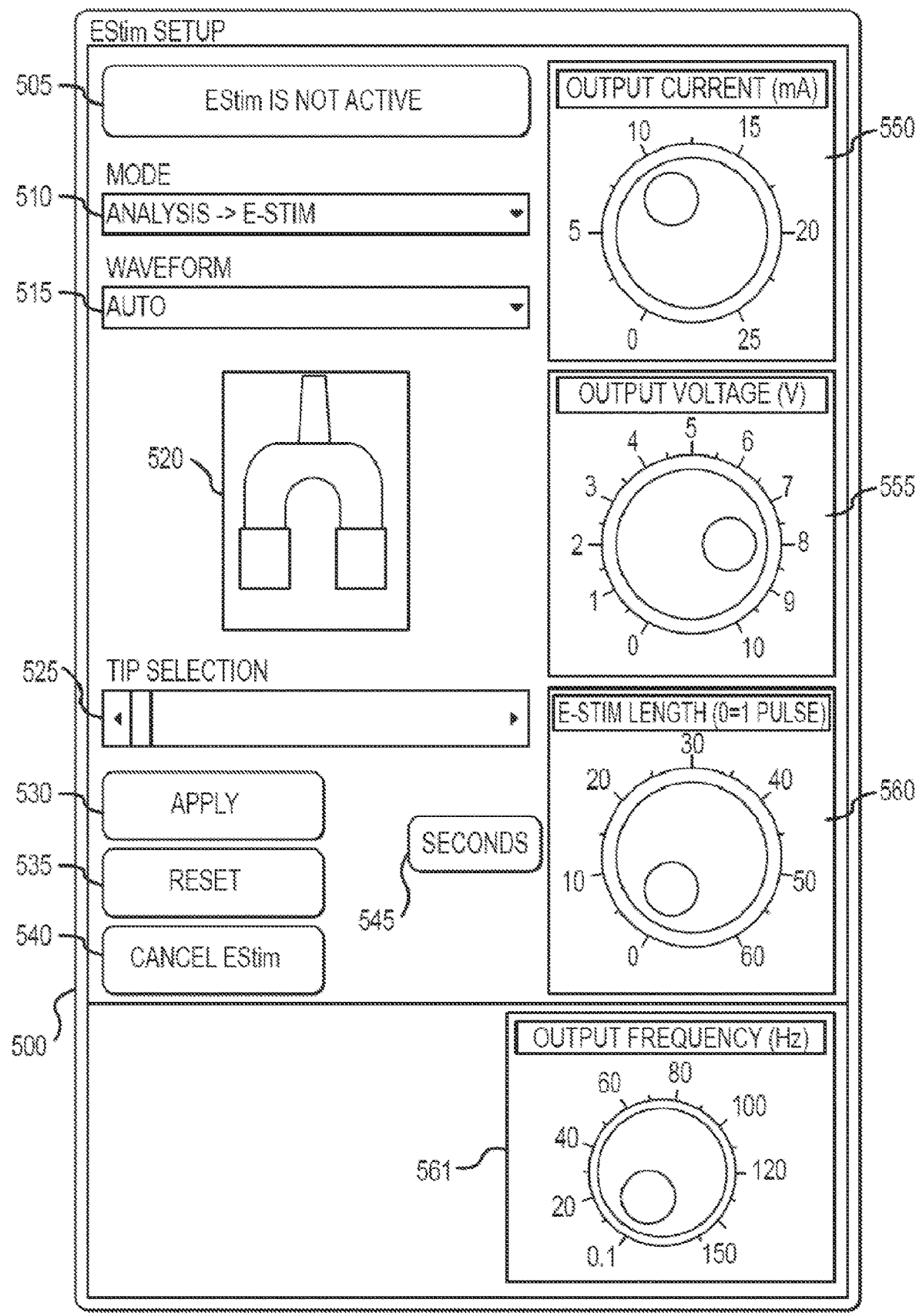
FIG. 20 illustrates an EStim setup display arrangement on the touch screen that may form part of the computer interface.

FIG. 20 illustrates an example of such an EStim setup display arrangement on the touch screen 500 of the monitor 36. The EStim setup display arrangement shown on the touch screen 500 includes an "EStim" status indicator 505, a mode button 510, a waveform button 515, a tip or probe-type indication 520, a tip or probe type selection button 525, an "Apply" button 530, a "Reset" button 535, a "Cancel EStim" button 540, a time button 545, an output current selector 550, an output voltage selector 555, an EStim length selector 560, and an Output Frequency selector 561. The EStim status indicator 505 conveys to the operator whether or not the electrical simulation capability of the system 1111 is active (e.g., ready for use) or not.

Figure 21:
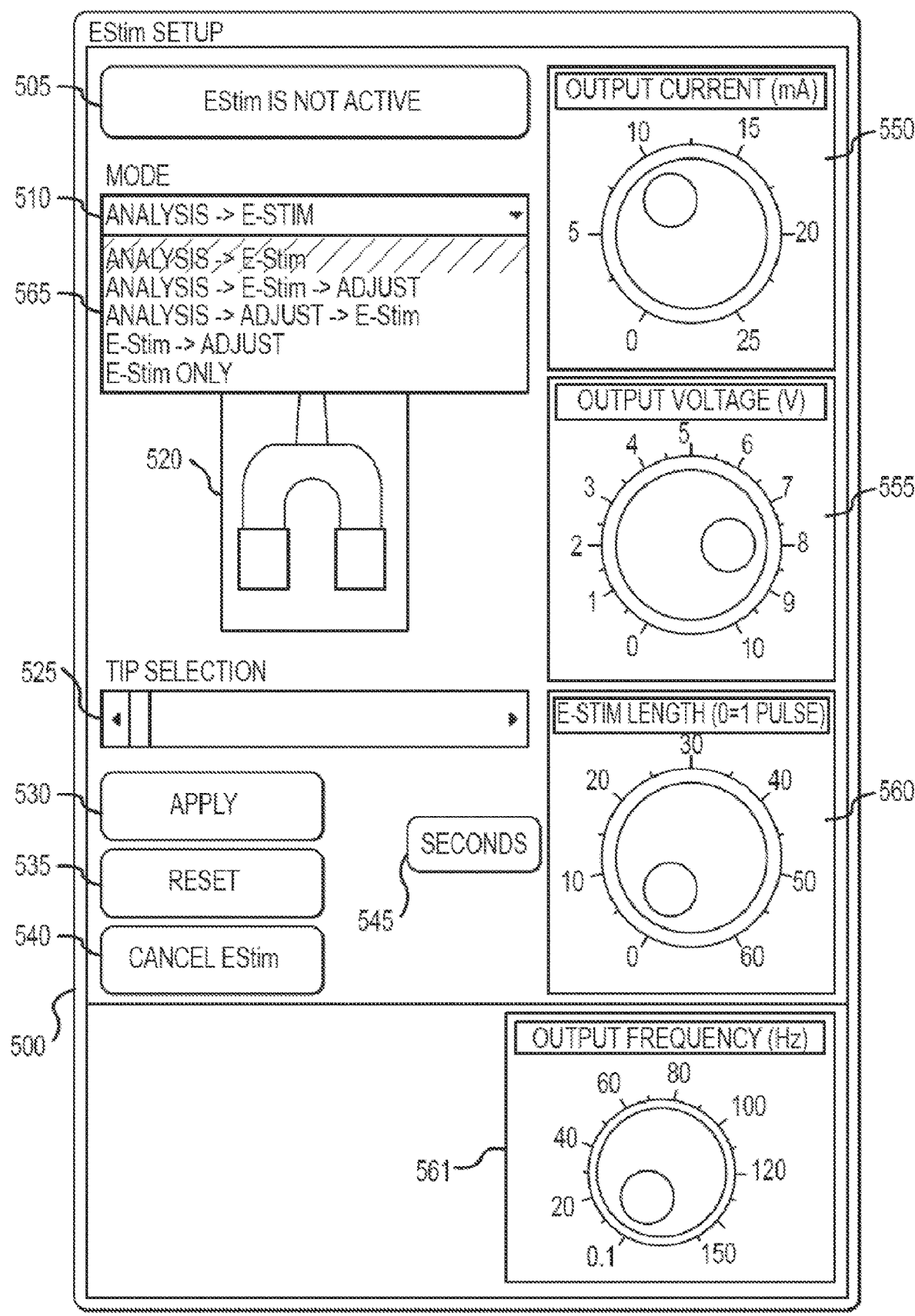
FIG. 21 is the same view as FIG. 20, except showing a pull down menu activated via the mode button.

The mode button 510 allows for the operator to select from a variety of operational modes. For example, as illustrated in FIG. 21, which is the same view as FIG. 20, except showing a pull down menu 565 activated via the mode button 510, in one embodiment, the selectable modes include: 1) analyze tissue impulse frequency and/or tissue response (e.g., galvanic response) followed by application of electrical stimulation to tissue (Analysis→EStim); 2) analyze tissue impulse frequency and/or tissue galvanic response followed by application of electrical stimulation to tissue followed by application of force impulse to tissue (Analysis→EStim→Adjust); 3) analyze tissue impulse frequency and/or tissue galvanic response followed by application of force impulse to tissue followed by application of electrical stimulation to tissue (Analysis→Adjust→EStim); 4) application of electrical stimulation to tissue followed by application of force impulse to tissue (EStim→Adjust); and 5) application of electrical stimulation to tissue (EStim only).

Figure 22:
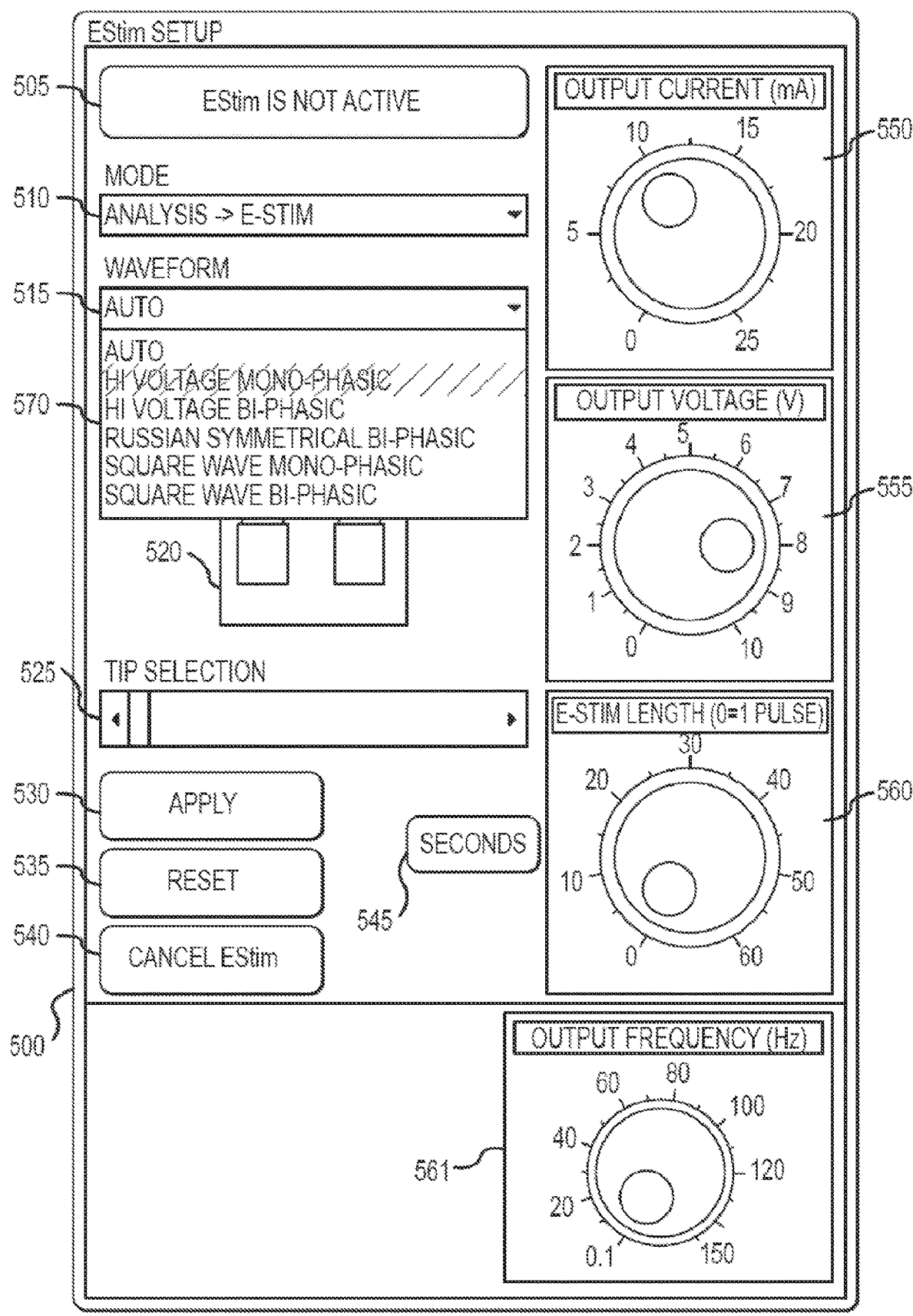
FIG. 22 is the same view as FIG. 20, except showing a pull down menu activated via the waveform button.

The waveform button 515 allows for the operator to select from a variety of waveforms for the electrical stimulation. For example, as illustrated in FIG. 22, which is the same view as FIG. 20, except showing a pull down menu 571 activated via the waveform button 515, in one embodiment, the selectable waveforms include: 1) auto, which allows the system to automatically select an appropriate waveform based off of the system's analysis of percussive impulse tissue readings and/or galvanic response tissue readings; 2) hi voltage mono-phasic; 3) hi voltage bi-phasic; 4) Russian symmetrical bi-phasic; 5) square wave mono-phasic; and 6) square wave bi-phasic.

The tip or probe type selection button 525 can be used to toggle the system 1111 between the variety of probe-types that can be employed with the system, as indicated in FIGS. 25A-25J, which illustrates a variety of types of probes 13 that are configured for interchangeable use with the system 1111 and are described in detail below. As can be understood from FIG. 20, the tip or probe-type indication 520 depicts a graphical representation of the probe-type selected via the probe type selection button 525.

The time button 545 can be used to set the duration of the electrical stimulation. In some embodiments, the time button 545 will also act as a display that displays the time remaining until the end of the electrical stimulation.

The output current selector 550 can be used to set the output current in a range of 0-25 mA. The initial current setting may depend on the probe-type selected via button 525, the waveform selected via button 515, and the treatment target location on the patient's body. In one embodiment, the current setting may be automatically set according to treatment parameters stored in the memory 37, the treatment parameters being specific to respective combinations of probe-type, waveform and treatment target location.

The output voltage selector 555 can be used to set the output voltage in a range of 0-10 V. The initial voltage setting may depend on the probe-type selected via button 525, the waveform selected via button 515, and the treatment target location on the patient's body. In one embodiment, the voltage setting may be automatically set according to treatment parameters stored in the memory 37, the treatment parameters being specific to respective combinations of probe-type, waveform and treatment target location.

The EStim length selector 560 can be used to set the electrical stimulation from 1-61 pulses over the duration selected via the time button 545, wherein a setting of zero equals a single pulse and a setting of 60 equals 61 pulses.

The Output Frequency selector 561 can be used to set the electrical stimulation from 0.1-150 Hz. The initial frequency setting may depend on the probe-type selected via button 525, the waveform selected via button 515, and the treatment target location on the patient's body. In one embodiment, the frequency setting may be automatically set according to treatment parameters stored in the memory 37, the treatment parameters being specific to respective combinations of probe-type, waveform and treatment target location.

Once all of the settings for the system 1111 are set via the setting controls 510, 515, 525, 550, 555, 560 and 561 as described above, the operator can actuate the "Apply" button 530 to cause the system 1111 to adopt the settings and cause the "EStim" status indicator 505 to change from "Not Active" to "Active" and the computer interface 40 to return to the treatment screen display. Actuating the "Apply" button 530 also causes the system 1111 to instruct the operator via the monitor 36 regarding any setup required for the system 1111 to function as needed for the adopted settings. For example, upon actuating the "Apply" button 530, the system 1111 may prompt the operator via the monitor 36 to couple a specific type of probe 13 and/or EStim pad 315 to the system 1111. Also, actuation of the "Apply" button 530 may cause the system 1111 via the monitor 36 to provide safety and/or treatment instructions to the operator.

The "Reset" button 535 can be actuated by the operator to reset the setting controls 510, 515, 525, 550, 555, 560 and 561 to modify the electrical stimulation to be provided via the system 1111.

As can be understood from FIG. 19, the operator can actuate the "Cancel EStim" button 540 shown in FIG. 20 [block 2015], which clears the electrical stimulation settings and deactivates the electrical stimulation [block 2020], thereby causing the "EStim" status indicator 505 to change from "Active" to "Not Active". The system 1111 then goes to the shockwave treatment mode [block 2025] shown in FIGS. 23 and 24.

Figure 23:
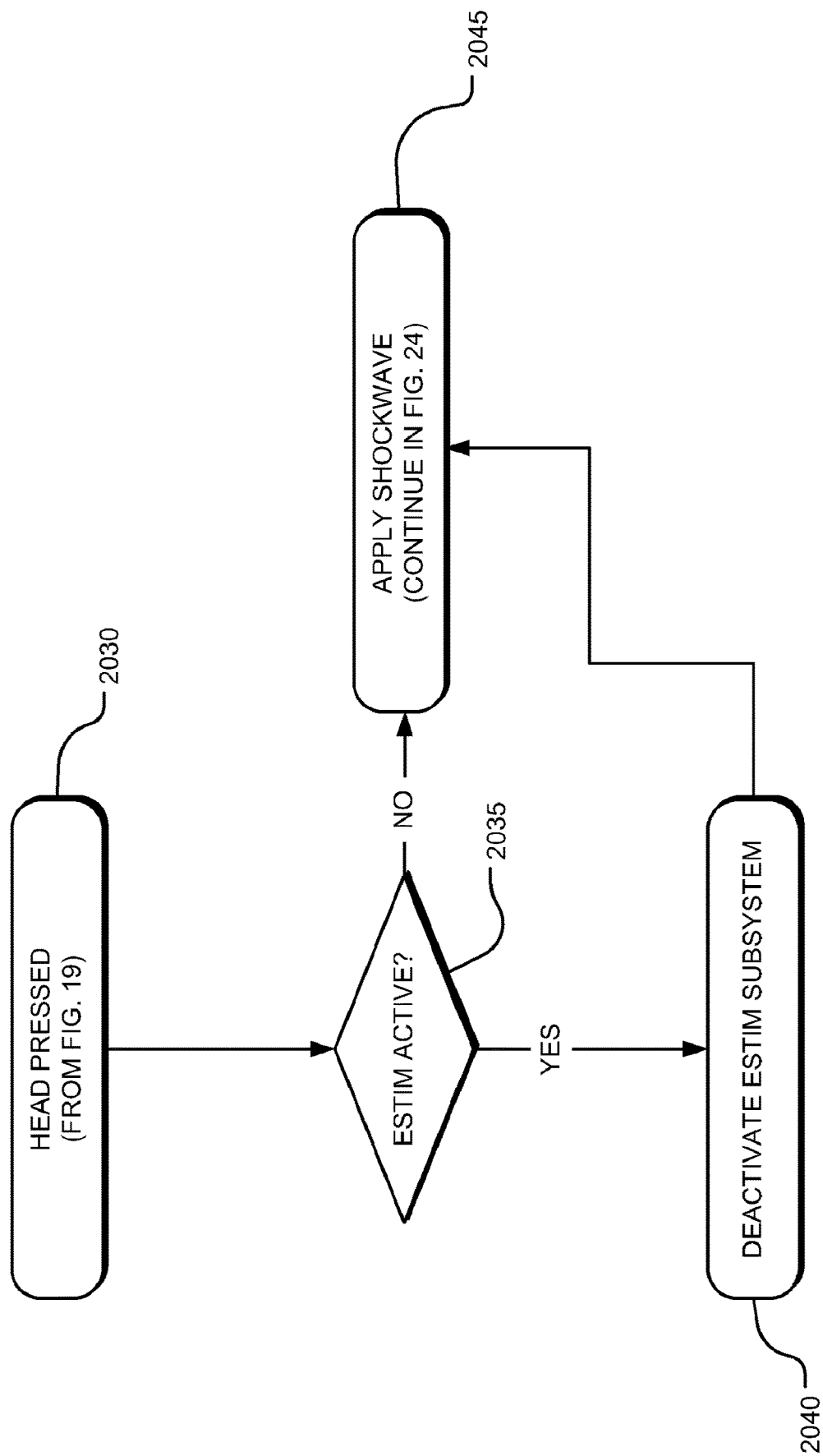
FIG. 23 is a method flow chart illustrating the continuation of the method illustrated in FIG. 19.
Figure 24:
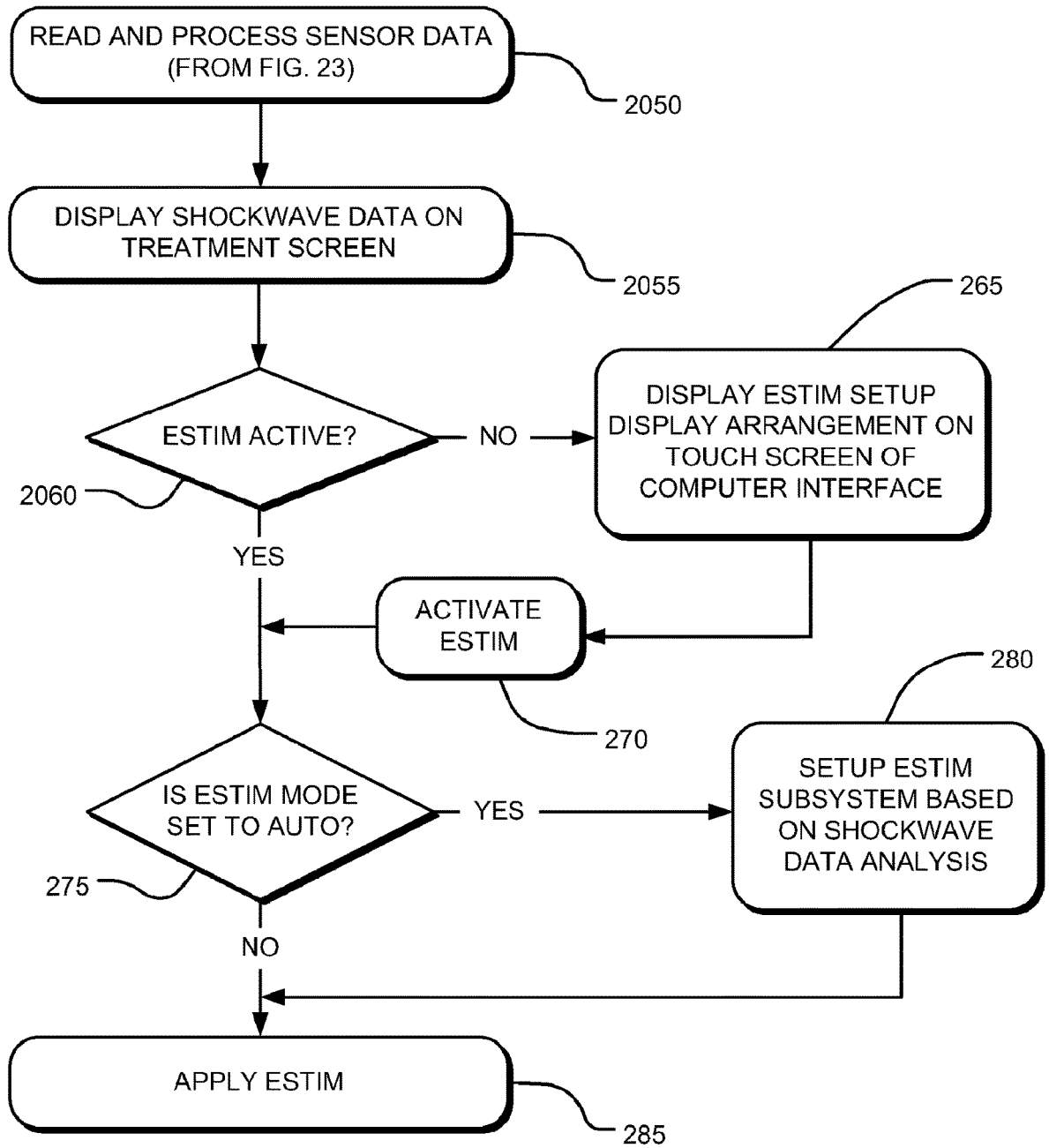
FIG. 24 is a method flow chart illustrating the continuation of the method illustrated in FIG. 23.

As can be understood from FIG. 19, if it is determined at block 2005 that the EStim is active, then the system 1111 deactivates the EStim subsystem [block 2020] and the system 1111 system transitions to the shockwave treatment mode [block 2025] shown in FIGS. 23 and 24.

As can be understood from FIG. 23, the tips 12 of the treatment head or probe 13 are pressed against the treatment target tissue of the patient until the preload threshold is met as discussed in detail above [2030]. The system 1111 does another check to see if the EStim is active [block 2035]. If the EStim is active, then the EStim subsystem is deactivated [block 2040], and the shockwave is then applied [block 2045]. If the EStim check of block 2035 shows that the EStim is already not active, then the shockwave is then applied [block 2045].

Continuing the process in FIG. 24, the target tissue frequency response is read via the piezoelectric sensor 11 and processed [block 2050]. Data pertaining to the target tissue frequency response to the shockwave is displayed on the monitor 34 or its treatment screen 500 [block 2055]. The system 1111 again checks to see if the EStim is active [block 2060] and, if not, then the EStim setup display arrangement (shown in FIG. 20) is displayed on the touch screen 500 of the monitor 36 [block 2065], thereby allowing the EStim settings to be set as described above and the EStim to be activated [block 2070].

As can be understood from FIG. 24, regardless of whether the check of block 2060 indicated that the EStim was already active or the EStim was activated at block 270, the system does a check to see if the EStim mode is set to auto [block 275]. If the EStim is not active, the system displays EStim setup display arrangement on touch screen of computer interface at block 265, and then the EStim is activated at block 270. If the EStim mode is set to auto, then the system 1111 applies the EStim according to the system's analysis of the shockwave data, applying EStim protocols and parameters as stored in the memory 37 and determined by the system 1111 to be appropriate for the target tissue based on the system's analysis of the shockwave data [block 280]. The auto EStim is then applied to the patient's treatment target tissue [block 285]. If the check of block 275 reveals the EStim mode is not set to auto, then the EStim is applied [block 285] and the EStim in this case will be applied per the protocols and parameters manually set via the EStim setup display arrangement (shown in FIG. 20) displayed on the touch screen 500 of the monitor 36.

As can be understood from FIGS. 25A-25J, a variety of different configurations of probes 13 can be employed with the therapy delivery head 44 of FIGS. 1, 2 and 13. For example, as illustrated in FIGS. 25A-25C and 25E-25G, the probe 13 can have a generally horseshoe-shaped body ending is two space-apart tips 12, which may be soft. A stem 570 extends from the opposite side of the body of the probe 13 from the tips 12, the stem 570 being used for coupling the probe 13 to the forward end 20 of the head 44 and the piezoelectric sensor 11 and anvil 9, as can be understood from FIG. 1. Each tip 12 may have an electrode 14 at the extreme end of the tip 12.

As indicated in FIGS. 25A-25C and 25G, some dual tipped probes 13 may have tips 12 that extend generally an even distance. As shown in FIGS. 25E and 25F, other dual tipped probes 13 may have tips 12 that do not extend an even distance.

As can be understood from FIGS. 25A-25C and 25E-25G, the dual tipped probes 13 may have tips 12 that are laterally spaced apart from each other a variety of distances W. For example, the dual tipped probes 13 of FIGS. 25A-25C and 25E-25G have respective tip spacing distances W of 3.2 cm, 4.7 cm, 2.2 cm, 3.2 cm, 3.2 cm and 9.8 cm. As can be understood from a comparison of FIGS. 25E and 25F, despite having the same spacing distances W of 3.2 cm, the dual tipped probe 13 of FIG. 25F has a greater difference in the extent of extension of its tips 12 relative to each other than is the case with the tips 12 of the probe of FIG. 25E.

As can be understood from FIGS. 25D and 25H-25J, some embodiments of the probe 13 may have a single tip 12. A stem 570 extends from the opposite side of the body of the probe 13 from the tip 12, the stem 570 being used for coupling the probe 13 to the forward end 20 of the head 44 and the piezoelectric sensor 11 and anvil 9, as can be understood from FIG. 1. The tip 12 may have an electrode 14 at the extreme end of the tip 12.

Figure 25A:
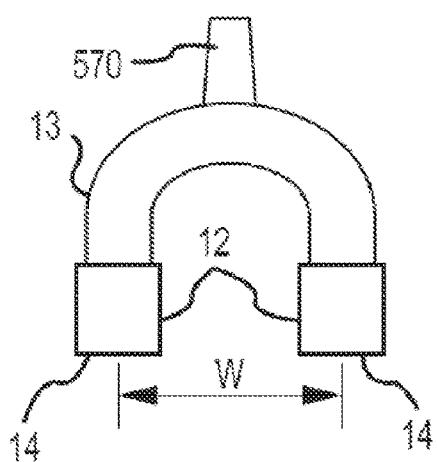
Figure 25B:
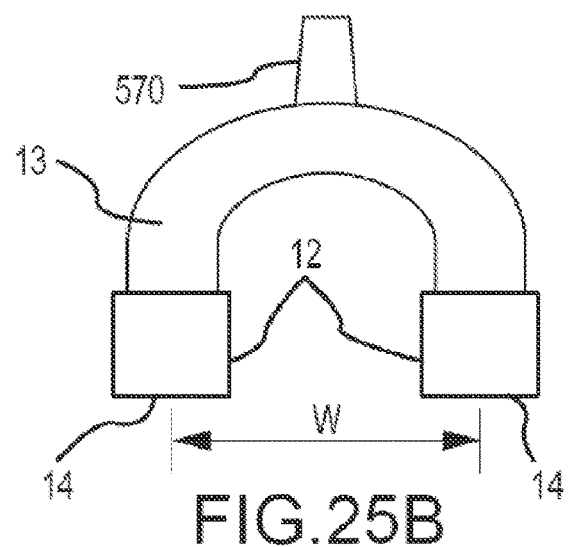
Figure 25C:
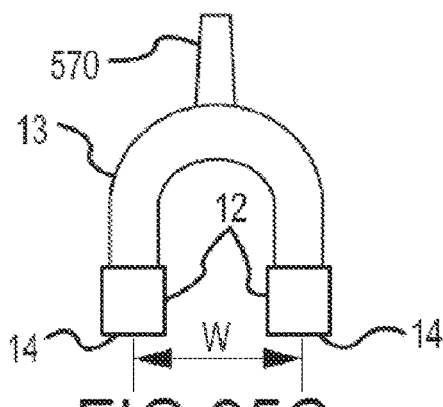
Figure 25D:
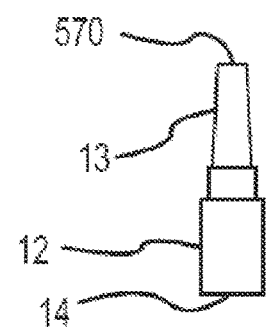
Figure 25E:
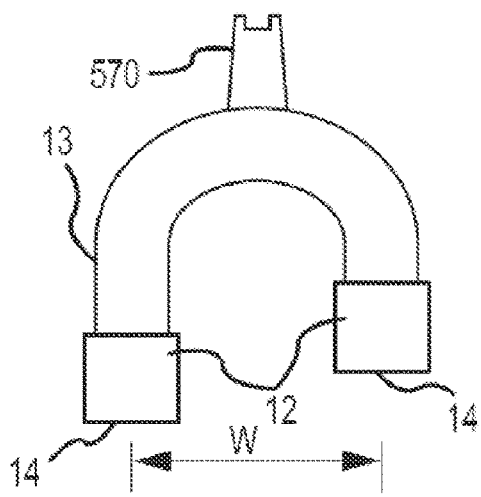
Figure 25F:
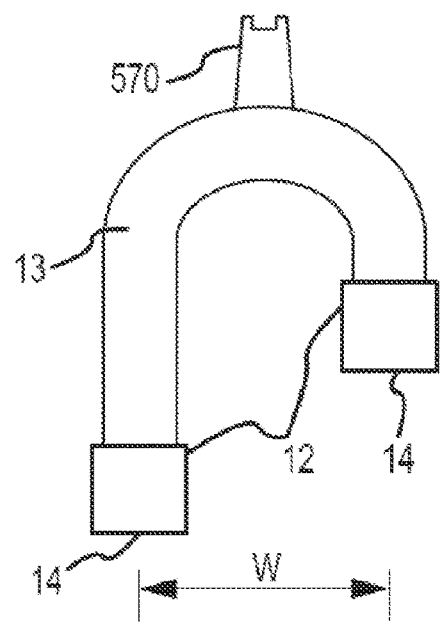

In some cases, as in FIG. 25D, the single tip 12 may be generally hemispherical in configuration. In other cases, as in FIGS. 25H-25J, the single tip 12 may be generally flat-ended in configuration.

As can be understood from FIGS. 25H-25J, the flat-ended tips 12 may have a variety of widths W. For example, the flat-ended tips 12 depicted in FIGS. 25H-25J have respective widths W of 4.5 cm, 3.2 cm, and 1.7 cm. Such flat-ended tips 12 may be formed of soft rubber.

In some instances, the probes 13 of FIGS. 25A-25D may be employed where the patient tissue that is the target of the treatment being provide via the system 1111 is adjacent the patient's vertebra. The probes 13 of FIGS. 25E-25G may be employed on specific anatomical features of the patient. The probes 13 of FIGS. 25H-25J may be employed where the tissue being treated is in close proximity to skeletal structures.

Figure 26:
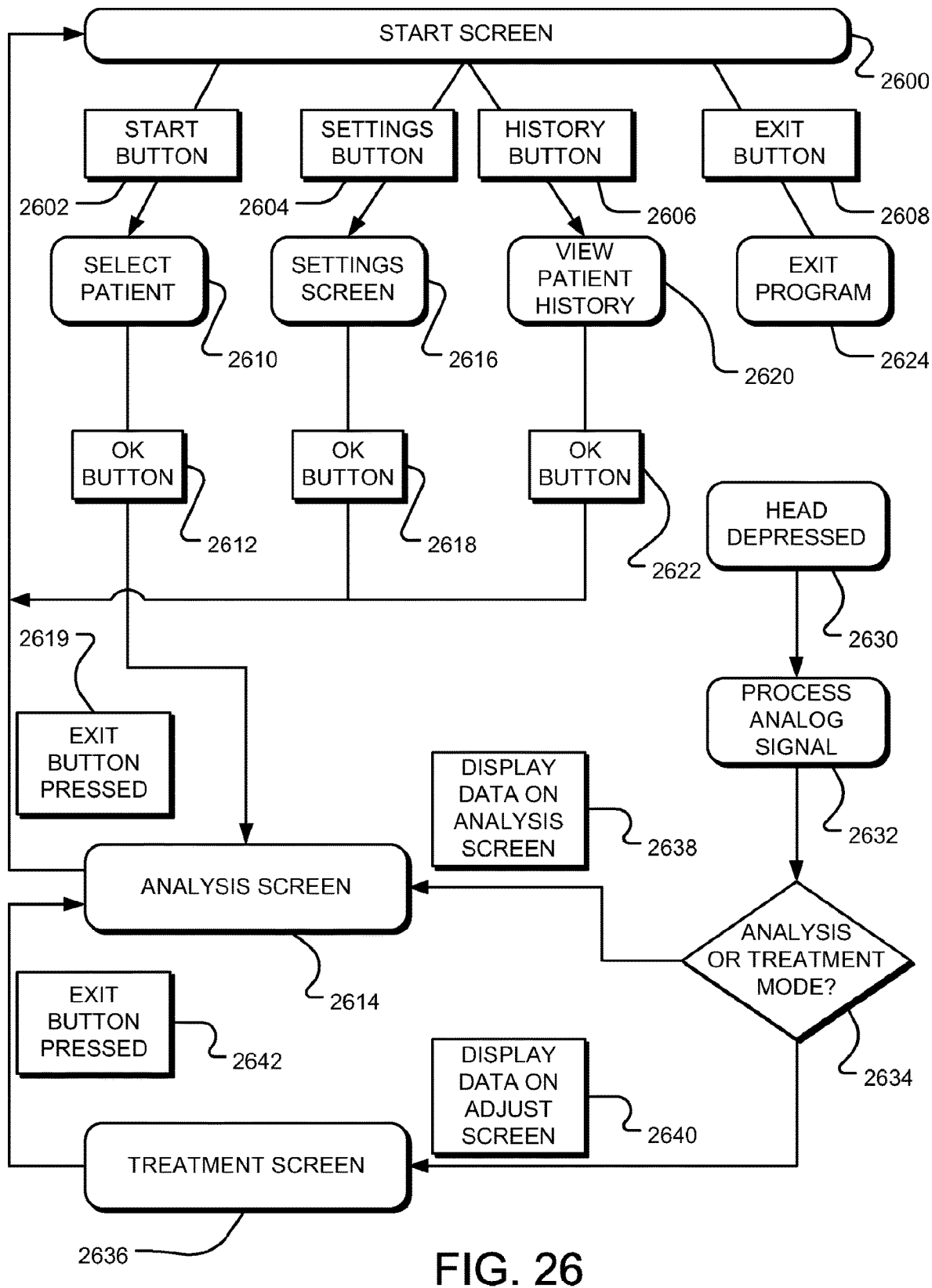
FIG. 26 is a flow chart illustrating another operational methodology for the system and its touch screen interface.

For a discussion of an alternative embodiment of the system of FIG. 13, reference is made to FIG. 26, which is a flow chart illustrating another operational methodology for the system 1111 and its touch screen interface 500. As shown in FIG. 26, a start screen 2600 may be displayed wherein the start screen 2600 displays a start button 2602, a settings button 2604, a history button 2606, and an exit button 2608. Upon pressing the start button 2602, the system 1111 enters a select patient mode 2610. As a result, where the patient currently being treated via the system 1111 is a patient previously treated via the system 1111, the select patient mode 2610 allows the operator of the system 1111 to select the patient's name to cause the patient's previously stored medical data and associated system operational settings to automatically load and be usable by the system 1111 for the current treatment of the patient. Alternatively, where the patient currently being treated via the system 1111 is a new patient never previously treated via the system 1111, the select patient mode 2610 allows the operator of the system 1111 to enter new patient's name and patient data for use by the system 1111 for the treatment of the new patient. Once the operator has selected the patient name or entered the name and data of a new patient, the operator can press the OK button 2612 to close out of the select patient mode 2610. The system 1111 then displays on the touch screen interface 500 the analysis screen 2614.

Upon pressing the settings button 2604, the system 1111 enters a settings screen mode 2616, which displays the system diagnostic/treatment settings currently set for the patient selected via the select patient mode 2610. The operator can adjust the system diagnostic/treatment settings via the settings screen mode 2616. The system diagnostic/treatment settings can be saved and the settings screen mode 2616 can be exited by pressing the OK button 2618. The system 1111 then displays on the touch screen interface 500 the start screen 2600, unless an exit button 2619 is pressed, thereby causing the system 1111 to display on the touch screen interface 500 the analysis screen 2614.

Upon pressing the history button 2606, the system 1111 enters a view patient history mode 2620, which displays the patient diagnostic/treatment history for the patient selected via the select patient mode 2610. Once the operator is done reviewing the patient history, the view patient history mode 2620 can be exited by pressing the OK button 2622. The system 1111 then displays on the touch screen interface 500 the start screen 2600, unless the exit button 2619 is pressed, thereby causing the system 1111 to display on the touch screen interface 500 the analysis screen 2614.

Upon pressing an exit button 2608 at the start screen 2600, an exit program mode 2624 will begin, thereby causing the system 1111 to automatically shut down.

Still referring to FIG. 26, it can be understood that the probe 13 of the treatment head 44 is depressed against the treatment target location on the patient [see 2630], which causes the system 1111 to process the resulting analog signal [see 2632]. As can be understood at 2634 in FIG. 26, depending on whether the system 1111 is in the analysis mode and the head depressing 2630 was for analysis purposes or the treatment mode and the head depressing 2630 was for treatment purposes, the system will display on the touch screen interface 500 the analysis screen 2614 or a treatment screen 2636. If the analysis screen 2614 is displayed, then the data from the processed analog signal [see 2632] will be displayed on the analysis screen [see 2638]. If the treatment screen 2636 is displayed, then the data from the processed analog signal [see 2632] will be displayed on the treatment screen [see 2640] and, a following press of the exit button 2642 will the system to then transition to the analysis screen 2614.

Figure 27:
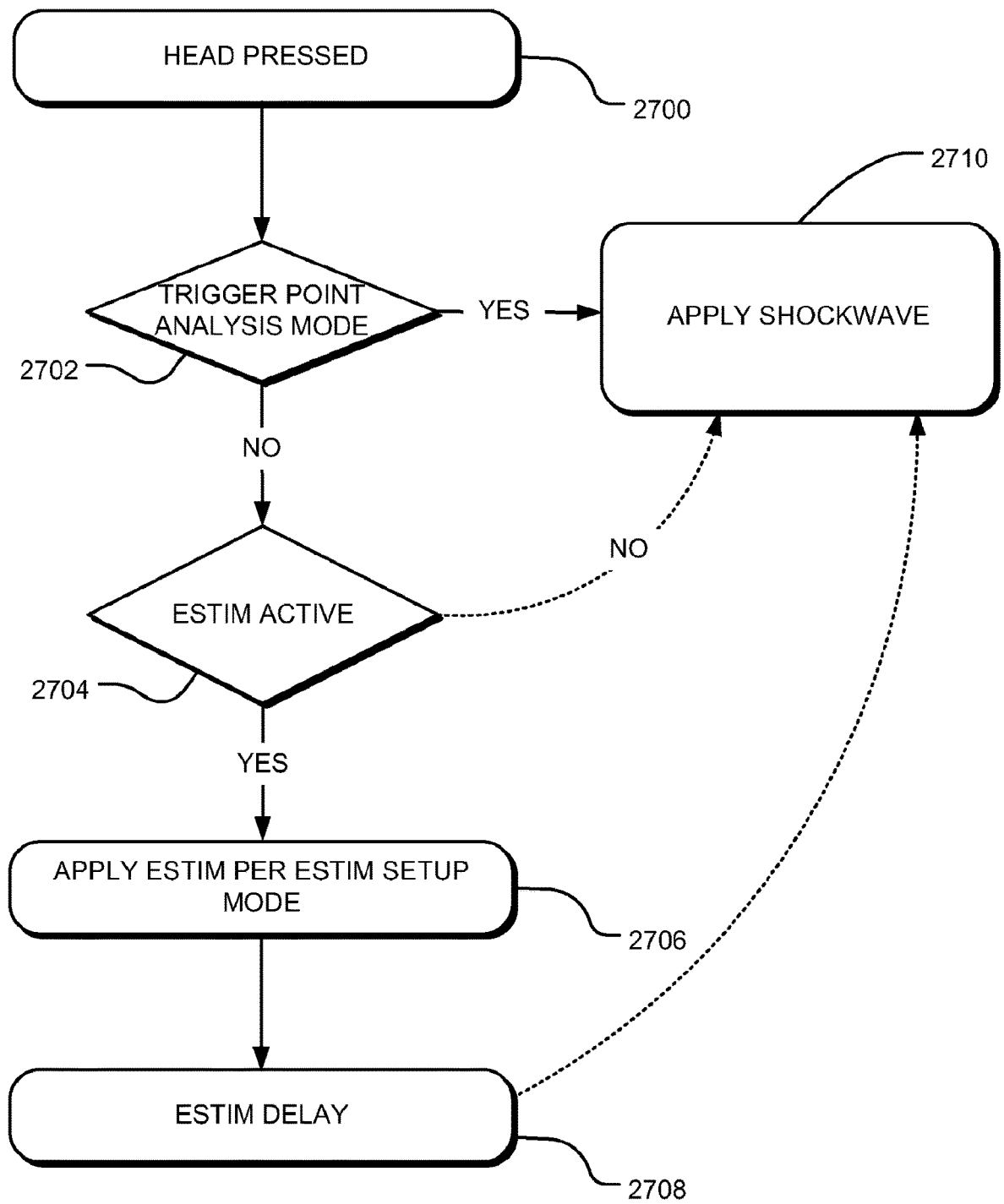
FIG. 27 is a flow chart for a treatment screen when the treatment head is pressed against the patient and the preload threshold is met.

When the treatment screen 2636 of FIG. 26 is displayed, the system 1111 is in a treatment mode and can be caused to function as depicted in FIG. 27. As shown in FIG. 27, if the probe 13 of the treatment head 44 is pressed against the patient [see 2700] and the preload threshold has been met, the system 1111 will determine if the system 1111 is in a trigger point analysis mode [see 2702]. The trigger point analysis is used to perform a single point analysis to determine the characteristics (e.g., frequency, amplitude and/or wave shape) that trigger or treatment point. If the system 1111 is not in the trigger point analysis mode, then the system 1111 will determine if the EStim is active [see 2704] and, if yes, then the system will apply the EStim per the EStim setup mode [see 2706], but the EStim will be delayed [see 2708] to be applied with the shockwave [see 2710]. If the trigger point analysis mode 2702 is on, then the shockwave is applied [see 2710].

Figure 28:
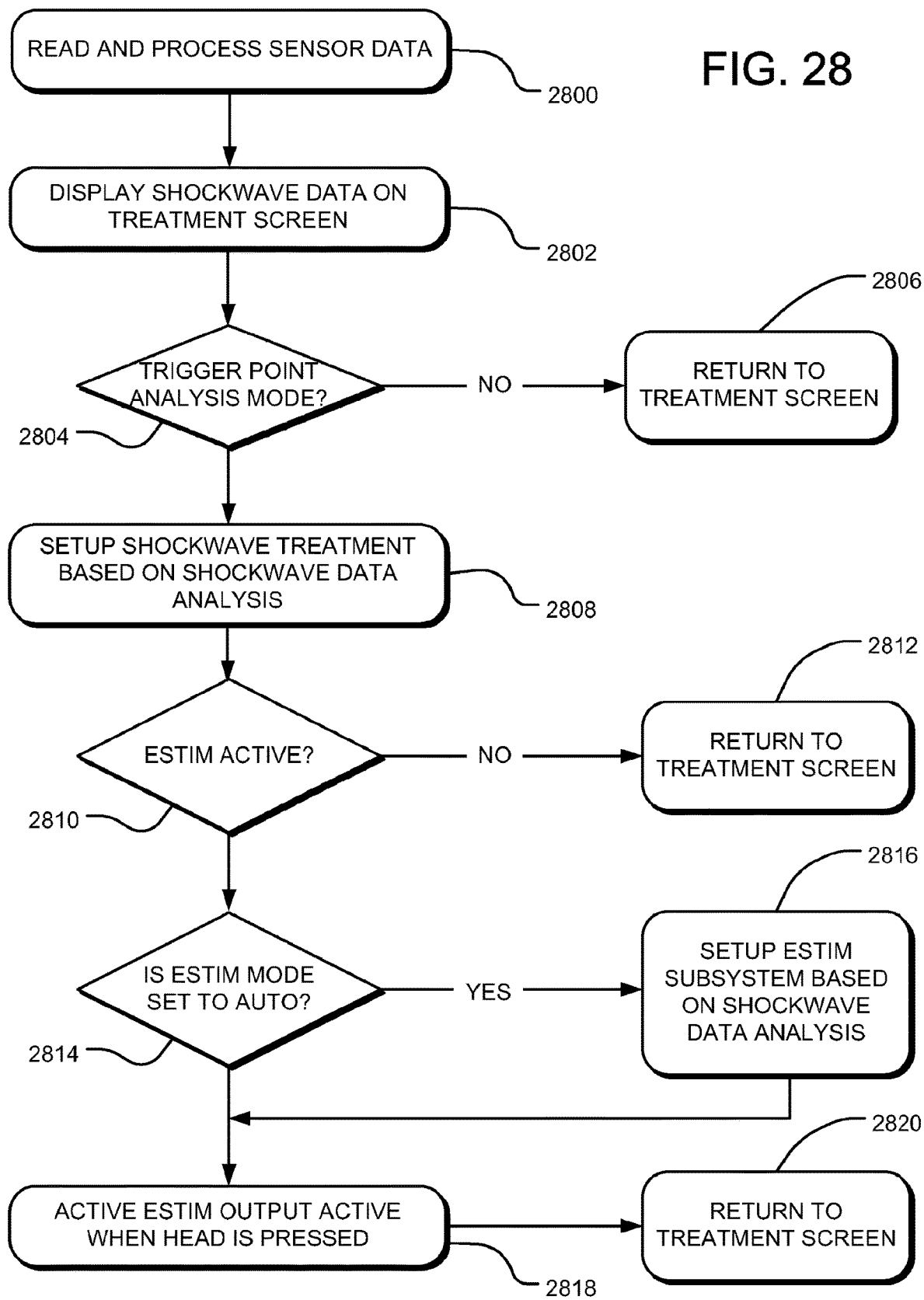
FIG. 28 is a flow chart illustrating a shockwave subsystem data event.

When the shockwave is applied as noted at 2710 in FIG. 27, a shockwave subsystem data event may take place as now explained with respect to FIG. 28. Specifically, sensor data is read and processed [see 2800], and the shockwave data is displayed on the treatment screen [see 2802]. The system determines if the trigger point analysis mode is active [see 2804] and, if not, the system 1111 returns to the treatment screen [see 2806]. If the trigger point analysis mode [see 2804] is active, then system 1111 sets up the shockwave treatment based on the shockwave data analysis [see 2808]. The system 1111 determines if the EStim is active [see 2810] and, if no, then the system returns to the treatment screen [see 2812]. If the EStim is active [see 2810], then the system 1111 determines if the EStim mode is set to auto [see 2814] and, if yes, then the EStim subsystem is set up based on the shockwave data analysis [see 2816]. If the EStim mode is set to auto [see 2814] or the EStim subsystem has already been based on the shockwave analysis [see 2816], then the EStim output is activated when the probe 13 of the treatment head 44 is pressed against the patient [see 2818] followed by a return to the treatment screen [see 2820].

Figure 29:
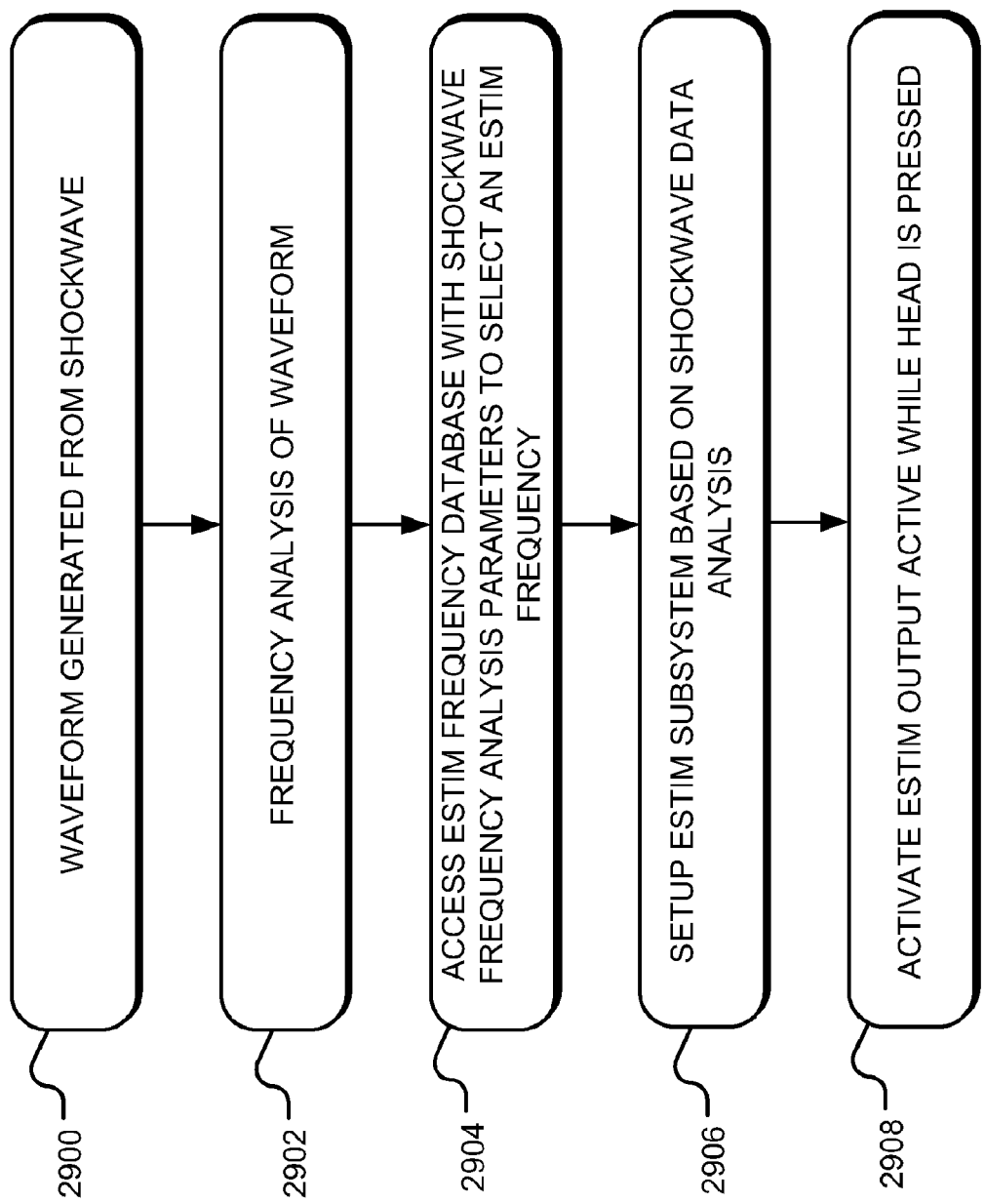
FIG. 29 is a flow chart illustrating an embodiment of the methodology of setting up the Estim subsystem based on a shockwave data analysis.

As can be understood from FIG. 29, in one embodiment, the EStim subsystem can be setup based on a shockwave data analysis. Specifically, a waveform is generated from the shockwave administered via the treatment head 44 [see 2900]. The system 1111 performs an analysis of a characteristic of the waveform [see 2902]. For example, the system analyzes the frequency of the waveform. The resulting shockwave frequency analysis parameters are used in accessing the EStim frequency database to select an EStim frequency [see 2904]. The EStim frequency database may include EStim frequencies and various associated setup parameters appropriate for a specific ranges of EStim frequencies. The EStim subsystem is setup based on the shockwave data analysis [see 2906]. The EStim output is caused to activate when the probe 13 of the treatment head 44 is pressed against the patient [see 2908]. While the embodiment discussed with respect to FIG. 29 is given in the context of the analyzed characteristic of the waveform being the frequency of the waveform, in other cases the analyzed characteristic of the shockwave waveform may be its amplitude, wave shape, or anyone or more of its frequency, amplitude or wave shape.

Thus, as can be understood from FIGS. 13 and 29, in one embodiment, the system 1111 disclosed herein is for treating the soft tissue of a patient. The system includes a treatment head 44 and a computer portion 45. The treatment head 44 includes a probe 13 and an electrode 14 operably coupled to the probe. The probe and electrode are configured to respectively deliver a mechanical force impulse and an electrical stimulation to the soft tissue when placed in operable contact with the soft tissue. The computer includes a CPU 34 and is configured to coordinate the delivery of the mechanical force impulse and electrical stimulation relative to each other. The system 1111 is configured to sense a shockwave in the soft tissue of the patient, the shockwave resulting from the mechanical force impulse delivered to the soft tissue via the probe. The system 1111 is also configured to analyze a characteristic of the sensed shockwave and configure the electrical stimulation to be delivered to the soft tissue via the electrode based on the characteristic analysis of the sensed shockwave, the characteristic analyzed being at least one of the frequency, amplitude or waveform of the sensed shockwave.

While the system 1111 may be configured to self-prescribe an electrical stimulation protocol based off of an analysis of a characteristic of the sensed shockwave as discussed above with respect to FIGS. 13, 15, 16 and 29, in other embodiments, the system may be configured to self-prescribe an electrical stimulation protocol based off of an identification of a patient affliction and inputting the identified patient affliction into the system 1111 to allow the system to access a database wherein specific electrical stimulation treatment protocols are referenced to specific affliction diagnoses.

Figure 30:
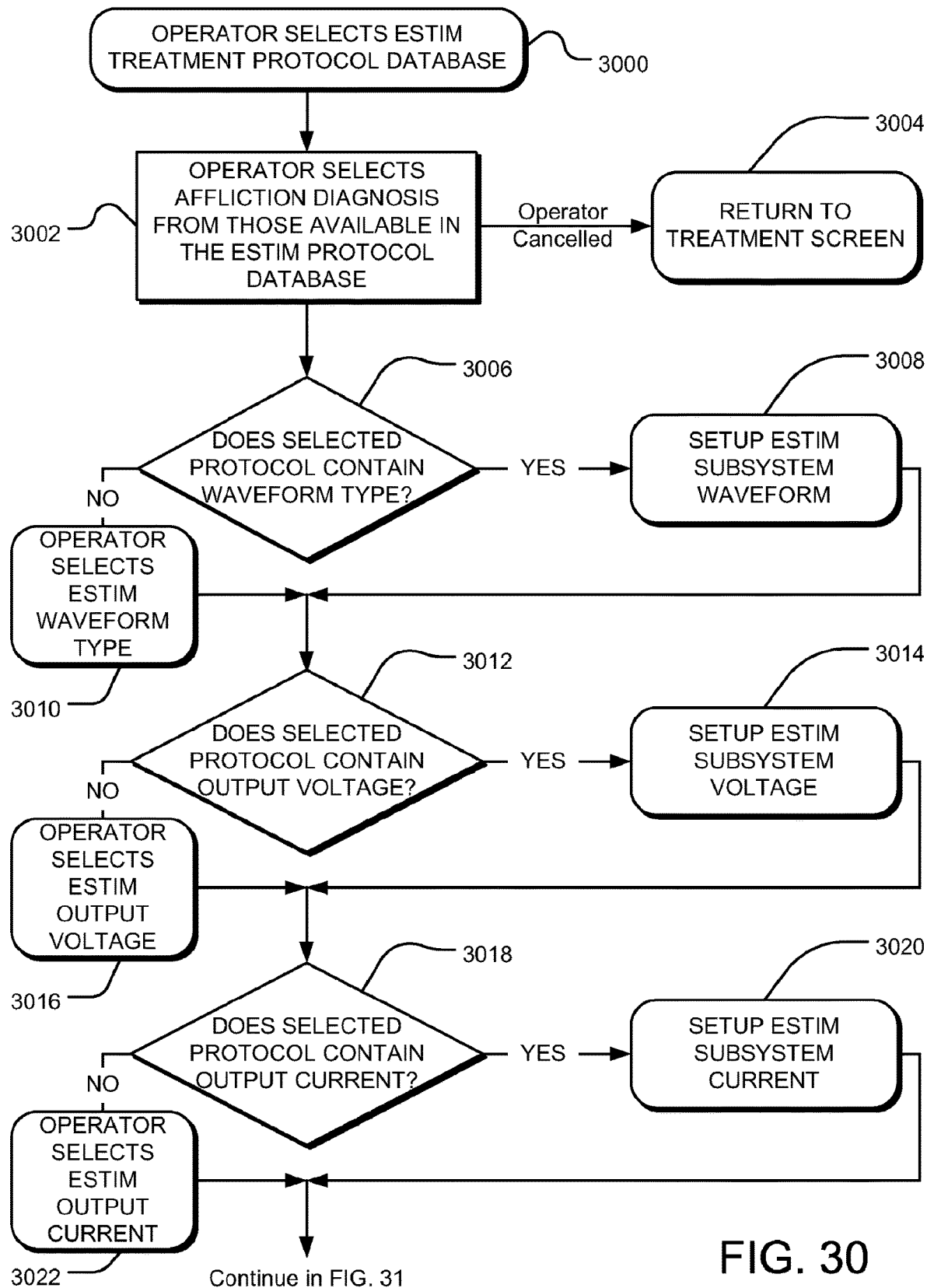
FIGS. 30-32 illustrate the EStim setup wherein an affliction diagnosis is used to select an EStim treatment protocol from an EStim treatment protocol database.
Figure 33:
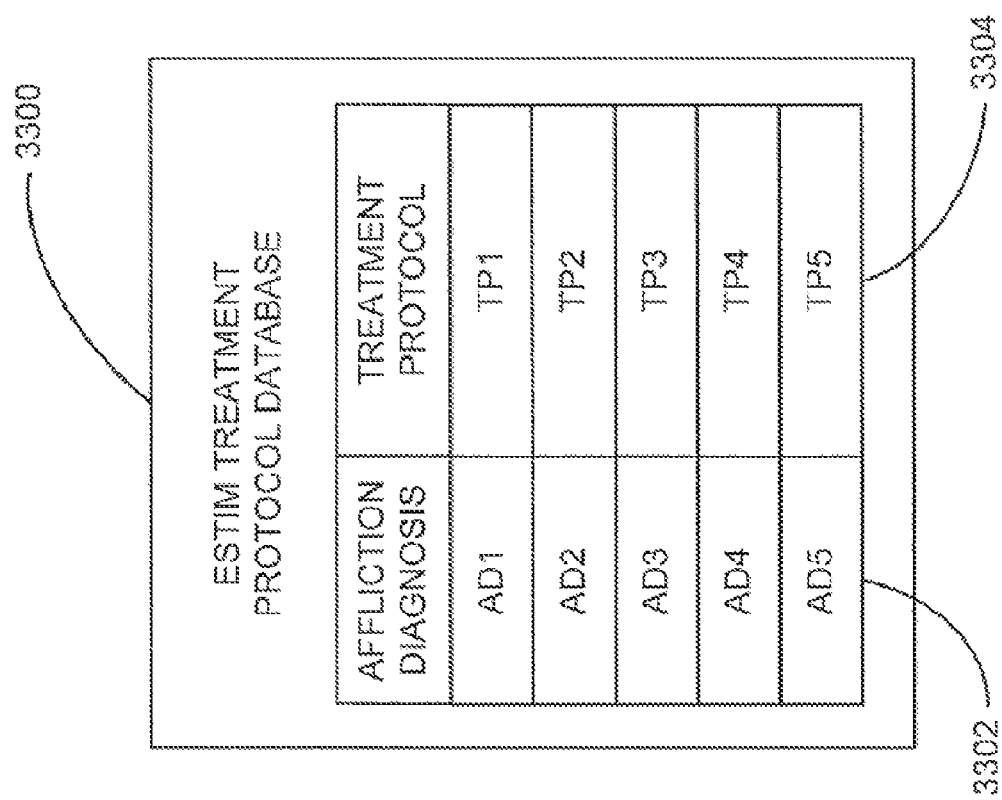
FIG. 33 illustrates an EStim treatment protocol database wherein specific affliction diagnoses are referenced to specific EStim protocols.

For example, as can be understood from FIG. 13 and the flow chart beginning in FIG. 30, a medical professional, who is the operator of the system 1111, uses the touch screen 500 to select an EStim treatment protocol database [see 3000]. The operator diagnoses the patient via, for example, reference to the patient's medical records, physical observation, and/or medical tests and diagnostics. Once diagnosing the patient's affliction, the operator uses the touch screen 500 to select an affliction diagnosis from those available in the EStim protocol database 3300, which is depicted in FIG. 33 [see 3002]. The EStim protocol database 3300 may have a number of common affliction diagnoses 3302 that are each referenced to a respective individually tailored treatment protocol 3304. For example, if the patient's diagnosis corresponds to affliction diagnosis AD2, then the operator selects affliction diagnosis AD2 and the system 1111 loads corresponding treatment protocol TP2 for administration to the patient. Examples of affliction diagnoses 3302 that may have respective predefined treatment protocols 3304 stored in the database 3300 include muscular dystrophy, multiple sclerosis, muscle atrophy due to stroke or paralysis, pre-operative surgical preparation, post-operative surgical recovery or physical therapy, discopathy, or etc.

Thus, the memory 37 includes an electrical stimulation protocol database 3300 containing multiple treatment protocols 3304 referenced to respective multiple affliction diagnoses 3302. In other words, each of the treatment protocols TP1-TP5 of the multiple treatment protocols 3304 may be referenced to a respective affliction diagnosis AD1-AD5 of the multiple affliction diagnoses 3302. Each such affliction diagnosis AD1-AD5 of the multiple affliction diagnoses 3302 may have a treatment protocol TP1-TP5 with electrical characteristics that are unique as compared to the electrical characteristics of the other treatment protocols TP1-TP5 of the multiple treatment protocols 3304.

If the operator cancels out of the selection of the affliction diagnosis at 3002, then the system 1111 returns to the treatment screen [see 3004]. However, if the operator does make a selection of a specific affliction diagnosis AD1-AD5 of the multiple available affliction diagnoses 3302 available in the database 3300 as indicated at 3002, then the system 1111 loads the specific corresponding treatment protocol TP1-TP5 out the multiple treatment protocols 3304 available in the database 3300. The system 1111 then looks to see if the loaded treatment protocol has a defined waveform type [see 3006], and, if so, the system sets the EStim up for the waveform [see 3008]. If not, then the system prompts the operator to select a waveform types [see 3010]. Such a prompting may give directions to the operator on suggested waveforms that might be appropriate based on desired outcome, perceived patient issues or needs, etc.

The system 1111 then looks to see if the loaded treatment protocol has a defined output voltage [see 3012], and, if so, the system sets the EStim up for the output voltage [see 3014]. If not, then the system prompts the operator to select an output voltage [see 3016]. Such a prompting may give directions to the operator on suggested voltages that might be appropriate based on desired outcome, perceived patient issues or needs, etc.

The system 1111 then looks to see if the loaded treatment protocol has a defined output current [see 3018], and, if so, the system sets the EStim up for the output current [see 3020]. If not, then the system prompts the operator to select an output current [see 3022]. Such a prompting may give directions to the operator on suggested currents that might be appropriate based on desired outcome, perceived patient issues or needs, etc.

Figure 31:
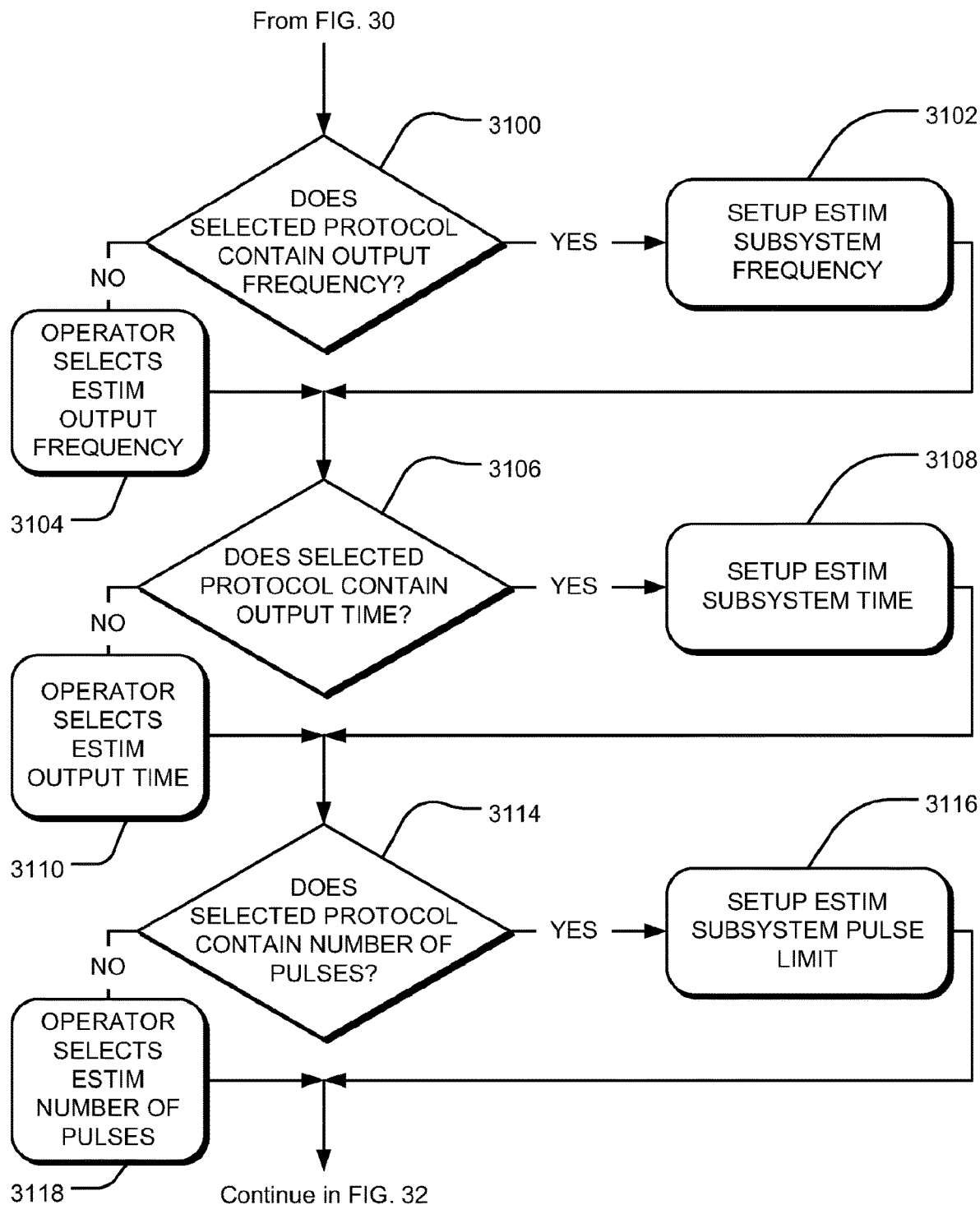

As continued in FIG. 31, the system 1111 then looks to see if the loaded treatment protocol has a defined output frequency [see 3100], and, if so, the system sets the EStim up for the output frequency [see 3102]. If not, then the system prompts the operator to select an output frequency [see 3104]. Such a prompting may give directions to the operator on suggested frequencies that might be appropriate based on desired outcome, perceived patient issues or needs, etc.

The system 1111 then looks to see if the loaded treatment protocol has a defined output time [see 3106], and, if so, the system sets the EStim up for the output time [see 3108]. If not, then the system prompts the operator to select an output time [see 3110]. Such a prompting may give directions to the operator on suggested output times that might be appropriate based on desired outcome, perceived patient issues or needs, etc.

The system 1111 then looks to see if the loaded treatment protocol has a defined number of pulses [see 3114], and, if so, the system sets the EStim up for the number of pulses [see 3116]. If not, then the system prompts the operator to select a number of pulses [see 3118]. Such a prompting may give directions to the operator on suggested number of pulses that might be appropriate based on desired outcome, perceived patient issues or needs, etc.

Figure 32:
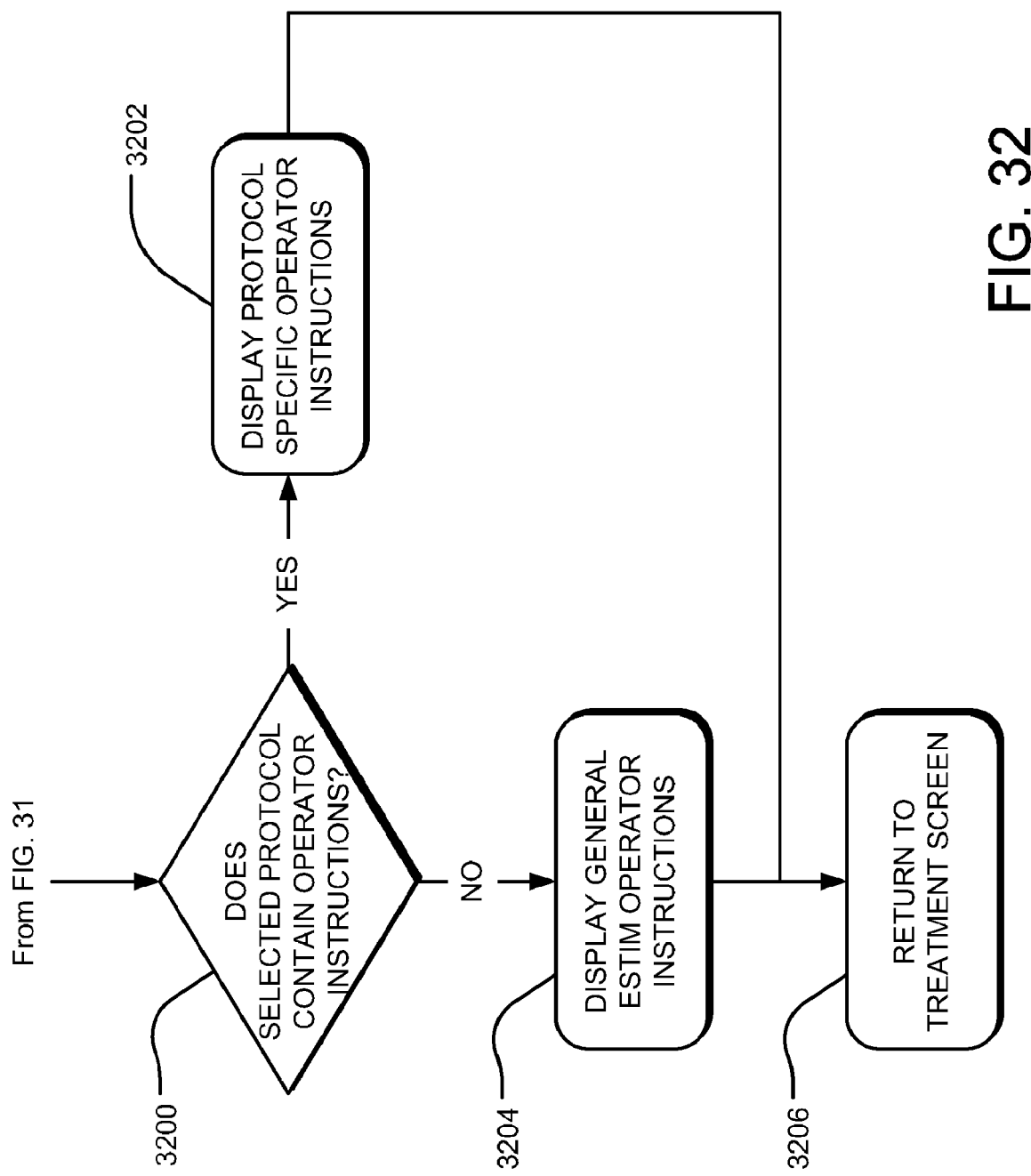

As continued in FIG. 32, the system 1111 then looks to see if the loaded treatment protocol has defined operator instructions [see 3200], and, if so, the system displays those instructions to the operator on the monitor 36 [see 3202], or if not, the system displays general ESTIM operator instructions [see 3204]. Such instructions may include electrode placement on the patient, where to place probes on the patient, patient preparations, system settings, etc. If not, then the displays general EStim operator instructions that are similar to those provided in 3202, but not specific to the selected treatment protocol [see 3104]. The system 1111 then returns to the treatment screen 3206.

Preoperative and Postoperative Treatment Via System Disclosed Herein

In one embodiment, the system 1111 disclosed herein and depicted in FIGS. 1 and 2 may be employed for preoperative and postoperative treatment ("PAPT") of tissue associated with a surgical site. The system 1111 is configured to guide the operator through pre-operative and post-operative treatments of patient tissue associated with one or more surgeries associated with one or more anatomical landmarks in accordance with selected treatment protocols. In this aspect, PAPT protocols allow the system 1111 to apply percussive impacts to tissues using the impulse stimulator instrument 44, those tissues, whether hard soft and/or hard tissues being associated with the preparation and/or recovery of the patient tissue impacted by a surgical procedure. Other PAPT protocols may additionally or exclusively include electrical stimulation applied to hard and/or soft tissues in associated with the surgical site. The electrical stimulation may be in the form of electrical stimulation protocols described above.

The PAPT protocols implemented by the system 1111 can break up and prevent tissue adhesions and fixations and reduce pain and inflammation following surgical procedures such as, for example, arthroplasty of the hip, knee and shoulder. Further, PAPT protocols implemented by the system 1111 can increase and improve tissue blood flow, lymphatic drainage, osteogenic activity, range of motion ("ROM"), muscle strength, and joint kinesis and function. Also, the PAPT protocols implemented by the system 1111 can reset muscle spindle fibers and stimulate neural pathways (i.e., nerve root and receptors).

I. Tissue Treatment Application

Figure 34:
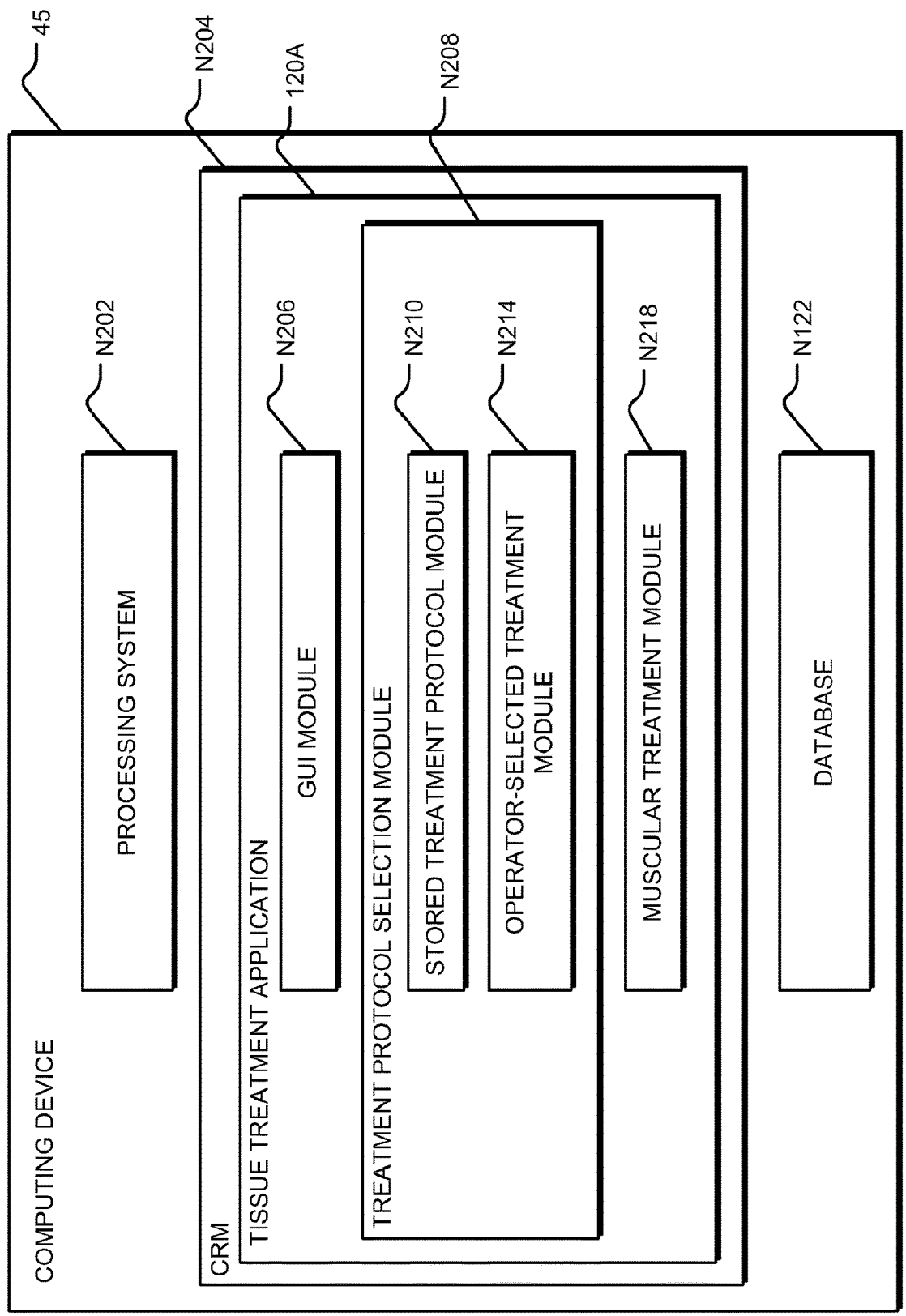
FIG. 34 is a block diagram of a preoperative and post-operative treatment ("PAPT") application configured to operate on a computing device.

FIG. 34 is a block diagram depicting a preoperative and postoperative treatment tissue treatment application N120A executing on the data acquisition circuitry 45 and the software code 38 depicted in FIG. 2. According to one aspect, the computing device 45 of FIG. 34 includes a processing system N202 that includes one or more processors or other processing devices. The processing system N202 executes the preoperative and postoperative treatment tissue treatment application N120A to select and provide a treatment of the tissues of a patient associated with a surgical site using the impulse stimulator instrument 44 with or without the available electrical stimulation. A database N122 may be accessed by the tissue treatment application N120A during execution to provide information including, but not limited to: stored patient information, stored treatment protocols, and stored instrument control settings.

In an aspect, the computing device 45 includes a computer readable medium ("CRM") N204 configured with the tissue treatment application N120A. The tissue treatment application N120A includes instructions or modules that are executable by the processing system N202 to enable a user to implement a treatment to the tissues of a patient.

The CRM N204 may include volatile media, nonvolatile media, removable media, non-removable media, and/or another available medium that can be accessed by the computing device 45. By way of example and not limitation, computer readable medium N204 comprises computer storage media and communication media. Computer storage media includes nontransient memory, volatile media, nonvolatile media, removable media, and/or non-removable media implemented in a method or technology for storage of information, such as computer readable instructions, data structures, program modules, or other data. Communication media may embody computer readable instructions, data structures, program modules, or other data and include an information delivery media or system.

A GUI module N206 transmits one or more GUIs to the display. The operator of the system 1111 interacts with one or more GUIs received from the computing device 45 to review treatment protocols, enter data and make menu selections used to implement a treatment using the system 1111. Examples of screen shots of the one or more GUIs in various aspects are provided herein below.

In an aspect, the tissue treatment application N120A includes a treatment protocol selection module N208 for selecting an appropriate treatment protocol based on stored patient data, analysis of the patient's tissues, selection from a stored menu of treatment protocols, and/or specification of a treatment protocol by the operator of the system 1111. The tissue treatment application N120A may further include modules to implement a particular treatment on the tissues of a patient, such modules including, for example, a preoperative and postoperative treatment ("PAPT") module N218. A detailed description of the PAPT module N218 is provided herein below.

II. Treatment Protocol Selection Module

The treatment protocol selection module N208 selects one or more treatment protocols to be performed on the tissues of a patient. The one or more treatment protocols may be selected from a stored menu of treatment protocols, a treatment protocol may be determined based on an assessment of the condition of the patient's tissues, or a treatment protocol may be specified by the operator of the system 1111. The treatment protocol selection module N208 in an embodiment may include a stored treatment protocol module N210, and an operator-selected treatment module N214.

a. Stored Treatment Protocol Module

Figure 35:
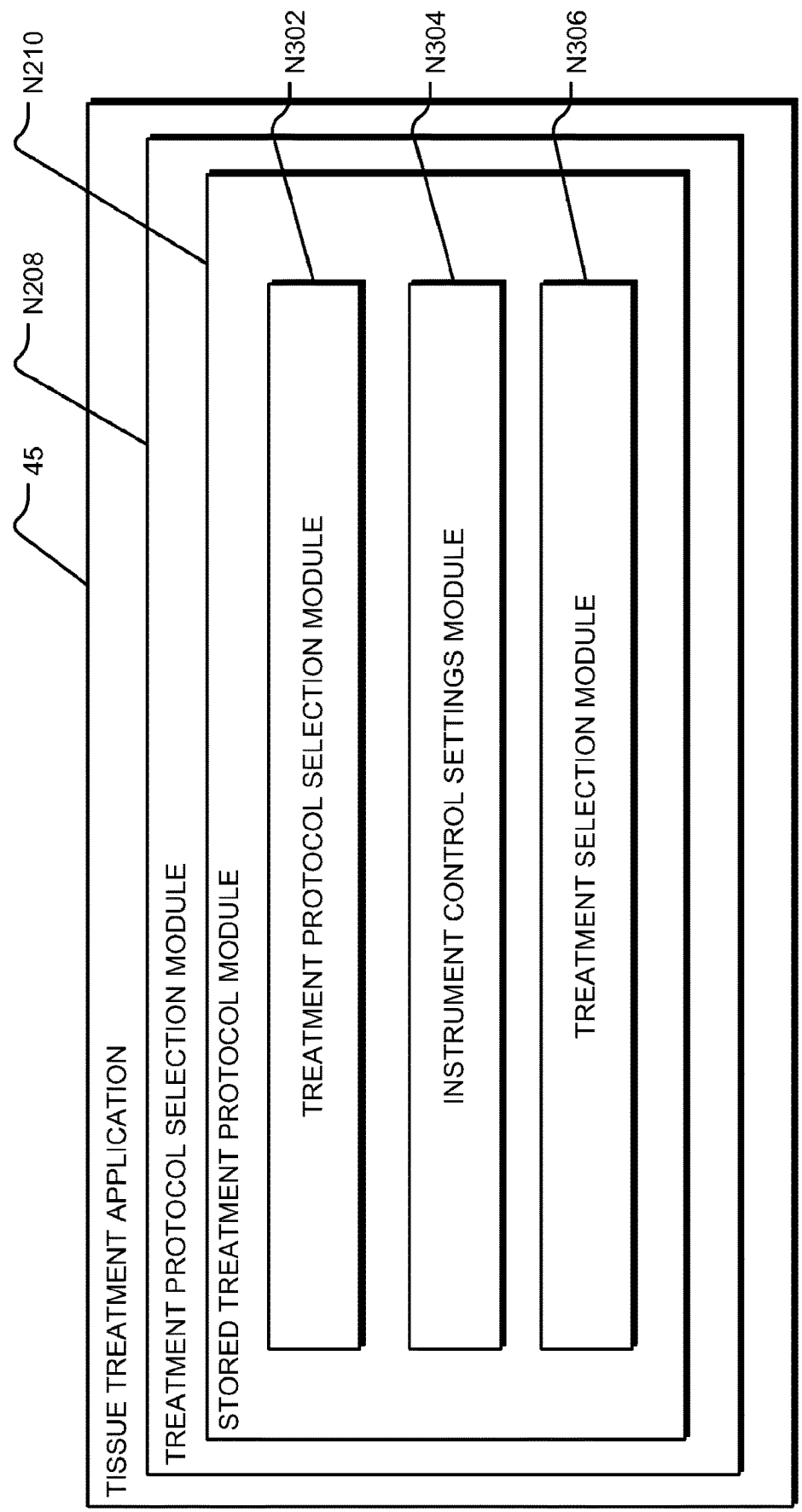
FIG. 35 is a block diagram of a stored treatment protocol selection module of PAPT application.

The stored treatment protocol module N210 is configured to generate a menu of treatment protocols from which the operator may select a treatment for the tissues of the patient, as well as to implement the treatment protocol selected from the menu by the operator. In an embodiment, illustrated in FIG. 35, the stored treatment protocol module N210 may include a treatment protocol selection module N302, an instrument control settings module N304, and a treatment selection module N306. The treatment protocol selection module N302 generates a menu of treatment protocols and displays this menu to the operator via the GUI. The menu of treatment protocols may be a list of standard treatments arranged into one or more organizational schemes including, but not limited to: surgery type, region of patient body, type of patient tissue, type of tissue disorder, treatments previously performed on the patient, desired results of a tissue treatment, and a schedule of planned treatments for a patient. In an embodiment, the stored treatment protocol module N210 may access stored patient information from the database in order to generate the menu of patient-specific treatment protocols. For example, the stored treatment protocol module N210 may retrieve one or more patient-specific treatment protocols from the database N122 for use in the menu of treatment protocols.

Referring back to FIG. 35, the stored treatment protocol module N208 may further include an instrument control settings module N304 configured to determine the appropriate settings for one or more instruments used to implement a treatment protocol selected by the operator from the menu of treatment protocols using the treatment protocol selection module N302. As illustrated in FIG. 2, the system 1111 may administer treatments with one or more instruments including, but not limited to, an impulse stimulator instrument 44 and/or an the electrodes 14 of the electrical stimulation system supported thereon. In an embodiment, the instrument control settings module N304 may determine one or control settings for the impulse stimulator instrument 44 including, but not limited to, preload tissue compression force, magnitude and frequency of a percussive impact to be applied to the tissue. In another embodiment, the instrument control settings module N304 may determine one or control settings for the electrodes 14 of the electrical stimulation system including, but not limited to: magnitude and frequency of an electrical stimulation to be applied to the tissue. A more detailed description of additional instrument control settings that may be determined by the instrument control settings module N304 are provided herein below.

The stored treatment protocol module N208 may further include a treatment selection module N306. Once the treatment protocol has been determined by the treatment protocol selection module N302 and the instrument control settings have been initialized by the instrument control settings module N304, the treatment selection module N306 may initiate the execution of one or more of the treatment modules used to implement a treatment on a tissue associated with a surgical site.

Figure 36:
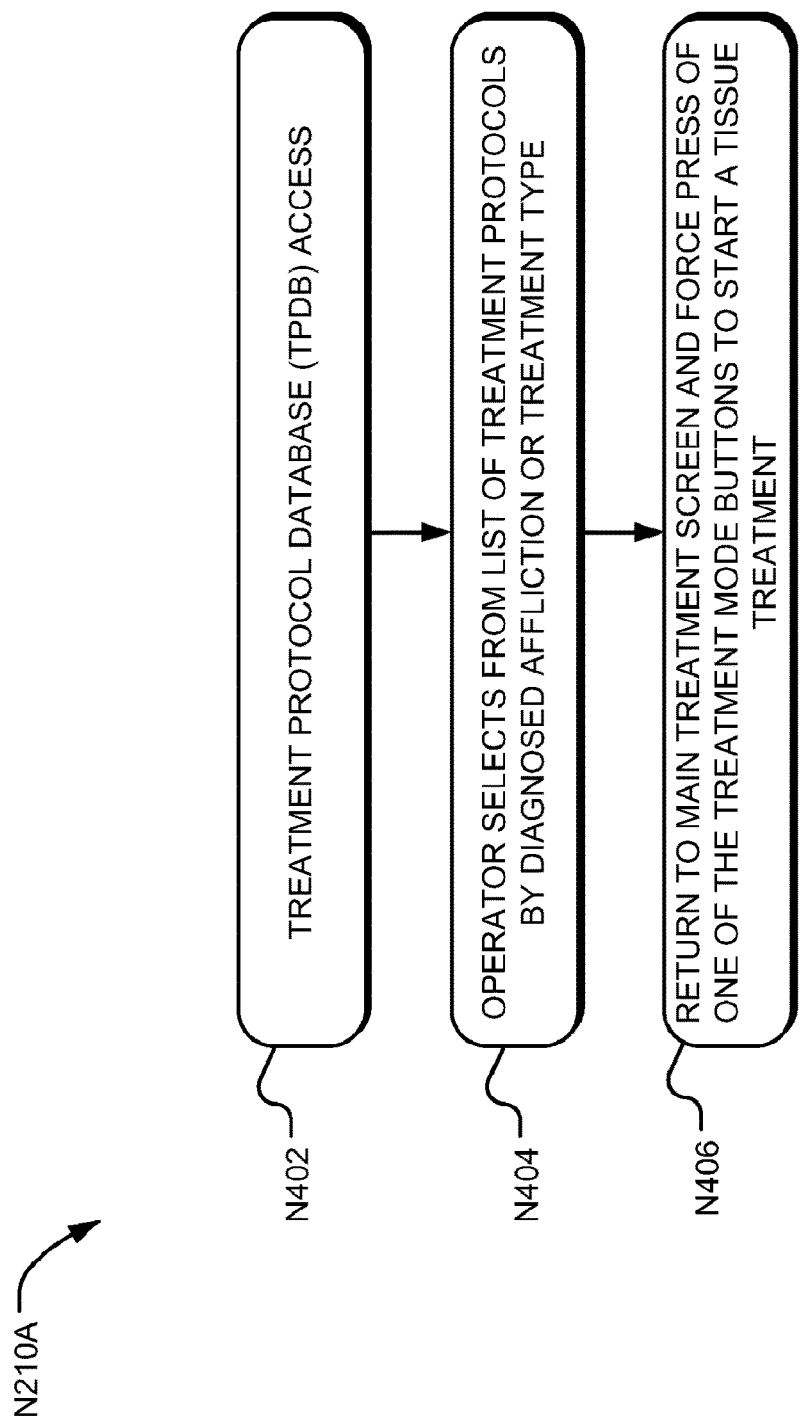
FIG. 36 is a flow chart illustrating an embodiment of a stored treatment protocol selection module.

FIG. 36 is a flow chart illustrating method N210A including a series of actions taken by the operator of the system 1111 in an embodiment of the stored treatment protocol module N208. In this embodiment, the operator of the system 1111 makes a selection to access the stored treatment protocol database at step N402. The operator then selects a desired treatment protocol from the displayed list of stored treatment protocols at step N404. Once a treatment protocol has been selected, the operator then selects one of the treatment modules for execution at step N406. At step N406, the treatment modules available for execution are limited by the stored treatment protocol module N208 to include only those treatment modules that are appropriate for the selected treatment protocol.

b. Tissue Assessment Module

Referring back to FIG. 34, the tissue treatment application N120 further includes a tissue assessment module N212 configured to assess the condition of the tissues of the patient and determine a recommended treatment protocol based on the assessed condition of the tissues. The tissue assessment module N212 may analyze one or more types of information regarding the tissue in order to assess the need for treatment and determine the appropriate type of treatment.

Figure 37:
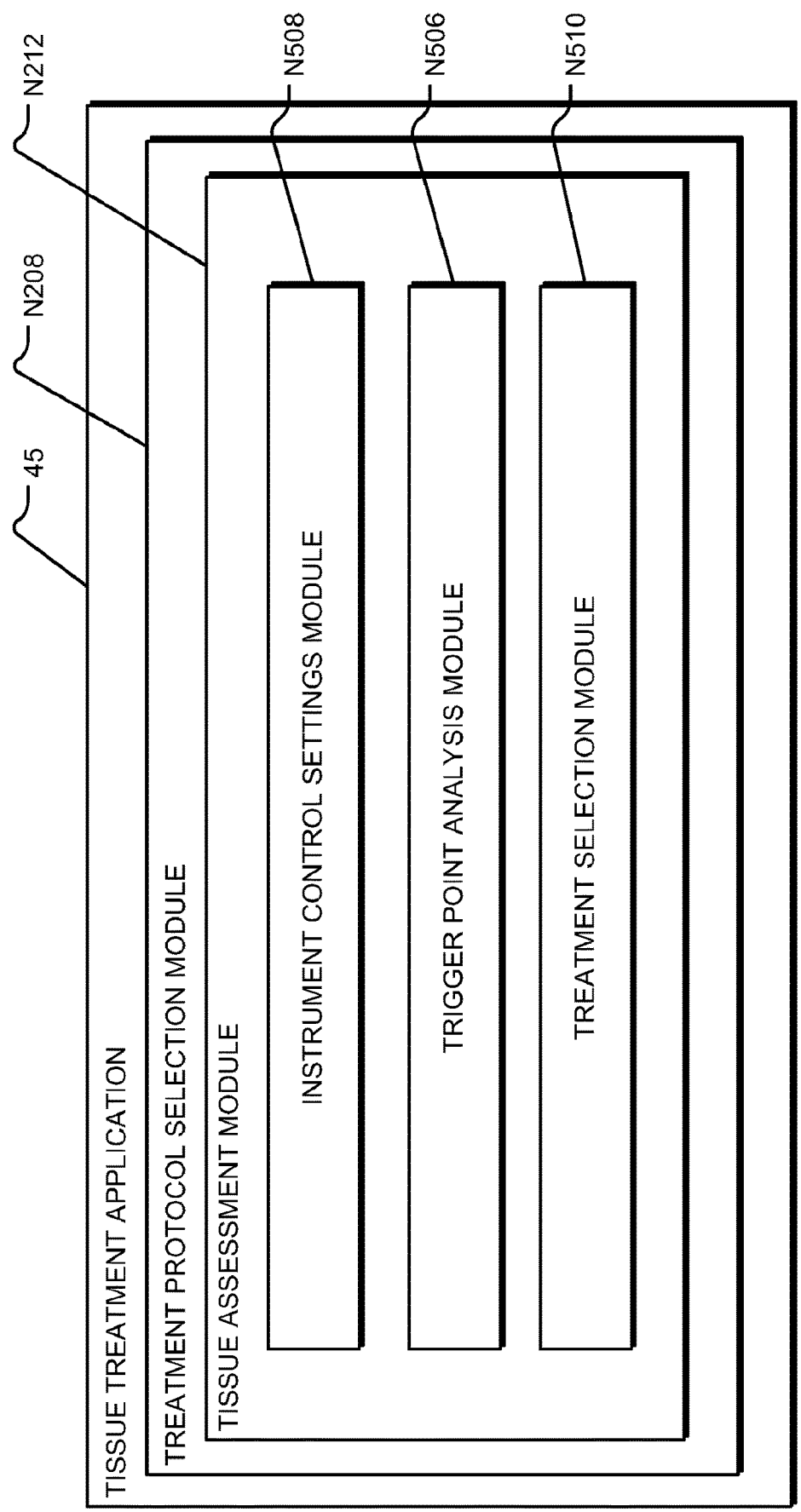
FIG. 37 is a block diagram of a tissue assessment module of a tissue treatment application.

FIG. 37 is a block diagram illustrating an embodiment of the tissue assessment module N212. In this embodiment, the tissue assessment module N212 may include a trigger point analysis module N506, which may implement assessment of selected tissues identified via visual or tactile inspection or via use of the impulse stimulator instrument 44 with or without the use of electrical stimulation via the electrodes 14 supported thereon. Once a recommended treatment protocol has been identified, the instrument control settings module N508 provides the appropriate instrument control settings and the treatment selection module N510 directs the initiation of one or more treatment protocols. Any associated patient data and/or treatment protocol information may be stored in the database N122 (FIG. 34) by the trigger point analysis module N506.

The trigger point analysis module N506 may assess the condition of the tissues of the patient by measuring tissue characteristics including, but not limited to, the response of the tissue to an applied force impulse, or any other aspect of the tissue related to, or correlated with, the health and condition of the tissue. The trigger point analysis module N506 may use any known instrument to perform an additional assessment of the condition of the tissues including, but not limited to, an impulse stimulator instrument as described herein below, an electromyographic electrode, or any other known measurement device appropriate for measurement of a tissue characteristic.

Figure 38:
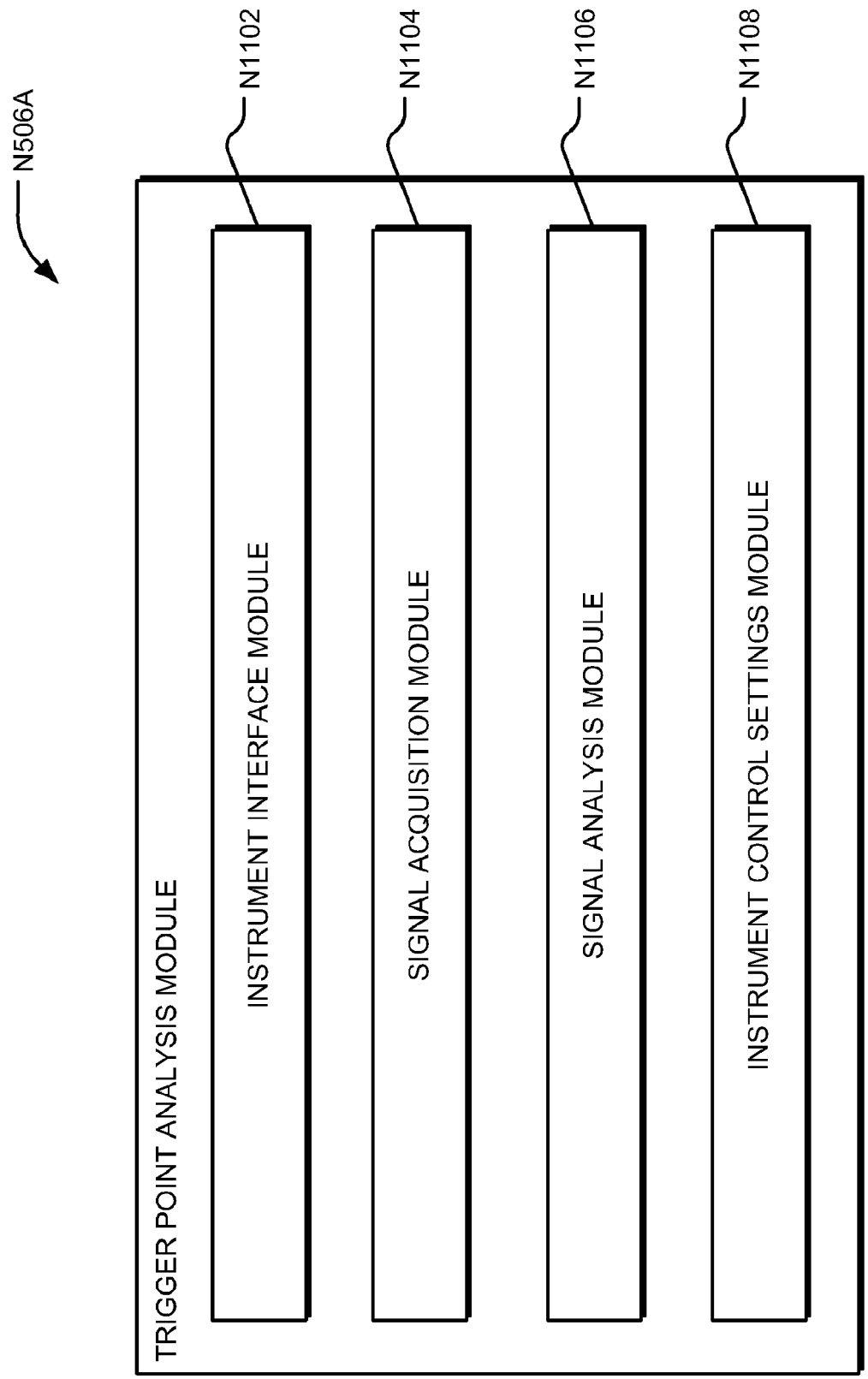
FIG. 38 is a block diagram of a trigger point analysis module.

FIG. 38 is a block diagram illustrating an embodiment of a trigger point analysis module N506A. The trigger point analysis module N506A includes an instrument interface module N1102 to provide a GUI or other interface used by the operator to conduct measurements using one or more devices, a signal acquisition module N1104 to record a measurement signal obtained by the one or more devices, a signal analysis module N1106 to process the signal from the device to determine the condition of the tissue, and an instrument control settings module N1108 to provide instrument control settings such as power settings, frequency of percussive impacts, frequency of applied acoustic pulses, and any other parameter associated with a selected treatment protocol.

The trigger point analysis module N506A may be configured to guide the operator through the steps of locating a landmark, initializing an instrument for measuring a characteristic of a tissue in the vicinity of the landmark, and obtaining one or more measurements using the instrument. The operator may be guided through measurements for one or more landmarks using the trigger point analysis module N506A. The trigger point analysis module N506A may process the measurements of the characteristics of each landmark in combination with that landmark's degree of asymmetry to determine a recommended treatment protocol.

Figure 39:
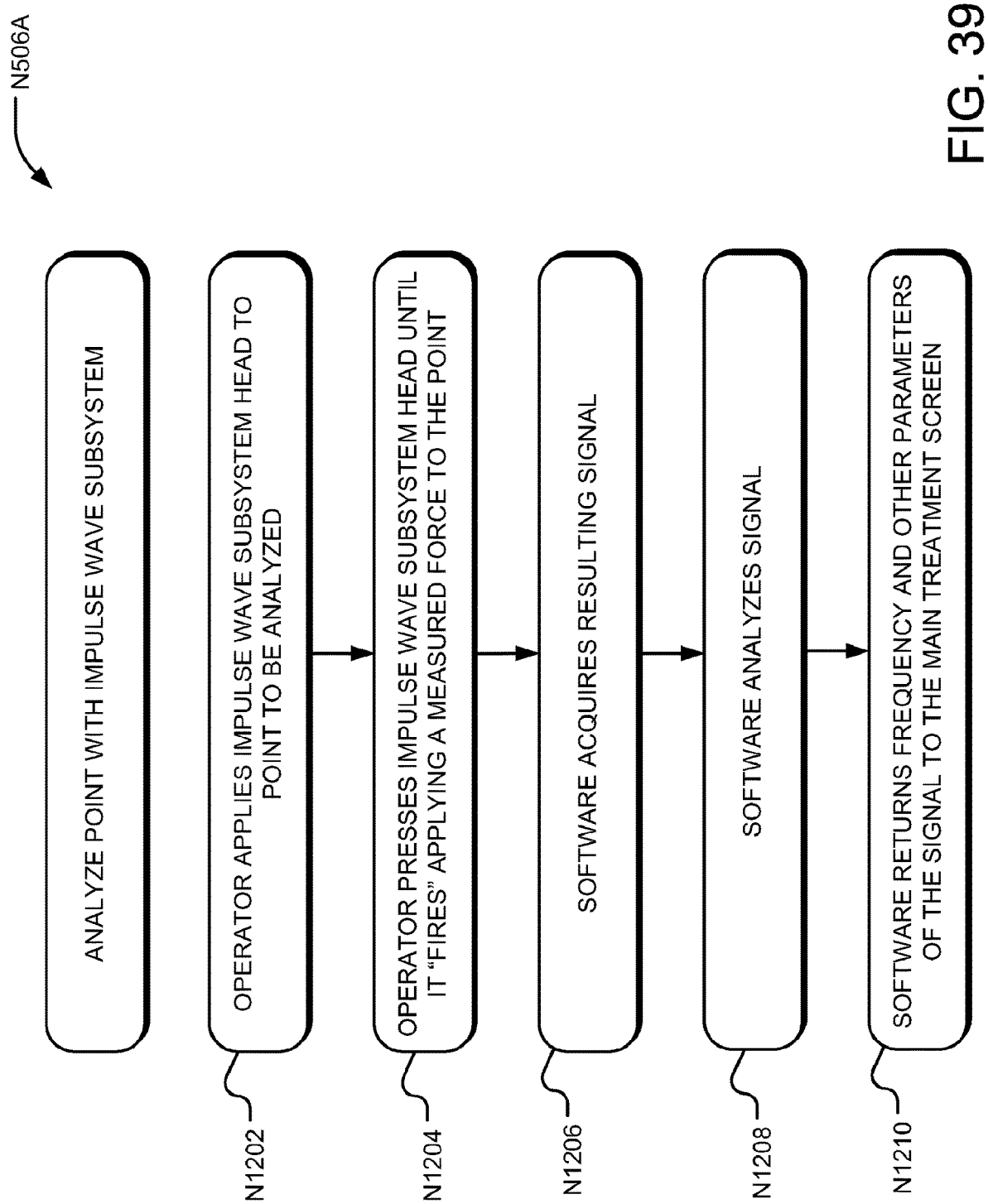
FIG. 39 is a flow chart illustrating an embodiment of a trigger point analysis module.

FIG. 39 is a flow chart illustrating an embodiment of a trigger point analysis module N506B. In this embodiment, an impulse stimulator instrument 44, referred to as an Impulse Wave subsystem in FIG. 39, is used to measure the reaction of a tissue to an applied force impulse. The impulse stimulator instrument 44 is situated at a specified anatomical landmark at step N1202. In an aspect, the specified anatomical landmark may be identified as a landmark associated with a nervous, muscular, circulatory, bone, skin, connective tissue, and/or any other type of tissue structure that may be associated with a surgical site and is the target of the treatment preoperatively and/or postoperatively. The anatomical landmark to be subjected to trigger point analysis may be displayed to the operator of the system 1111 via the display 36. A force impulse is applied to the tissue at step N1204 and a signal encoding the reaction of the tissue to the applied force impulse is acquired by the signal acquisition module N1104 at step N1206. The signal analysis module N1106 analyzes the signal at step N1208, and the instrument control settings are determined by the instrument control settings module N1108 at step N1210. The instrument control settings are used by one or more treatment modules N218 to provide a treatment to a tissue of the patient.

In an aspect, the signal analysis module N1106 may analyze any one or more characteristics of the tissue in response to the force impulse applied by the impulse treatment instrument 44 including, but not limited to, the waveform of the tissue response. Non-limiting aspects of the waveform of the tissue response that may be analyzed by the signal analysis module N1106 include the peak or maximum amplitude of the waveform, the peak time, the rise time, the fall time, the frequency, and the area under the wave. Peak time, as defined herein, refers to the time from the initiation of the waveform to the peak amplitude of the waveform. Rise time, as defined herein, refers to the time elapsed between a waveform amplitude of 10% and 90% of the peak amplitude as the amplitude is rising to the peak amplitude. Fall time, as defined herein, refers to the time elapsed between a waveform amplitude of 90% and 10% of the peak amplitude as the amplitude is falling from the peak amplitude.

Without being limited to any particular theory, there is complexity in the differing shapes of the waveforms associated with the response of the tissues to the force impulses. In an aspect, the signal analysis module N1106 may generate a mathematical representation of the waveform of a tissue response and may further manipulate and interpret the mathematical representation so as to define the amount of resistance, mobility, condition, and/or other characteristics of the tissue.

The signal analysis module N1106 is configured to analyze the relationship of all of the response factors associated with tissue treatment and measurement, namely the analysis of the waveforms as they relate to tissues in general. The relation to the stiffness characteristic (waveform peak), the hysteresis function (wave shape), and the frequency response provide valuable information regarding the state of the measured tissue.

In an aspect, the measured waveform may be sinusoidal and may be influenced by tissue properties including, but not limited, to tissue mobility or resistance to mobility, fascia tension, muscle tonicity, connective tissue resiliency or inertia, local edema and any combination thereof. Each such waveform may be characterized mathematically by determining the peak amplitude, peak time, rise time, fall time, and slew rate; these quantities may facilitate the calculation of frequency response and certain ratios used to mathematically define the waveform characteristics. By analyzing the mathematics of the waveform characteristics, the condition of the tissues may be assessed using previously determined relationships of waveform characteristics and tissue condition.

Figure 7:
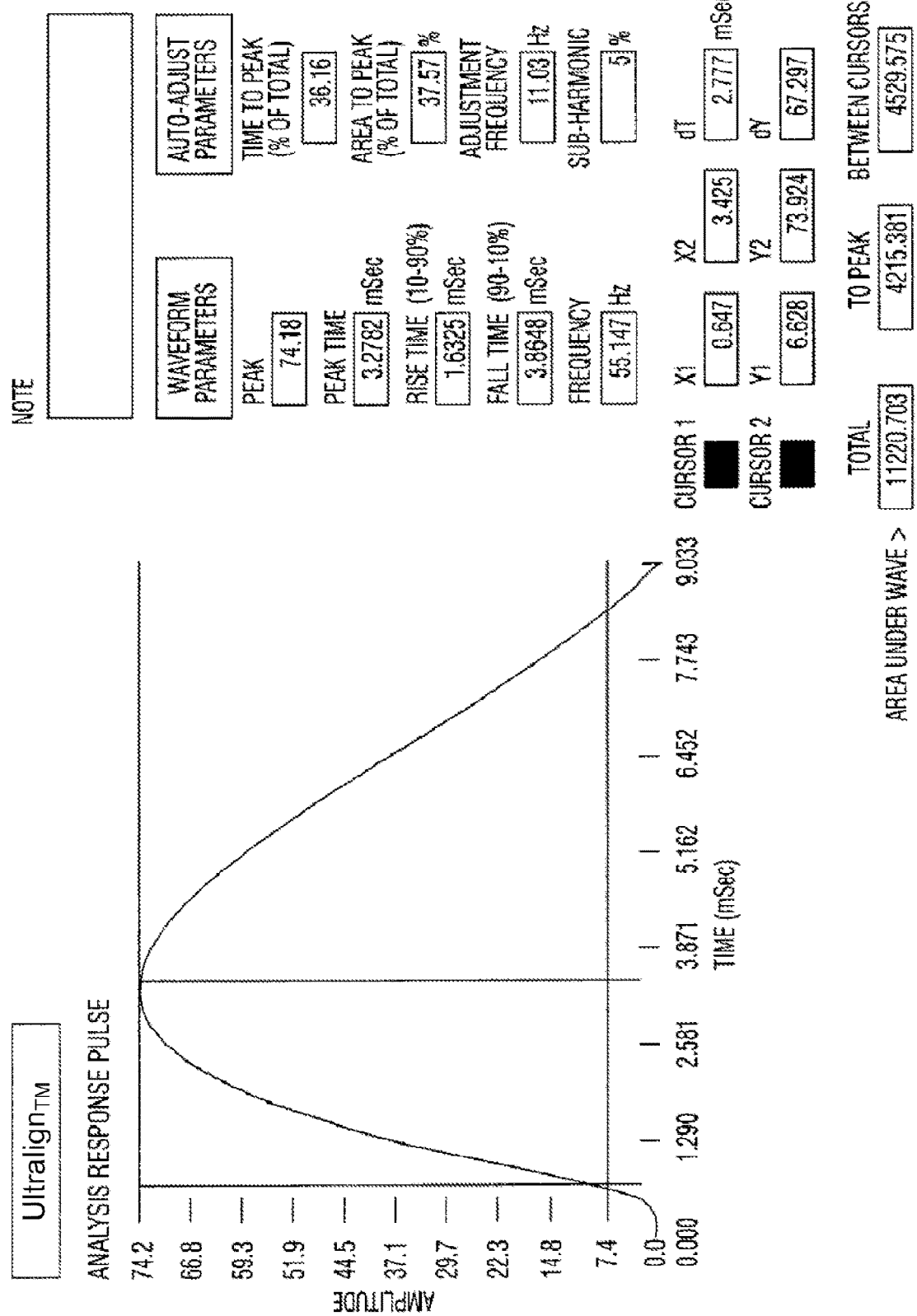
FIG. 7 shows a computer screen depicting a wave form which has derived information from each of the screens shown in FIGS. 3 and 4.
Figure 9:
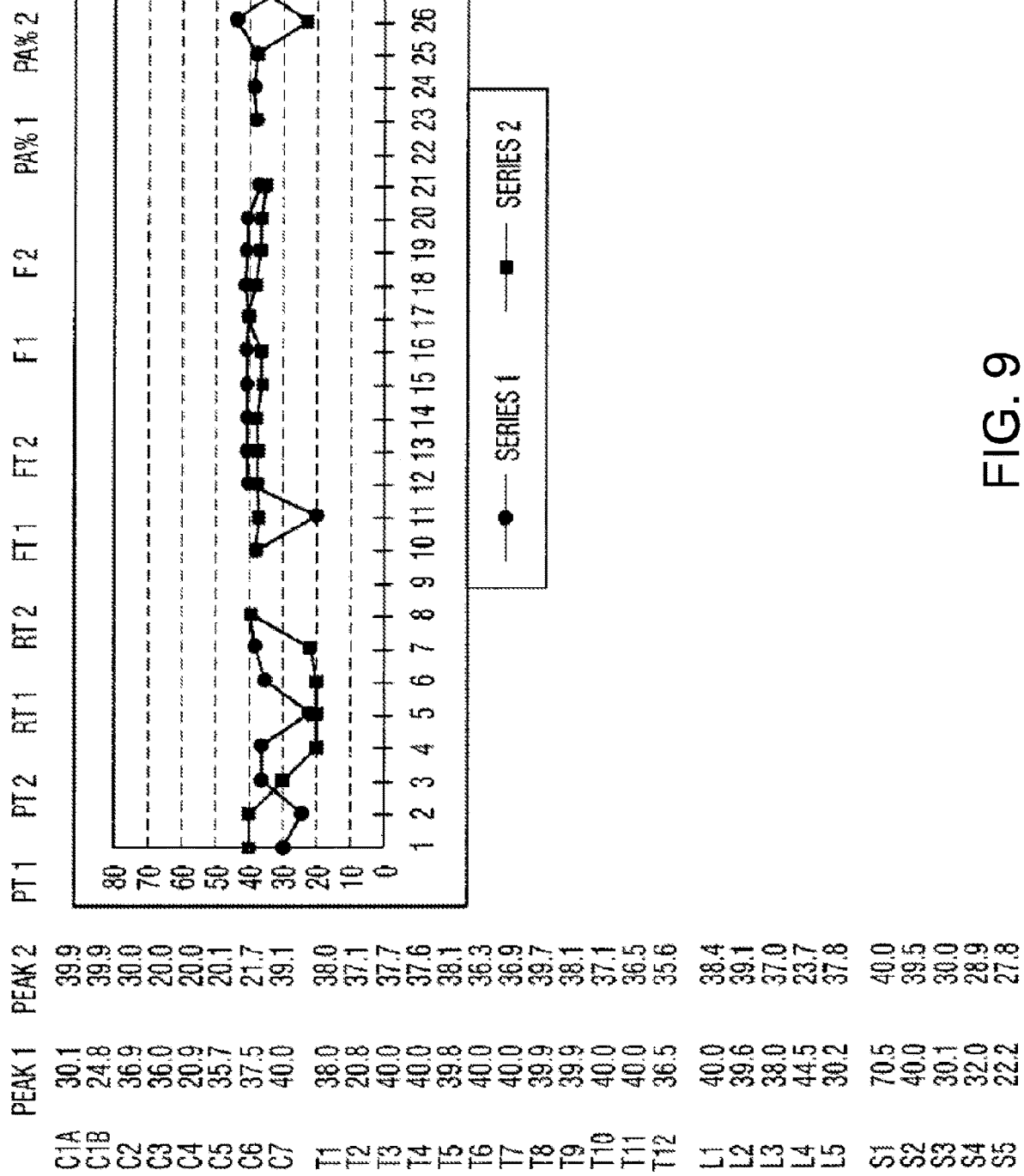
FIGS. 9 through 12 are a sample of charts that may be produced so that data may be presented in an informational format for comparison.
Figure 10:
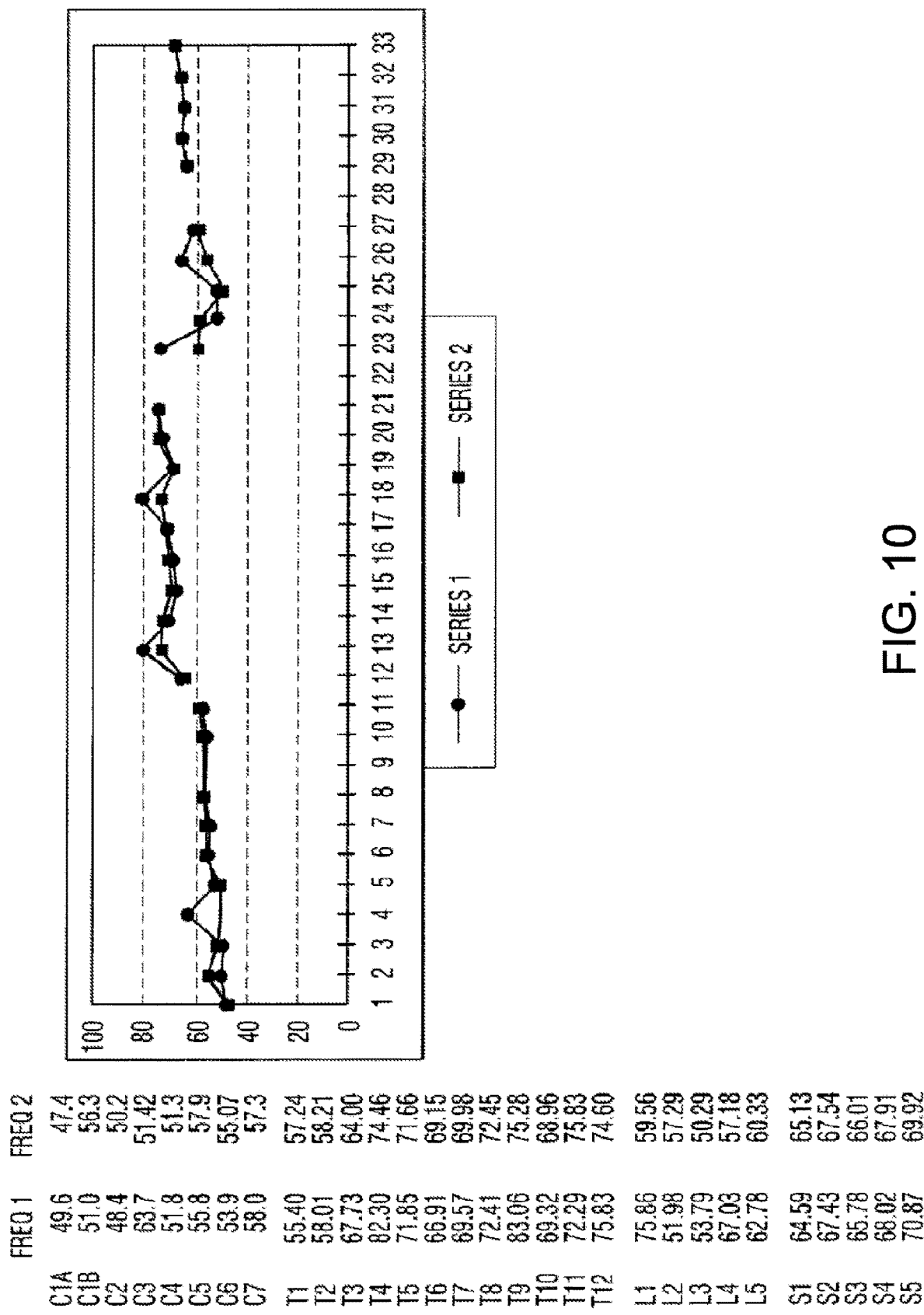
Figure 11:
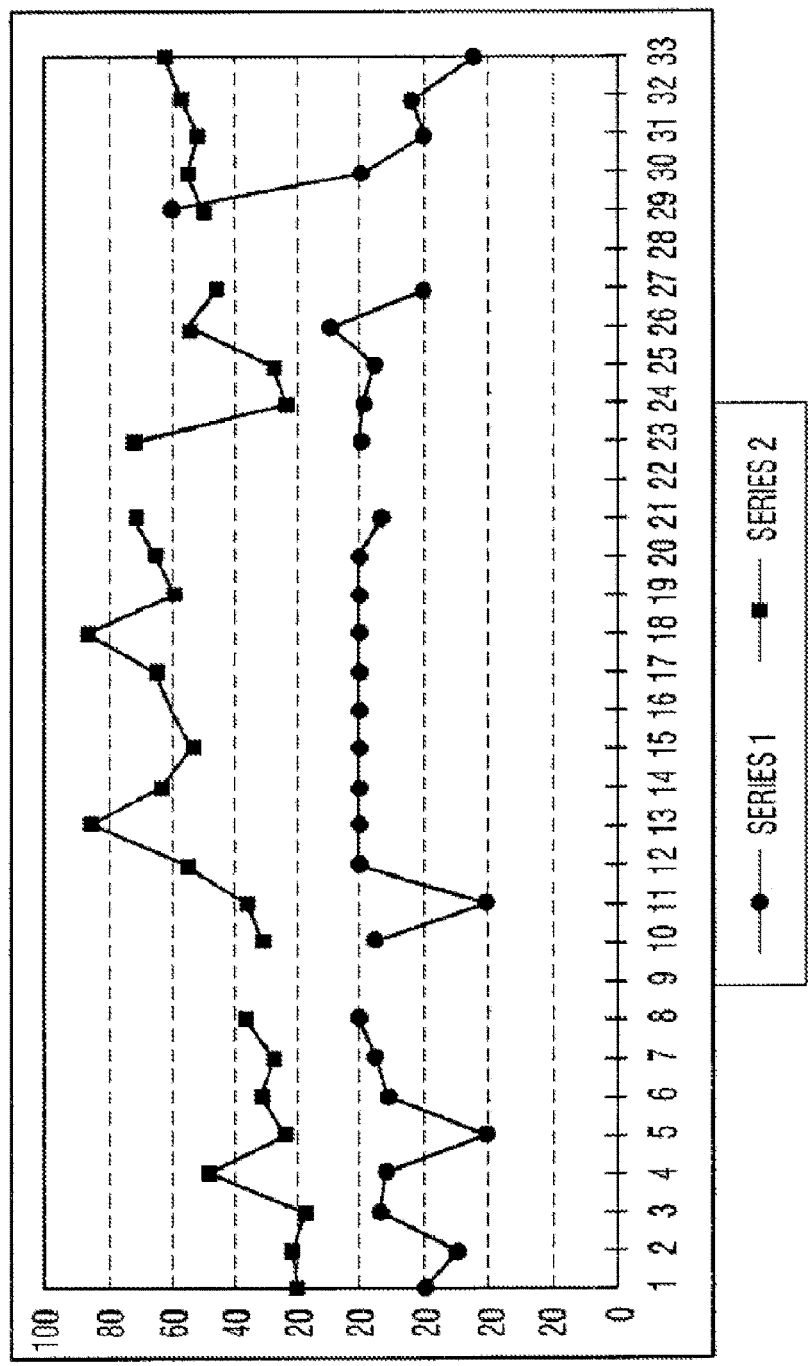
Figure 12:
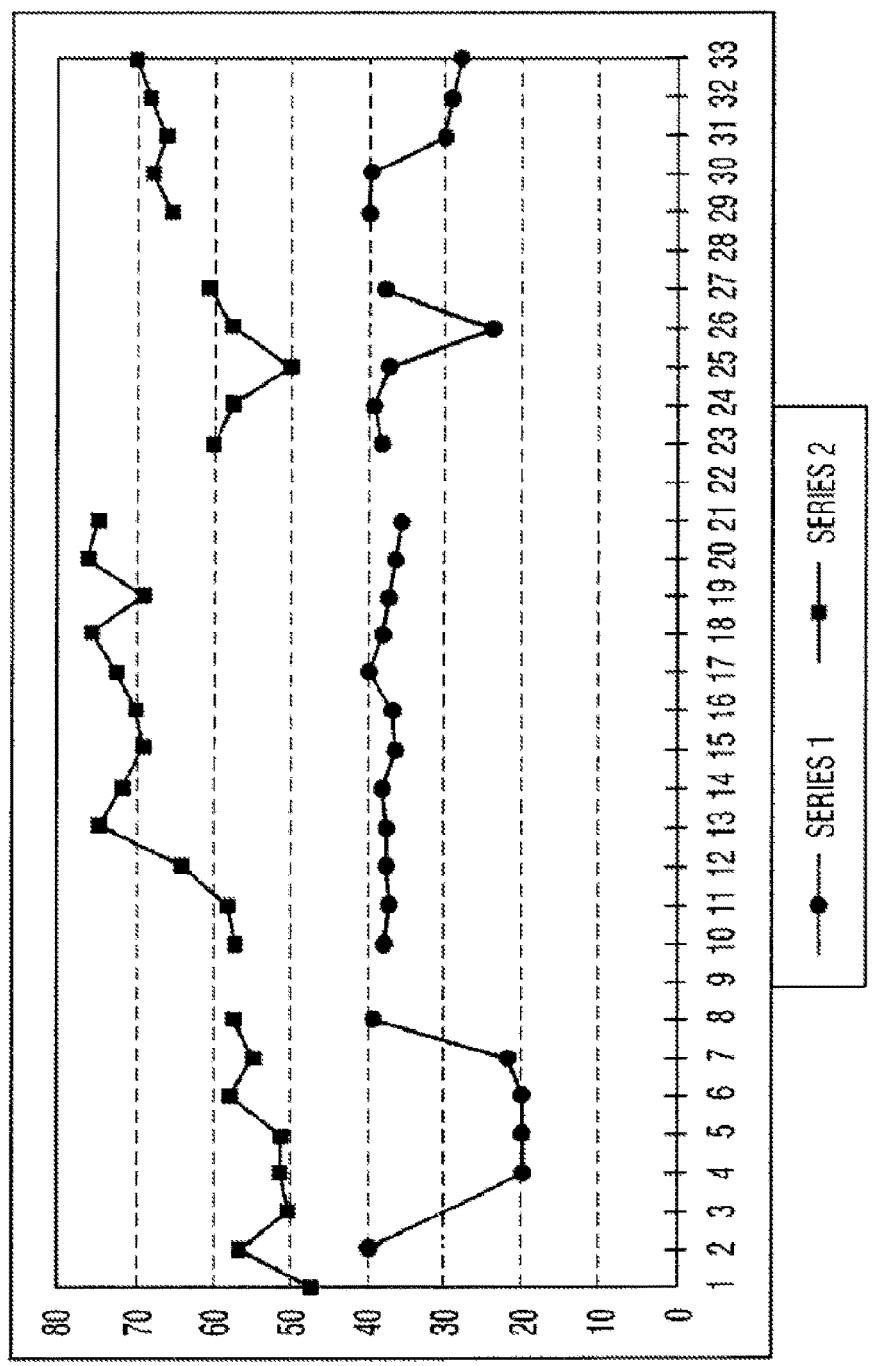

As the data are collected and logged and after all of the pertinent mathematic calculations are made, a summary display of the waveform and analysis may be presented on the display 36 as illustrated in FIG. 7. The summary display may include a graphic display of the waveform, and the pertinent data and derived ratios may be displayed for assessment by the operator during a trigger point analysis. The data associated with the summary display may be stored in the database N122 for use by the tissue treatment application N120A in determining the appropriate treatment protocol and associated instrument control settings. In addition, the stored data associated with a trigger point analysis may be incorporated into a more comprehensive database used to develop and refine predictive diagnoses using methods of analysis including, but not limited to, clinical assumptions and statistical models. Normal values associated with the waveform analysis of healthy tissues may be compiled, stored, and used to compare normal versus aberrant tissues. Stored data may also be used to compare pre-treatment and post-treatment tissues.

i. Instrument Control Settings Module

Referring to FIG. 37, the tissue assessment module N212 may further include an instrument control settings module N508 configured to determine the control settings for the instruments to be used to administer a treatment to the tissues of the patient. The control settings may be determined based on tissue readings taken via any of the means of the system disclosed herein and via physical inspection guided by veterinarian experience, as well as any additional characteristics of the tissues determined by the trigger point analysis module N506. In an embodiment, the instrument control settings module N508 may determine one or more control settings for the impulse stimulator instrument 44 including, but not limited to preload tissue compression force, magnitude and frequency of a force impulse to be applied to the tissue. In another embodiment, the instrument control settings module N508 may determine one or control settings for the electrical stimulation afforded by the electrodes 14 including, but not limited to: magnitude and frequency of an electrical pulse to be applied to the tissue.

ii. Treatment Selection Module

Referring to FIG. 37, the tissue assessment module N212 may further include a treatment selection module N510 configured to select one or more treatment protocols based on the analysis of the tissues determined by the 2D tissue assessment module N502, as well as other tissue characteristics determined by the trigger point analysis module N506. The recommended treatment protocols may be displayed to the operator as a list of treatment protocol options in an aspect. One or more treatment protocols may be selected from the displayed list by the operator in order to initiate one or more treatments to the tissues of the patient.

c. Operator-Selected Treatment Module

Referring back to FIG. 34, the treatment protocol selection module N208 includes an operator-selected treatment module N214 configured to develop and implement a treatment protocol specified by an operator via the input device 500 (shown in FIG. 2). In an aspect, the operator-selected treatment module N214 may offer guidance to the operator in the form of menus or suggested ranges for applied stimulation frequencies, force impulse magnitudes, frequencies of impulse production, and any other parameter associated with the treatment protocol selected by the operator.

In an aspect, the operator may specify a particular treatment mode and anatomical landmarks to be treated. An image may be displayed within a GUI display in this aspect to show the selected anatomical landmarks to be treated. Upon selection of a particular anatomical landmark, the GUI may display the control settings of the instrument used to provide the treatment to the tissues of the patient to the operator. The operator may then specify the control settings of the instrument via the GUI. Alternatively, the GUI may guide the operator through a measurement of another characteristic of the tissue, and control settings of the instrument may be recommended to the operator based on the measured condition of the tissue. The instrument control settings are used to configure the instrument used to administer the treatment to the tissues of the patient.

III. Treatment Modules

Referring back to FIG. 34, the treatment protocol selection module N120A selects a treatment protocol for a treatment of a tissue of a patient as discussed herein above. To implement the selected treatment protocol, the system 1111 may make use of one or more treatment modules such as, for example, a neural treatment module, a muscular treatment module, a circulatory treatment module, a bone or hard tissue treatment module, a tendon/ligament or connective tissue module, a skin module, etc. In one embodiment, the tissue treatment module N218 or any other treatment module provides an interface with which the operator may configure the instrument to be used to treat the tissue of the patient according to the selected treatment protocol. In addition, each of the treatment modules may provide step-by-step guidance to the operator for placing the instrument on one or more selected anatomical landmarks of the patient and operating the instrument used to provide the treatment specified by the selected treatment protocol.

In an aspect, measurements of the condition of the tissues including, but not limited to, the response of the tissue in reaction to applied force impulses may be obtained. The post-treatment measurements may be stored in the database N122 in an embodiment.

Detailed description of a general tissue treatment module N218 is provided herein below.

a. Tissue Treatment Module

Referring back to FIG. 2, in one embodiment, the data acquisition circuitry 45 and the software code 38 thereof includes a preoperative and postoperative treatment ("PAPT") module N218 configured to guide the operator through pre-operative and post-operative treatments associated with one or more surgeries associated with one or more anatomical landmarks in accordance with a selected treatment protocol. In this aspect, the PAPT module N218 may apply percussive impacts to tissues using the impulse stimulator instrument 44. Other treatment protocols including, but not limited to, electrical stimulation applied to tissues in vicinity of the surgical site may be implemented in other embodiments. The electrical stimulation may be in the form of electrical stimulation protocols described above.

Figure 40:
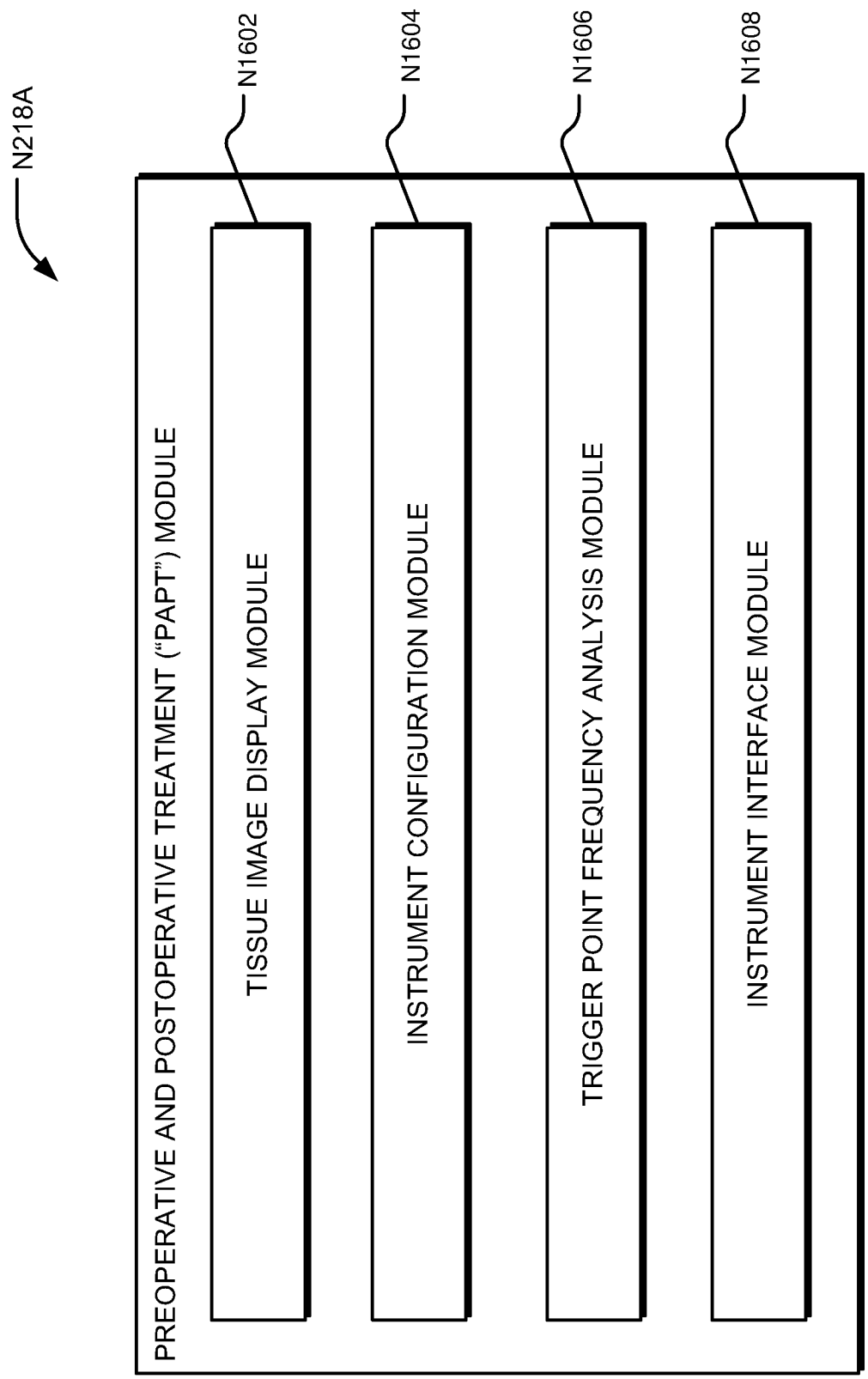
FIG. 40 is a block diagram of a preoperative and post-operative treatment ("PAPT") module.

FIG. 40 is a block diagram illustrating an embodiment of a PAPT module N218A. The PAPT module N218A may include a tissue image display module N1602 to produce a GUI used to guide the operator through a treatment of tissue associated with a surgical site. Examples of tissues adjacent a surgical site that may be treated with the system include, without limitation, nerves, vasculature, muscle, connective tissue such as ligaments and tendons, Golgi tendon organs, fascia, cartilage, tendon/muscle junctions, tendon/bone junctions, skin layers, etc.

An instrument configuration module N1604 may be used to specify the control settings of the impulse stimulator instrument 44 used to implement a treatment of the tissue including, but not limited to the magnitude and frequency of the applied force impulse, and the duration of the treatment. A trigger point frequency analysis module N1606 may guide the operator through an analysis in which the stimulator instrument is used to measure the response of the tissue through a range of frequencies of the applied force impulse and to determine one or more instrument control settings based on an analysis of the measured tissue response. The instrument interface module N1608 provides a GUI or other interface used by the operator to operate the impulse stimulator instrument while implementing a selected treatment protocol.

Figure 41:
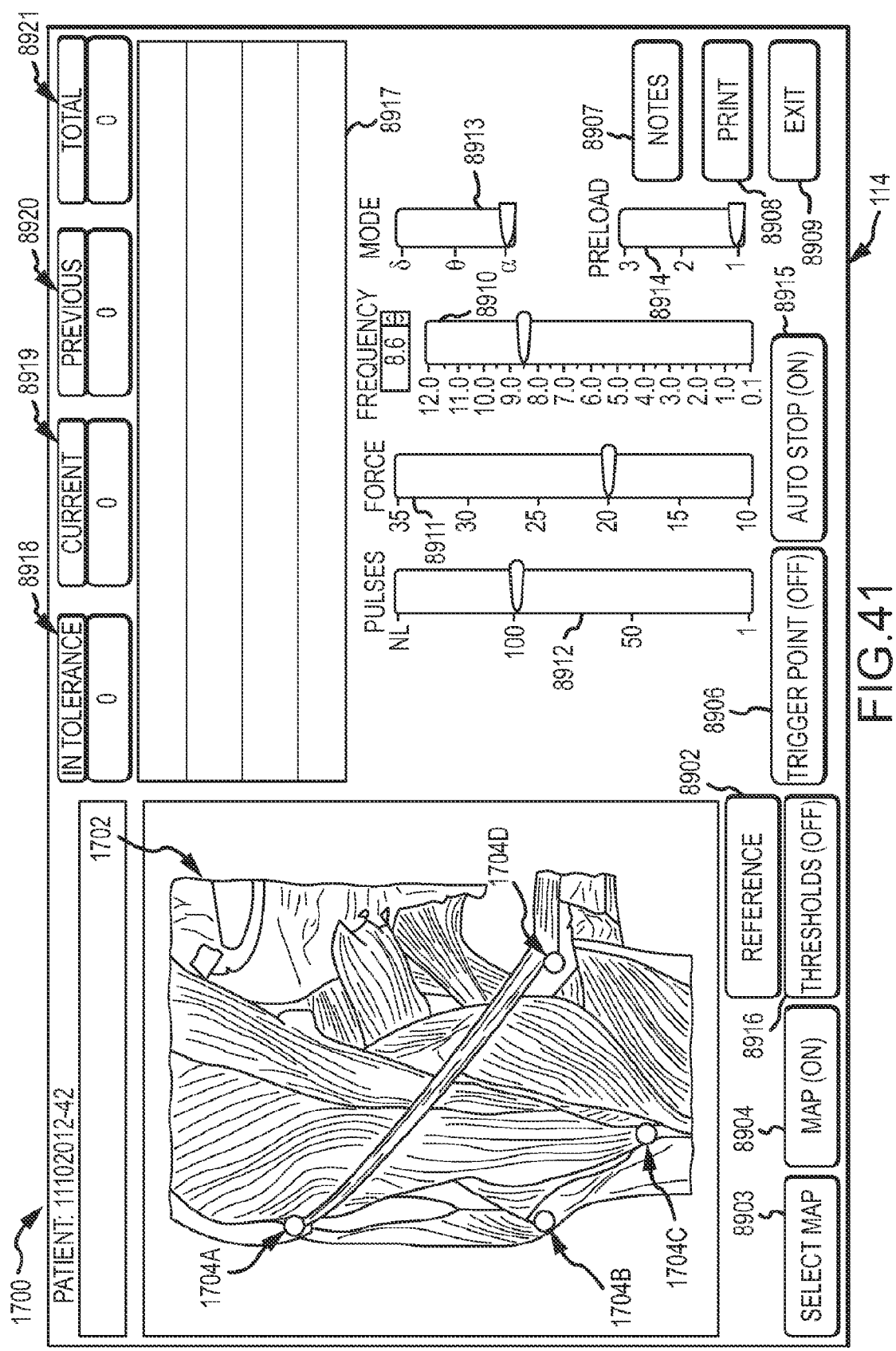
FIG. 41 is an embodiment of a tissue treatment guidance display depicting a patient hip that is to be the target of a surgical procedure.
Figure 42:
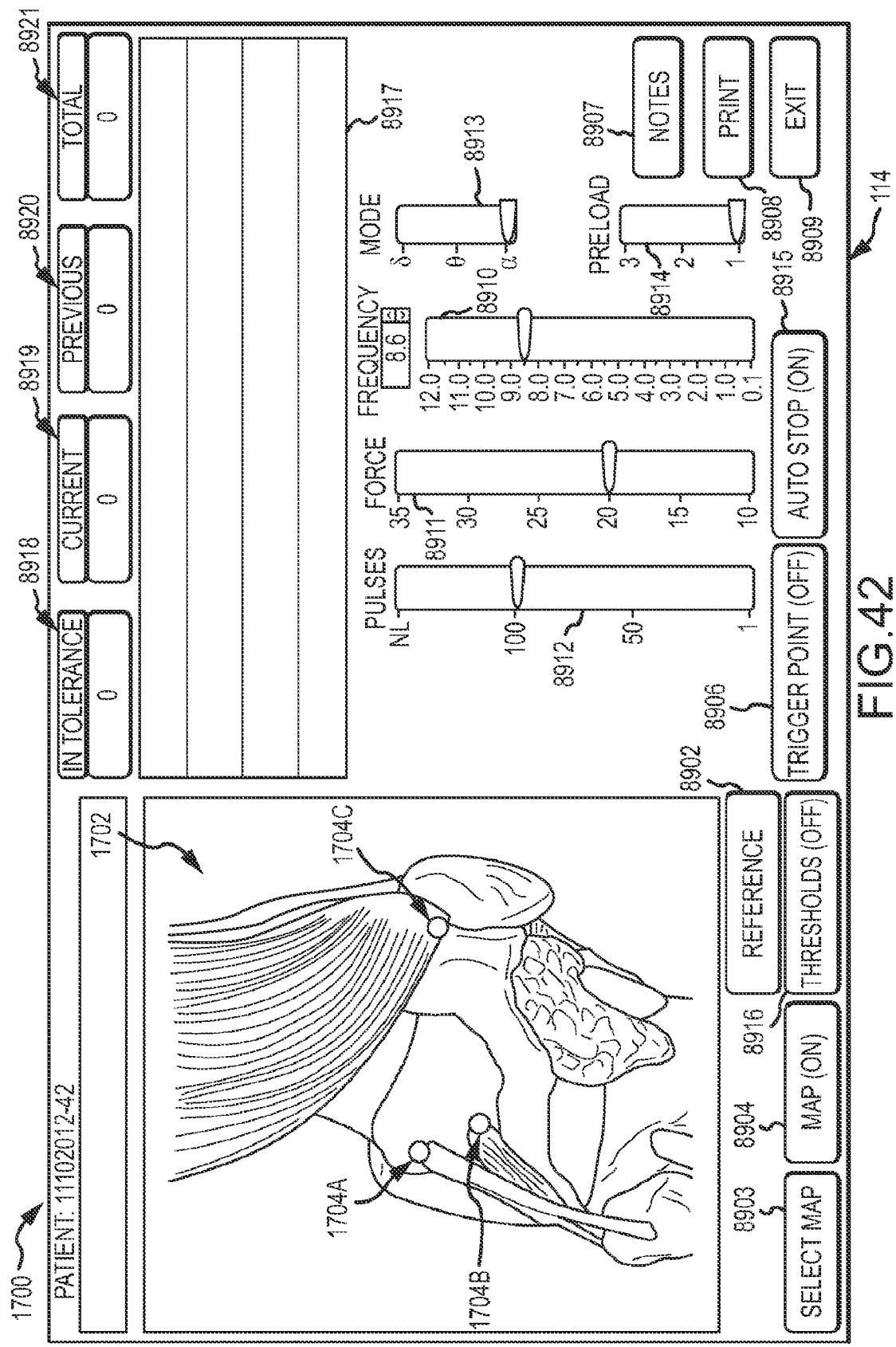
FIG. 42 is an embodiment of a tissue treatment guidance display depicting a patient knee that is to be the target of a surgical procedure.
Figure 43:
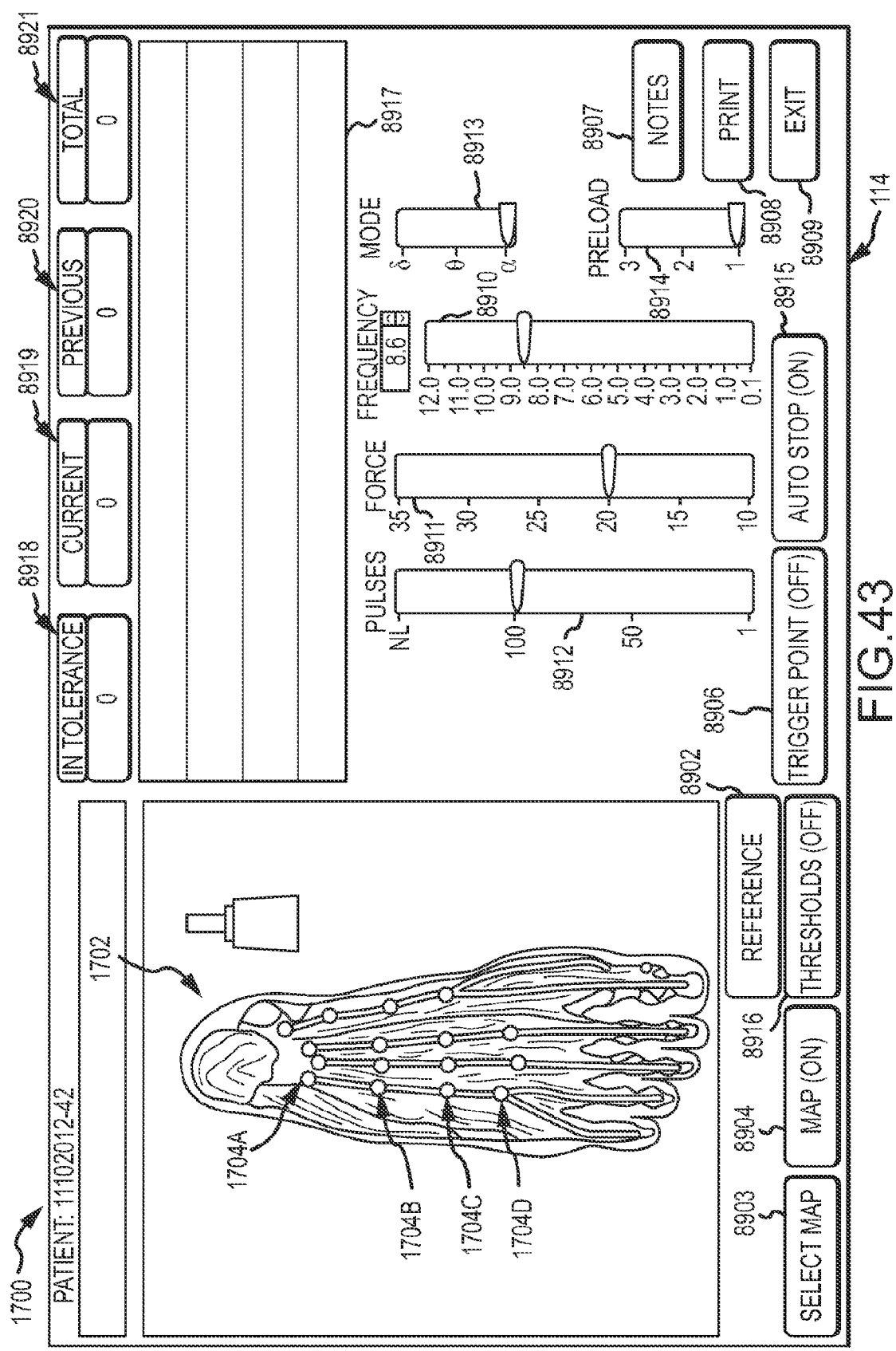
FIG. 43 is an embodiment of a tissue treatment guidance display depicting a patient foot that is to be the target of a surgical procedure.
Figure 43A:
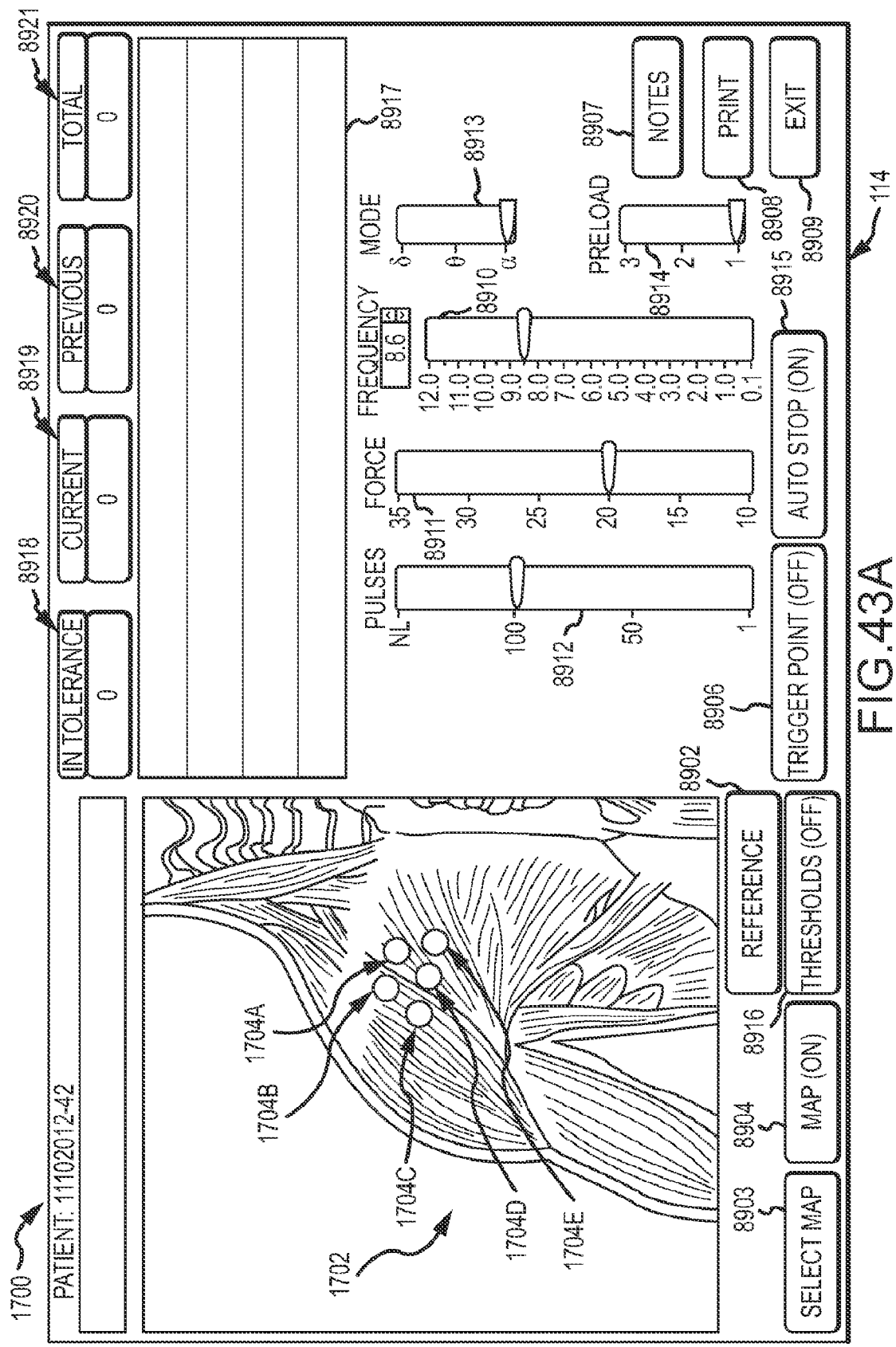
FIG. 43A is an embodiment of a tissue treatment guidance display depicting a patient shoulder that is to be the target of a surgical procedure.

Examples of tissue image displays 1700 are illustrated in FIG. 41-43A. A tissue image display 1700 may include a surgical site tissue image 1702 illustrating the location of tissue adjacent a surgical site to aid the operator in locating the appropriate region for treatment. For example, as illustrated in FIG. 41, the surgical site tissue image 1702 depicts the tissue adjacent a hip surgical site such as in the case of a hip arthroplasty. FIG. 42 illustrates a surgical site tissue image 1702 depicting the tissue adjacent a knee surgical site such as in the case of a knee arthroplasty. FIG. 43 illustrates a surgical site tissue image 1702 depicting the tissue adjacent a foot surgical site such as in the case of a plantar fasciitis or pes equines. FIG. 43A illustrates a surgical site tissue image 1702 depicting the tissue adjacent a shoulder surgical site such as in the case of a shoulder arthroplasty.

As can be understood from FIG. 41 (and in a similar fashion with respect to FIGS. 42-43A), in an aspect, the location of anatomical landmarks 1704A-1704D identified by a treatment protocol selection module of the data acquisition circuitry 45 and the software code 38 may be superimposed on the tissue image 1702. The frequency at which the force impulses are applied to the tissues may be displayed and/or specified using a GUI control element such as the slider control 8910 illustrated in FIG. 41. In this example, a hip region is illustrated in the tissue image 1702, and the tissues and anatomical landmarks 1704A-1704E pertain to a human hip region. Of course, depending on what surgical site is being treated and how the treatment system 1111 is configured, the tissue image 1702, tissues and anatomical landmarks can pertain to any potential surgical site including without limitation hips, knees, or feet, as indicated by FIGS. 41-43A.

The tissue display 1700 may further include controls (e.g., buttons, sliders, etc.) and readouts (e.g., gages, graphs, etc.) 8901-8921 used to control and understand various aspects of the treatment of the tissue. In one embodiment, the GUI 1700 depicted in FIG. 41 is displayed on the display 36 of FIG. 2 once the setup of the system 1111 has been achieved as described below with respect to the GUI 8860 of FIG. 44. As indicated in FIG. 41, the GUI 1700 includes the anterior hip region image 1702 with its trigger points 1704A-1704D. The GUI 1700 also includes an input device 114 with touch sensitive screen buttons "Reference", "Select Map", "Map", "Trigger Point", "Notes", "Print", and "Exit" 8902-8904 and 8906-8909. The input device 114 of the GUI 1700 also includes touch sensitive screen sliders "Frequency", "Force", "Pulses", "Mode", and "Preload" 8910-8914. Finally, the GUI 1700 also includes "Auto Stop" and "Thresholds" indicates 8915 and 8916 and a graphical display 8917 to illustrate the treatment and "In Tolerance", "Current", "Previous" and "Total" indicators 8918-8921.

In one embodiment, the user interface contains various controls that aid the user by providing control and treatment feedback information. The user can select the treatment node map by selecting "Select Map" 8903, and the treatment nodes 1704A-1704D can be caused to display on the tissue image 1702 by selecting "Map" 58904. The "Reference Button" 8902 is used to store information regarding the anatomical area of treatment, treatment overview and rationale, treatment goals and or expected responses.

Functionality can be quickly switched from a protocol to a trigger point by toggling between protocols and trigger points via "Select Map" 8903 to select the type of therapy desired. The notes button 8907 brings up a window to allow the user to enter information in a text format via the keyboard. General treatment controls include frequency, force and limits 8910-8912. While the computer calculates the frequency, the user can override it by touching the screen and moving the digital slider. However, the force and limit have defaults that are parameters selected by the user to determine how much power will be used and the maximum number of impulses that can be delivered. The selection mode 8913 is used to choose what harmonic frequency is chosen within the range of frequencies of 0.1 to 12 Hz.

There are different input frequencies depending on whether one is attempting to stimulate a nerve, voluntary muscle fiber or involuntary muscle fiber. The ranges are Alpha 7-12, Theta 4-7, and Delta 0.1 to 4 Hz. The selection mode slider 8913 allows the user to dynamically choose the proper harmonic dynamically.

The preload function 8914 changes the amount of pressure that is used to compress the tissue before the treatment applicator begins to produce impulse. Because surgical target site and different types of treatment target tissue may vary widely in its physiological characteristics and tolerances, varying amounts of pressure can be used. Preload 8914 provides a way to control this pressure without having to change treatment heads.

As treatment is progressing, information about the tissue response is shown on a strip chart 8917. Information includes real time output from the sensor showing changes in tissue tone, changes in tissue frequency response and changes in wave shape characteristics. If auto-stop is chosen 8915, these signals will be interpreted and the device will automatically stop treatment based upon a definable tolerance. For instance, if a tolerance of 3% is used for tissue stiffness, the device will stop treatment based upon receiving a predefined number of impulses that are all within 3% of each other.

Thresholds 8916 may be turned on or off to give the user a visual scale of how the treatment parameters are progressing in real time with regard to the auto-stop parameters. As the treatment progresses the real time measurements are tabulated in 8918 through 8921. "In tolerance" 8918 displays the impulses that fall within the pre-defined tolerance indications. "Current" 8919 displays the number of impulses that have been delivered during the activation of the treatment head during the active treatment while "previous" 8920 shows the previous number of impulses during the last treatment application and "Total" 8921 displays the total number of impacts delivered during the entire treatment. After the treatment is concluded the users may print the screen by selecting the "print" button 8908 or the user may simply exit the protocol screen by touching the "exit" button 8909.

Figure 44:
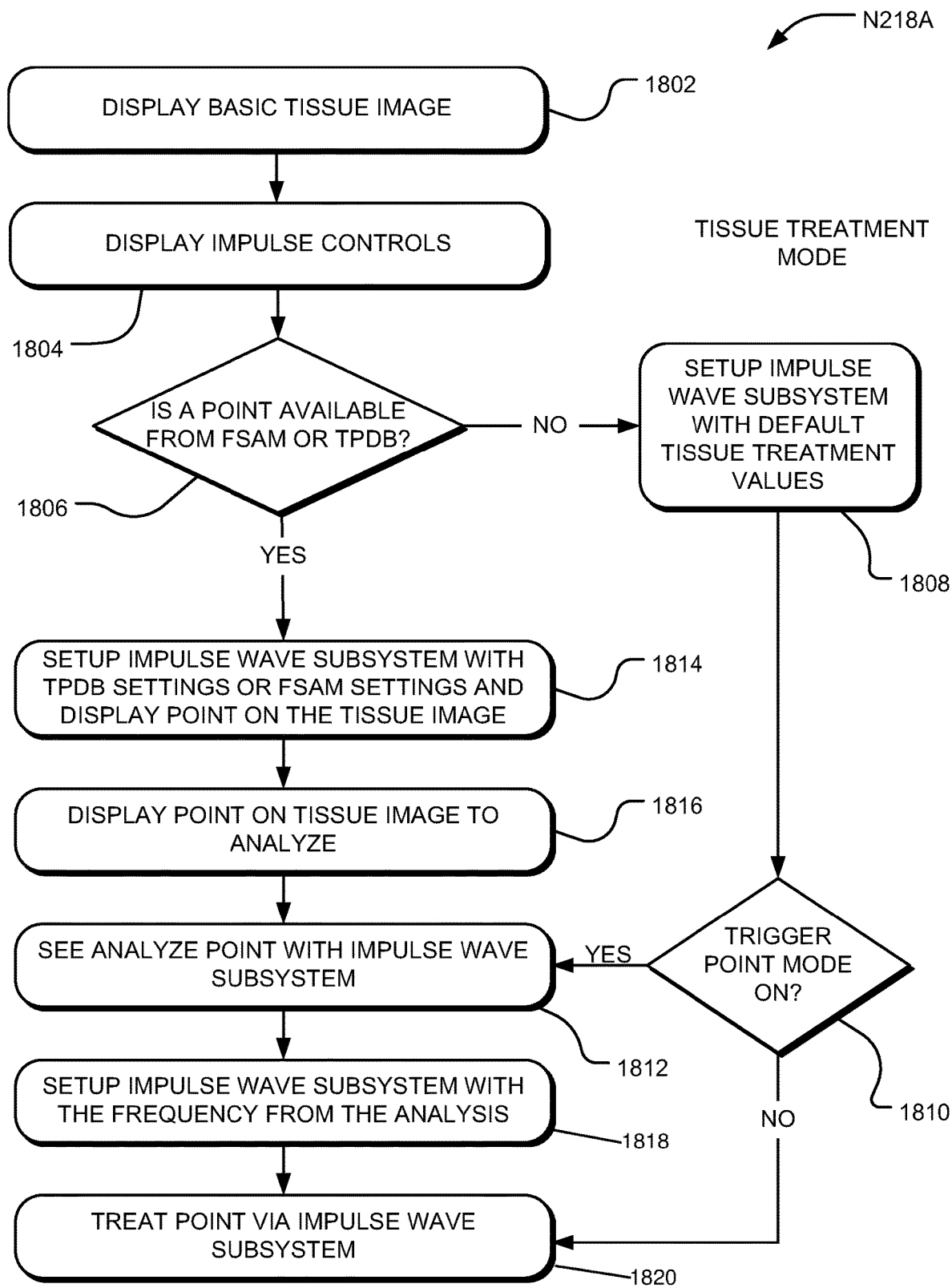
FIG. 44 is a flow chart illustrating an embodiment of a tissue treatment module.

FIG. 44 is a flow chart illustrating an embodiment of the tissue treatment module N218A. The tissue image 1702 and controls for the impulse stimulator instrument 44 may be displayed in the tissue display 1700 at steps 1802 and 1804. The tissue treatment module 218A determines whether instrument control settings have been specified using the stored treatment protocol module N210 or tissue assessment module N212 at step 1806. If no instrument control setting has been specified, the instrument control settings are populated with default values at step 1808. Once the default values have been loaded, the tissue treatment module N218A determines if a trigger point analysis is desired to refine the default settings at step 1810. If desired, a trigger point analysis is performed at the anatomical landmark at step 1812.

If instrument control settings were identified at step 1806, the settings are loaded into the tissue display 1700 at step 1814. An anatomical landmark to be treated is displayed on the tissue display 1700 at step 1816. If a trigger point analysis was conducted, the recommended instrument control settings are loaded into the tissue display 1700 at step 1818, and the treatment is implemented at step 1820.

Figure 45:
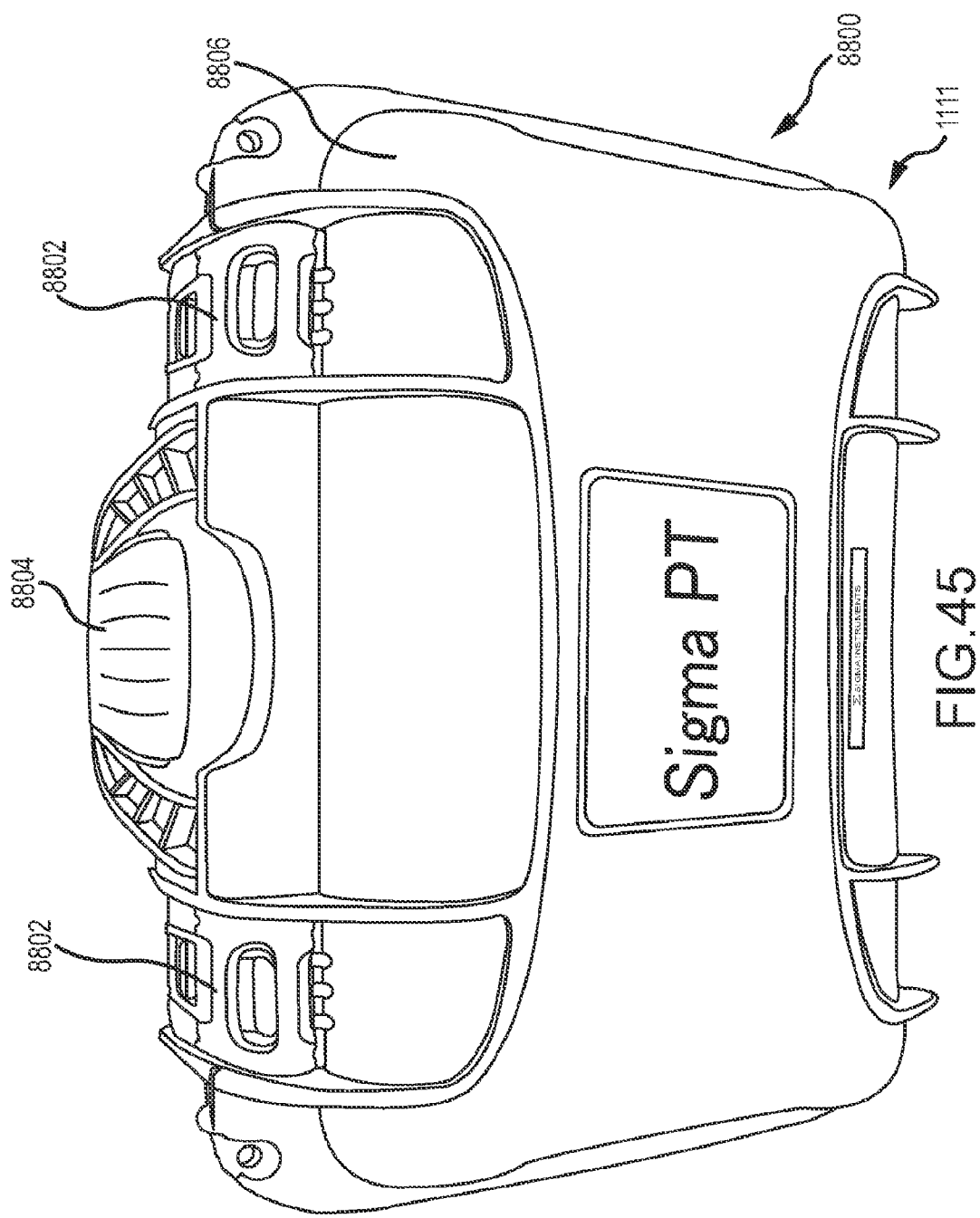
FIG. 45 is an isometric view of an embodiment of the physical therapy treatment system for treating the tissue of a patient, wherein a case or housing that encloses and protects the system is closed.

As illustrated in FIG. 45, which is an isometric view of an embodiment of the physical therapy treatment system or preoperative and postoperative tissue treatment system 1111 for treating the tissue of a patient, the system 1111 may include a case or housing 8800 that encloses and protects the system. The case 8800 may be secured in a closed state via latches 8802 as illustrated in FIG. 45. The case 8800 may also include a handle 8804 that extends from the sidewalls or shell 8806 of the case.

Figure 46:
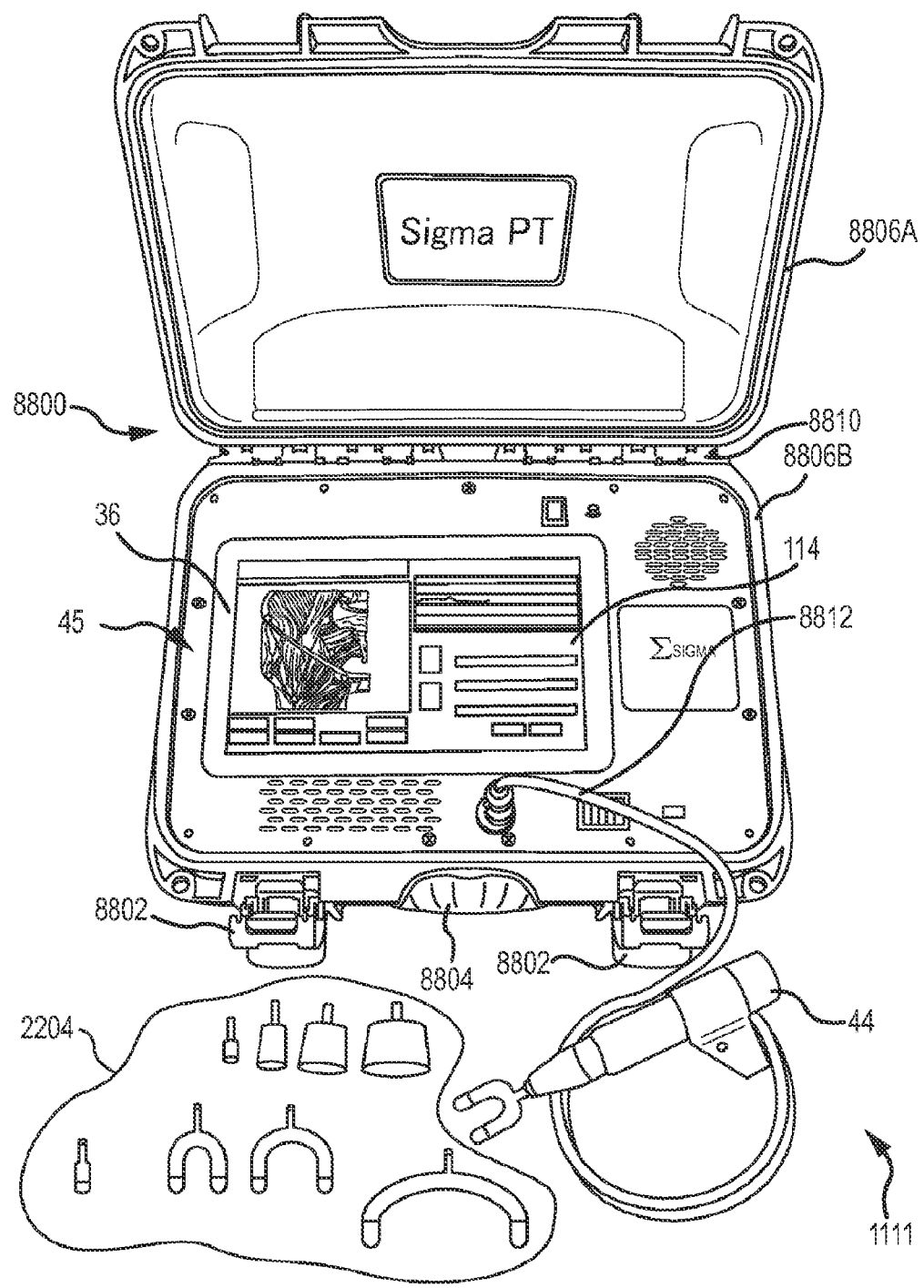
FIG. 46 is an isometric view of the physical therapy system of FIG. 45, wherein the case or housing is opened up to reveal the display, input device, impulse stimulator instrument and electrodes.

As shown in FIG. 46, which is an isometric view of the treatment system 1111 of FIG. 45 with the case 8800 opened up to reveal the display 36 and input device 114, the case 8800 has a clamshell arrangement with a top sidewall 8806A and a bottom sidewall 8806B pivotally secured to each other via a hinge 8810. The computing device 45 of the system 1111, along with the display 36 and input device 114 are contained in the bottom sidewall 8806B. The computing device 45 may be as described above with respect to configuration, components and operation.

The system 1111 may include the impulse stimulator instrument 44 with electrodes 14 supported on the tip of the instrument 44 as can be understood from FIG. 2, as discussed above. The impulse stimulator instrument 44 may be as described above with respect to configuration, components and operation. The impulse stimulator instrument 44 is capable of being electrically coupled to the computing device 45 via an electrical cable 8812. Multiple types of probes 2204 similar to those described above are provided for coupling to the impulse stimulator instrument 44.

Figure 47:
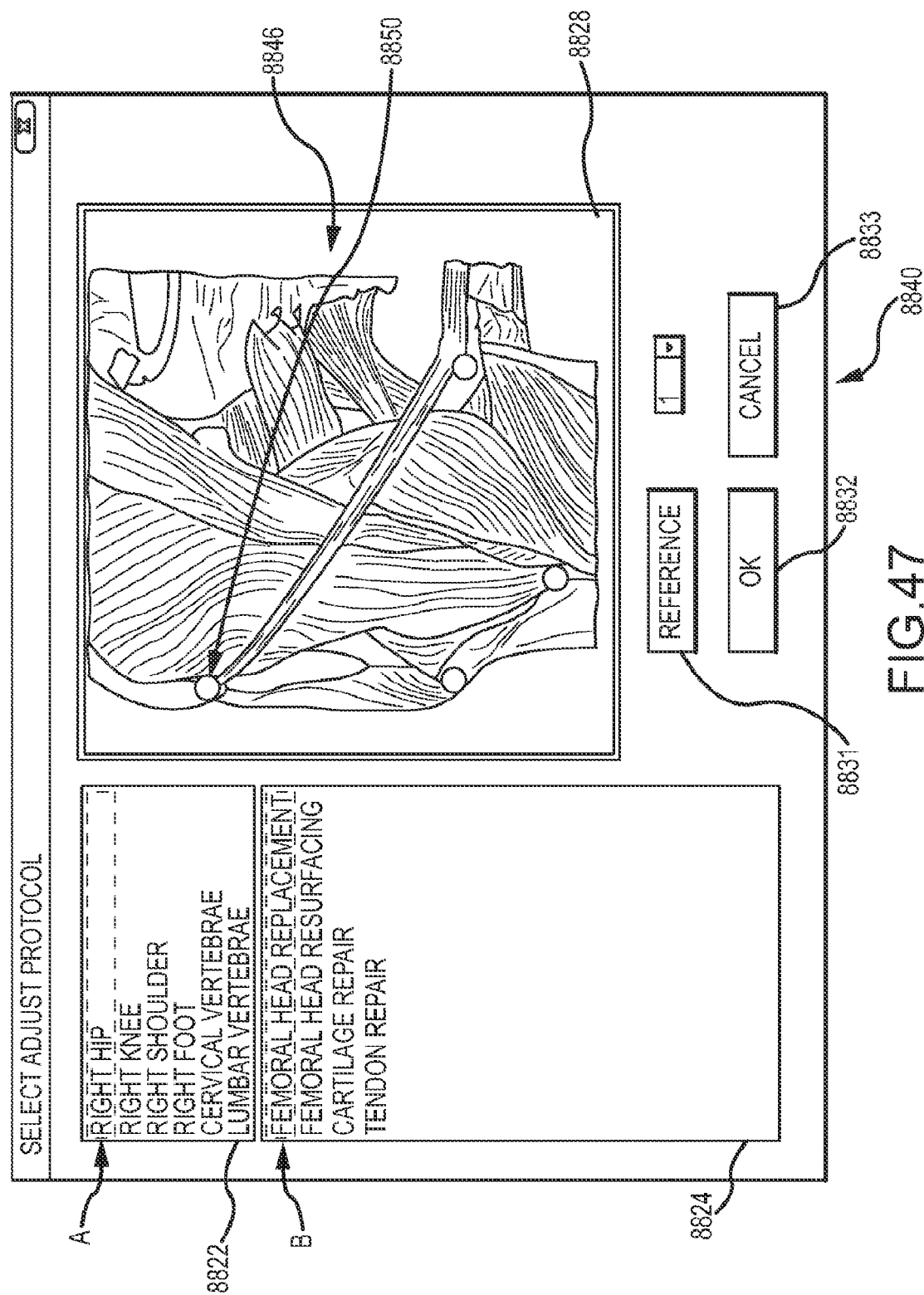
FIG. 47 depicts another GUI for display on the display depicted in FIG. 46, wherein the GUI is associated with the setup of the system for the treatment of a patient hip.

FIG. 47 depicts a GUI 8840 for display on the display 36 depicted in FIG. 46, wherein the GUI 8840 is associated with the setup of the system 1111 for the treatment of a patient hip region, the hip being the target of an arthroplasty or other surgical procedure. While this discussion is given in the context of the hip being the surgical target, this discussion is given merely as one example, and the system 1111 and its treatment methods may be applied to any other location on the patient's body and in the context of preoperative and/or postoperative treatment associated with any other type of surgical procedure.

As shown in FIG. 47, the GUI 8840 includes surgical site selection window 8822, wherein, as indicated by Arrow A, "right hip" has already been selected from other listed sites including, for example, right knee, right shoulder, right ankle, right wrist, right foot, cervical vertebrae, lumbar vertebrae, radius, tibia, femur, heart, liver, lungs, etc. The surgical site can include any location on or system of the patient including, for example and without limitation, any skeletal bone or joint, any connective tissue, any body organ or system, any location or side associate with these body elements, etc. The GUI 8840 also includes a treatment region selection window 8824, wherein, as indicated by Arrow B, "femoral head replacement" has already been selected from other listed hip treatments applicable to the hip, such as, for example, femoral head resurfacing, cartilage repair, tendon repair, etc. As a result of the selection of the "femoral head replacement" at Arrow B in window 8824, an image 8846 of a right anterior region of a patient hip is depicted in an image window 8828. Where the associated treatment may require other views of the hip, such as, for example, a lateral view and/or a posterior view, such views will be provided on the display and may be toggled between during the course of the treatment.

As indicated in FIG. 47, a trigger point 8850 for an associated treatment is shown in the image 8846. Touch sensitive screen buttons "Reference", "OK" and "Cancel" 8831-8833 are also included in the GUI 8840. In one embodiment, useful reference information may be accessed by the operator by selecting button 8831. Pressing button 8832 will return to the treatment screen and setup the system using the settings found in the selected treatment protocol. Pressing button 8833 will cause the selection screen to return to the treatment screen in its' last mode.

In one embodiment, the system 1111 disclosed herein can be used to improve the surgical outcome following a surgical procedure such as, for example, a hip, knee or shoulder arthroplasty. For example, in one embodiment, the system can be used to provide three treatments with the system 1111 one to two weeks before surgery and a series of ten to twelve treatments following surgery. There would be a two to four day rest between treatment cycles for the preoperative and postoperative treatments. The postoperative treatment would begin within two to ten days after the surgery, based on patient tolerance.

As can be understood from FIG. 41, in one example of a hip arthroplasty treatment deliverable via the system 1111, treatment via the instrument 44 of the system is applied to the anterior, posterior, and lateral aspects of the hip. As can be understood from FIG. 42, in one example of a knee arthroplasty treatment deliverable via the system 1111, treatment via the instrument 44 of the system is applied to the anterior, lateral and dorsal aspects of the knee. In one example of a shoulder arthroplasty treatment deliverable via the system 1111, treatment via the instrument 44 of the system is applied to the anterior, posterior and lateral aspects of the shoulder. In one embodiment of the aforementioned hip, knee and shoulder treatments, placement of the treatment head 13 (shown in FIG. 1) should be placed approximately two to three centimeters from the surgical incision or puncture wound. As can be understood from the discussion of the system 1111 provided above, the treatment settings can be individually set or automatically by selecting the hip, knee, or shoulder treatment algorithm for arthroplasty. In one embodiment, the default treatment settings are as follows: pulse limit 100; Force 20 lbs.; Frequency 8.6 Hz and Preload 1.

As can be understood from the preceding discussion, in a first embodiment of the system, the system 1111 is a system for treating tissue associated with a desired outcome of a surgical procedure on a patient. The system 1111 includes a display screen 36, a computer processor 34, an input device 500, a memory 37, and a treatment head 44. The display screen is configured to display information associated with the treatment of the tissue. The computer processor is configured to provide for the selection of a type of surgery and a surgical location on the patient. The surgical location is shown on the display screen as a part of an image 1702 of a patient region associated with the surgical location. A treatment point 1704A-D, which is associated with the treatment of the tissue, is identified on the image. The input device is in electrical communication with the display screen and configured to receive information associated with the treatment of the tissue to be delivered at the treatment point. The memory is in electrical communication with the CPU and includes treatment parameters associated with the treatment of the tissue to be delivered at the treatment point. The treatment head is in electrical communication with the computer processor and configured to deliver at least one of impulse and/or electrical therapy energy to the treatment point in accordance with the treatment parameters.

Also, as can be understood from the preceding discussion, in a second embodiment of the system, the system 1111 is a system for treating tissue associated with a desired outcome of a surgical procedure on a patient. The system includes a database N122 contained in a memory 37. The database contains data categorized by surgical locations. The data includes a plurality of anatomical images 1702, a plurality of treatment points 1704A-D identified on the plurality of anatomical images, and a plurality of treatment protocols N210 associated with plurality of treatment points. The system is configured such that a selection of a specific surgical location and a specific surgical procedure to occur at the specific surgical location causes an image 1702 of a specific region of the patient to be displayed on a display of the system, the image of the specific region including the specific surgical location. At least one treatment point 1704A-D is caused to be displayed on the image of the specific region. The treatment point is stored in the database as part of the plurality of treatment points and associated with at least one treatment protocol of the plurality of treatment protocols.

In a version of the second embodiment of the system 1111, the system is also configured such that a selection of the specific surgical location from the database provides the ability to input information into the system regarding the specific surgical procedure to occur at the specific surgical location.

In a version of the second embodiment of the system 1111, when the specific surgical location is a knee, the surgical procedure comprises at least one of the following: total arthroplasty; uni-compartmental arthroplasty; ligament repair; meniscus repair, torn or ruptured tendon repair, or torn or ruptured muscle repair. Also, the specific region comprises a knee region comprising a distal region of a femur and a proximal region of a tibia. Finally, when the at least one treatment point is caused to be displayed on the image of the specific region, the at least one treatment point is displayed on at least one of the following locations: a distal femur proximal to the patella; a medial or lateral epicondyle; a medial or lateral meniscus; a medial or lateral collateral ligament; a patella tendon; a lateral head of a fibula; a tibial tuberosity; a proximal tibia; or an adductor tubercle.

In a version of the second embodiment of the system 1111, when the specific surgical location is a hip, the surgical procedure comprises at least one of the following: femoral head total arthroplasty; femoral head resurfacing; ligament repair; torn or ruptured tendon repair; torn or ruptured muscle repair; or femur fracture repair. Also, the specific region comprises a hip region comprising a proximal region of a femur and region of an iliac surrounding a hip joint. Finally, when the at least one treatment point is caused to be displayed on the image of the specific region, the at least one treatment point is displayed on at least one of the following locations: an anterior superior iliac crest; an inguinal ligament; a greater or lesser trochanter; a trochanteric bursa; an anterior or lateral proximal femur; a proximal hamstring tendon; or a proximal hamstring muscle.

In a version of the second embodiment of the system 1111, when the specific surgical location is a shoulder, the surgical procedure comprises at least one of the following: rotator cuff repair; total shoulder arthroplasty; shoulder joint resurfacing; arthroscopic acromioplasty; ligament repair; humerus fracture repair; clavicle fracture repair; torn or ruptured tendon repair; torn or ruptured muscle repair; impingement of scapula; removal of calcified deposits in the supraspinatus or related tendons; or Mumford procedure. Also, the specific region comprises a shoulder region comprising a proximal region of a humerus and a lateral region of at least one of a clavicle or a scapula. Finally, when the at least one treatment point is caused to be displayed on the image of the specific region, the at least one treatment point is displayed on at least one of the following locations: an anterior acromioclavicular joint; an anterior acromion; an anterior corticoid process; an anterior glenohumeral joint; an anterior greater or lesser tubercle; a spine of a scapula; a supraspinatus muscle; a subacromial bursa; a grove for a bicep tendon; or a deltoid muscle.

In a version of the second embodiment of the system 1111, the system also includes a treatment head 44 electrically coupled to the database and configured to deliver at least one of impulse and/or electrical therapy energy to the treatment point in accordance with the at least one treatment protocol of the plurality of treatment protocols.

As can be understood from the preceding discussion, in a third embodiment of the system 1111, the system is for delivering at least one of preoperative or postoperative therapy to tissue associated with a surgical outcome. The system 1111 includes a database N122, an input device 500, a display device 36, a treatment head 44, and a CPU 34. The database includes a plurality of anatomical images 1702 respectively correlated to a plurality of surgical target sites. The input device is configured to allow a selection of a specific surgical target site from the plurality of surgical target sites. The CPU is in communication with the database, input device, display device and treatment head. When the specific surgical target site is selected from the plurality of surgical target sites, the CPU causes a respective specific anatomical image to be displayed on the display and treatment points 1704A-D to be indicated on the displayed specific anatomical image. The CPU causes the treatment head 44 to function in accordance with a treatment protocol corresponding to the treatment points.

In a version of the third embodiment of the system 1111, the input device 500 includes a touch screen or a keyboard. In a version of the third embodiment of the system 1111, the plurality of surgical target sites includes surgical procedures. In a version of the third embodiment of the system 1111, the treatment head 44 is configured to deliver at least one of impulse and/or electrical therapy energy in accordance with the treatment protocol. In a version of the third embodiment of the system 1111, the database further includes a plurality of treatment protocols correlated to a plurality of treatment points correlated with the plurality of surgical sites.

As can be understood from the preceding discussion, in an embodiment of the treatment method, the method is for delivering at least one of preoperative or postoperative therapy to tissue associated with a surgical outcome. The method includes: 1) imputing at least one of a surgical procedure or surgical target site into an apparatus, the apparatus displaying on a display an anatomical image comprising the surgical target site, the apparatus also displaying treatment points on anatomical landmarks shown in the anatomical image, the apparatus correlating the treatment points with the at least one of the surgical procedure or surgical target site, the apparatus correlating a treatment protocol with the treatment points; and 2) using a treatment head of the apparatus to apply therapy to locations on a patient that correspond to the treatment points, the therapy being configured according to the therapy protocol controlling the treatment head.

In one version of the method, when the surgical procedure concerns a knee or the surgical target site comprises a knee, the surgical procedure comprises at least one of the following: total arthroplasty; uni-compartmental arthroplasty; ligament repair; meniscus repair, torn or ruptured tendon repair, or torn or ruptured muscle repair. Also, the anatomical image comprises a knee region comprising a distal region of a femur and a proximal region of a tibia. Finally, when the treatment points are displayed on the anatomical landmarks shown in the anatomical image, the treatment points are displayed at least some of the following locations: a distal femur proximal to the patella; a medial or lateral epicondyle; a medial or lateral meniscus; a medial or lateral collateral ligament; a patella tendon; a lateral head of a fibula; a tibial tuberosity; a proximal tibia; or an adductor tubercle.

In one version of the method, when the surgical procedure concerns a hip or the surgical target site comprises a hip, the surgical procedure comprises at least one of the following: femoral head total arthroplasty; femoral head resurfacing; ligament repair; torn or ruptured tendon repair; torn or ruptured muscle repair; or femur fracture repair. Also, the anatomical image comprises a hip region comprising a proximal region of a femur and region of an iliac surrounding a hip joint. Finally, when the treatment points are displayed on the anatomical landmarks shown in the anatomical image, the treatment points are displayed at least some of the following locations: an anterior superior iliac crest; an inguinal ligament; a greater or lesser trochanter; a trochanteric bursa; an anterior or lateral proximal femur; a proximal hamstring tendon; or a proximal hamstring muscle.

In one version of the method, when the surgical procedure concerns a shoulder or the surgical target site comprises a shoulder, the surgical procedure comprises at least one of the following: rotator cuff repair; total shoulder arthroplasty; shoulder joint resurfacing; arthroscopic acromioplasty; ligament repair; humerus fracture repair; clavicle fracture repair; torn or ruptured tendon repair; torn or ruptured muscle repair; impingement of scapula; removal of calcified deposits in the supraspinatus or related tendons; or Mumford procedure. Also, the anatomical image comprises a shoulder region comprising a proximal region of a humerus and a lateral region of at least one of a clavicle or a scapula. Finally, when the treatment points are displayed on the anatomical landmarks shown in the anatomical image, the treatment points are displayed at least some of the following locations: an anterior acromioclavicular joint; an anterior acromion; an anterior corticoid process; an anterior glenohumeral joint; an anterior greater or lesser tubercle; a spine of a scapula; a supraspinatus muscle; a subacromial bursa; a grove for a bicep tendon; or a deltoid muscle.

In one version of the method, the treatment head is configured to deliver at least one of impulse and/or electrical therapy energy to the treatment points in accordance with the therapy protocol.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. A system for treating tissue associated with a desired outcome of a surgical procedure on a patient, the system comprising:
   a database contained in a memory, wherein the database comprises a plurality of anatomical images, a plurality of treatment points identified on the plurality of anatomical images, and a plurality of treatment protocols associated with the plurality of treatment points;

a treatment head configured to deliver at least one of impulse and/or electrical therapy energy to the treatment point in accordance with at least one treatment protocol of the plurality of treatment protocols, the treatment head comprising a probe, an electrode operably coupled to the probe, a force impulse wave sensor, and a pressure sensor separated from the force impulse wave sensor; and a display device;

wherein the system is configured such that a selection of a specific surgical location and a specific surgical procedure that occurs at the specific surgical location causes an image of a specific region of the patient to be displayed on the display device, wherein the selection of the specific surgical location from the database provides ability to input information into the system regarding the specific surgical procedure to occur at the specific surgical location, wherein at least one treatment point of the plurality of treatment points is caused to be displayed on the image of the specific region, the at least one treatment point being stored in the database and associated with at least one treatment protocol.

2. The system of claim 1, wherein the image of the specific region comprises the specific surgical location.

3. The system of claim 1, wherein, when the specific surgical location is a knee, the surgical procedure comprises at least one of the following: total arthroplasty; unicompartmental arthroplasty; ligament repair; meniscus repair, torn or ruptured tendon repair, or torn or ruptured muscle repair, wherein the specific region comprises a knee region comprising a distal region of a femur and a proximal region of a tibia, wherein, when the at least one treatment point is caused to be displayed on the image of the specific region, the at least one treatment point is displayed on at least one of the following locations: a distal femur proximal to the patella; a medial or lateral epicondyle; a medial or lateral meniscus; a medial or lateral collateral ligament; a patella tendon; a lateral head of a fibula; a tibial tuberosity; a proximal tibia; or an adductor tubercle.

4. The system of claim 1, wherein, when the specific surgical location is a hip, the surgical procedure comprises at least one of the following: femoral head total arthroplasty; femoral head resurfacing; ligament repair; torn or ruptured tendon repair; torn or ruptured muscle repair; or femur fracture repair, wherein the specific region comprises a hip region comprising a proximal region of a femur and region of an iliac surrounding a hip joint, wherein, when the at least one treatment point is caused to be displayed on the image of the specific region, the at least one treatment point is displayed on at least one of the following locations: an anterior superior iliac crest; an inguinal ligament; a greater or lesser trochanter; a trochanteric bursa; an anterior or lateral proximal femur; a proximal hamstring tendon; or a proximal hamstring muscle.

5. The system of claim 1, wherein, when the specific surgical location is a shoulder, the surgical procedure comprises at least one of the following: rotator cuff repair; total shoulder arthroplasty; shoulder joint resurfacing; arthroscopic acromioplasty; ligament repair; humerus fracture repair; clavicle fracture repair; torn or ruptured tendon repair; torn or ruptured muscle repair; impingement of scapula; removal of calcified deposits in the supraspinatus or related tendons; or umford procedure, wherein the specific region comprises a shoulder region comprising a proximal region of a humerus and a lateral region of at least one of a clavicle or a scapula, wherein, when the at least one treatment point is caused to be displayed on the image of the specific region, the at least one treatment point is displayed on at least one of the following locations: an anterior acromioclavicular joint; an anterior acromion; an anterior corticoid process; an anterior glenohumeral joint; an anterior greater or lesser tubercle; a spine of a scapula; a supraspinatus muscle; a subacromial bursa; a grove for a bicep tendon; or a deltoid muscle.

6. The system of claim 1, wherein the pressure sensor is configured so that when the probe is pressed against the tissue and reaches a predetermined pressure, the pressure sensor causes a release of current such that the probe and electrode respectively deliver the at least one of impulse and/or electrical therapy energy to the treatment point wherein the force impulse wave sensor is configured to sense a frequency of the impulse associated with the at least one treatment point, wherein the at least one treatment protocol for the at least treatment point is modified based on the sensed frequency of the impulse.

7. The system of claim 1, further comprising an input device configured to allow the selection of the specific surgical target site from the plurality of surgical target sites.

8. The system of claim 1, wherein the display device comprises at least one of a touch screen or a keyboard.

9. The system of claim 1, further comprising a CPU in communication with the database, the treatment head and the display device.

10. A system for delivering at least one of preoperative or postoperative therapy to tissue associated with a surgical outcome, the system comprising:

a database comprising a plurality of anatomical images respectively correlated to a plurality of surgical target sites;

an input device configured to allow a selection of a specific surgical target site from the plurality of surgical target sites;

a display device;

a treatment head configured to deliver at least one of impulse and/or electrical therapy energy to the treatment point in accordance with at least one therapy protocol, the treatment head comprising a probe, an electrode operably coupled to the probe, a force impulse wave sensor, and a pressure sensor separated from the force impulse wave sensor; and a CPU in communication with the database, input device, the display device, and the treatment head, wherein, when the specific surgical target site is selected from the plurality of surgical target sites, the CPU causes a respective specific anatomical image to be displayed on the display and treatment points to be indicated on the displayed specific anatomical image, wherein the CPU causes the treatment head to function in accordance with the at least one therapy protocol corresponding to the treatment points.

11. The system of claim 10, wherein the input device comprises at least one of a touch screen or a keyboard.

12. The system of claim 10, wherein the plurality of surgical target sites comprises surgical procedures.

13. The system of claim 10, wherein the treatment head is configured to deliver at least one of impulse and/or electrical therapy energy in accordance with the at least one therapy protocol.

14. The system of claim 10, wherein the database further comprises a plurality of therapy protocols correlated to a plurality of treatment points correlated with the plurality of surgical target sites.

15. A method for delivering at least one of preoperative or postoperative therapy to tissue associated with a surgical outcome, the method comprising:
- inputting at least one of a surgical procedure or surgical target site into an apparatus comprising a display and a treatment head, the treatment head comprising a probe, an electrode operably coupled to the probe, a force impulse wave sensor, and a pressure sensor separated from the force impulse wave sensor, the display displaying an anatomical image comprising the surgical target site, the display further displaying treatment points on anatomical landmarks shown in the anatomical image, the apparatus correlating the treatment points with the at least one of the surgical procedure or surgical target site, the apparatus correlating at least one therapy protocol with one of the treatment points; and
- using the treatment head to apply therapy to locations on a patient that correspond to the treatment points, the therapy being configured according to the at least one therapy protocol controlling the treatment head,
- wherein the treatment head is configured to deliver at least one of impulse and/or electrical therapy energy to the one of the treatment points in accordance with the at least one therapy protocol.

16. The method of claim 15, wherein, when the surgical procedure concerns a knee or the surgical target site comprises a knee, the surgical procedure comprises at least one of the following: total arthroplasty; uni-compartmental arthroplasty; ligament repair; meniscus repair, torn or ruptured tendon repair, or torn or ruptured muscle repair,
- wherein the anatomical image comprises a knee region comprising a distal region of a femur and a proximal region of a tibia,
- wherein, when the treatment points are displayed on the anatomical landmarks shown in the anatomical image, the treatment points are displayed at least some of the following locations: a distal femur proximal to the patella; a medial or lateral epicondyle; a medial or lateral meniscus; a medial or lateral collateral ligament; a patella tendon; a lateral head of a fibula; a tibial tuberosity; a proximal tibia; or an adductor tubercle.

17. The method of claim 15, wherein, when the surgical procedure concerns a hip or the surgical target site comprises a hip, the surgical procedure comprises at least one of the following: femoral head total arthroplasty; femoral head resurfacing; ligament repair; torn or ruptured tendon repair; torn or ruptured muscle repair; or femur fracture repair,
- wherein the anatomical image comprises a hip region comprising a proximal region of a femur and region of an iliac surrounding a hip joint,
- wherein, when the treatment points are displayed on the anatomical landmarks shown in the anatomical image, the treatment points are displayed at least some of the following locations: an anterior superior iliac crest; an inguinal ligament; a greater or lesser trochanter; a trochanteric bursa; an anterior or lateral proximal femur; a proximal hamstring tendon; or a proximal hamstring muscle.

18. The method of claim 15, wherein, when the surgical procedure concerns a shoulder or the surgical target site comprises a shoulder, the surgical procedure comprises at least one of the following: rotator cuff repair; total shoulder arthroplasty; shoulder joint resurfacing; arthroscopic acromioplasty; ligament repair; humerus fracture repair; clavicle fracture repair; torn or ruptured tendon repair; torn or ruptured muscle repair; impingement of scapula; removal of calcified deposits in the supraspinatus or related tendons; or umford procedure,
- wherein the anatomical image comprises a shoulder region comprising a proximal region of a humerus and a lateral region of at least one of a clavicle or a scapula,
- wherein, when the treatment points are displayed on the anatomical landmarks shown in the anatomical image, the treatment points are displayed at least some of the following locations: an anterior acromioclavicular joint; an anterior acromion; an anterior corticoid process; an anterior glenohumeral joint; an anterior greater or lesser tubercle; a spine of a scapula; a supraspinatus muscle; a subacromial bursa; a grove for a bicep tendon; or a deltoid muscle.

19. The method of claim 15, wherein the pressure sensor configured so that when the probe is pressed against the tissue and reaches a predetermined pressure, the pressure sensor causes a release of current such that the probe and electrode respectively deliver the at least one of impulse and/or electrical therapy energy to the treatment point, and the force impulse wave sensor configured to sense a frequency of the impulse associated with the at least one treatment point, wherein the at least one therapy protocol for the at least treatment point is modified based on the sensed frequency of the impulse.

* * * * *